United States Patent
Wingeier et al.

(10) Patent No.: US 10,238,869 B2
(45) Date of Patent: Mar. 26, 2019

(54) ELECTRODE SYSTEM FOR ELECTRICAL STIMULATION

(71) Applicant: Halo Neuro, Inc., San Francisco, CA (US)

(72) Inventors: Brett Wingeier, San Francisco, CA (US); Tal Bar-Or, San Francisco, CA (US); Colin Davis, San Francisco, CA (US); Victoria Hammett, San Francisco, CA (US); Randall Lin, San Francisco, CA (US)

(73) Assignee: Halo Neuro, Inc., San Francisco, CA (US)

( * ) Notice: Subject to any disclaimer, the term of this patent is extended or adjusted under 35 U.S.C. 154(b) by 0 days.

(21) Appl. No.: 15/289,653

(22) Filed: Oct. 10, 2016

(65) Prior Publication Data

US 2017/0021158 A1 Jan. 26, 2017

Related U.S. Application Data

(63) Continuation of application No. 14/878,647, filed on Oct. 8, 2015, now Pat. No. 9,486,618, which is a (Continued)

(51) Int. Cl.
*A61N 1/04* (2006.01)
*A61B 5/0478* (2006.01)
(Continued)

(52) U.S. Cl.
CPC ........ *A61N 1/36025* (2013.01); *A61B 5/0476* (2013.01); *A61B 5/0478* (2013.01);
(Continued)

(58) Field of Classification Search
CPC .. A61N 1/0456; A61N 1/0529; A61N 1/0476; A61B 5/6868; A61B 5/0492;
(Continued)

(56) References Cited

U.S. PATENT DOCUMENTS 3,472,233 A 10/1969 Sarbacher
4,977,895 A 12/1990 Tannenbaum
(Continued)

FOREIGN PATENT DOCUMENTS

EP 2449961 A1 5/2012
KR 101685124 B1 12/2016
(Continued)

OTHER PUBLICATIONS

US 8,919,831, 07/2011, Tateishi et al. (withdrawn)

*Primary Examiner* — Mark Bockelman
(74) *Attorney, Agent, or Firm* — Jeffrey Schox

(57) ABSTRACT

A system for electrically stimulating a user comprising: a first housing portion defining an array of openings; an array of permeable bodies with portions exposed through the array of openings and wetted with a solution that facilitates electrical coupling between the system and a body region of the user, wherein each permeable body has a cavity at a proximal portion and a distal portion and is configured to transmit the solution to the body region of the user; a substrate region defining an array of protrusions configured to support the array of permeable bodies and composed of a conductive polymer; and a set of conductors in communication with the substrate region and including a first conductor that provides a first subset of the array of permeable bodies with a first polarity and a second conductor that provides a second subset of the array of permeable bodies with a second polarity.

18 Claims, 26 Drawing Sheets

Related U.S. Application Data continuation-in-part of application No. 14/470,683, filed on Aug. 27, 2014, now Pat. No. 9,889,290.

(60) Provisional application No. 62/221,475, filed on Sep. 21, 2015, provisional application No. 62/139,975, filed on Mar. 30, 2015, provisional application No. 62/139,899, filed on Mar. 30, 2015, provisional application No. 62/127,708, filed on Mar. 3, 2015, provisional application No. 62/093,326, filed on Dec. 17, 2014, provisional application No. 62/061,273, filed on Oct. 8, 2014, provisional application No. 61/870,643, filed on Aug. 27, 2013, provisional application No. 61/870,658, filed on Aug. 27, 2013, provisional application No. 61/870,713, filed on Aug. 27, 2013, provisional application No. 61/870,665, filed on Aug. 27, 2013, provisional application No. 61/870,640, filed on Aug. 27, 2013, provisional application No. 61/870,631, filed on Aug. 27, 2013, provisional application No. 61/870,715, filed on Aug. 27, 2013, provisional application No. 61/870,653, filed on Aug. 27, 2013, provisional application No. 61/870,710, filed on Aug. 27, 2013.

(51) Int. Cl.

| | |
|---|---|
| *A61B 5/00* | (2006.01) |
| *A61B 5/0496* | (2006.01) |
| *A61B 5/053* | (2006.01) |
| *A61N 1/36* | (2006.01) |
| *A61B 5/0492* | (2006.01) |
| *A61B 5/0476* | (2006.01) |

(52) U.S. Cl.
CPC .......... *A61B 5/0492* (2013.01); *A61B 5/0496* (2013.01); *A61B 5/0533* (2013.01); *A61B 5/6814* (2013.01); *A61N 1/0456* (2013.01); *A61N 1/0476* (2013.01); *A61B 2562/0209* (2013.01); *A61B 2562/227* (2013.01)

(58) Field of Classification Search
CPC . A61B 5/0478; A61B 5/6814; A61B 5/04001; A61B 5/04008; A61B 5/0482; A61B 2562/0209; A61B 2562/227; A61B 5/0496; A61B 5/0533
See application file for complete search history.

(56) References Cited

U.S. PATENT DOCUMENTS

| | | | |
|---|---|---|---|
| 5,058,605 A | 10/1991 | Slovak | |
| 5,087,242 A | 2/1992 | Petelenz et al. | |
| 5,137,817 A | 8/1992 | Busta et al. | |
| 5,250,023 A | 10/1993 | Lee et al. | |
| 5,387,231 A | 2/1995 | Sporer | |
| 5,622,168 A | 4/1997 | Keusch et al. | |
| 6,077,237 A | 6/2000 | Campbell et al. | |
| 6,263,226 B1 | 7/2001 | Axelgaard et al. | |
| 6,379,324 B1 | 4/2002 | Gartstein et al. | |
| 6,406,811 B1 | 6/2002 | Hall et al. | |
| 6,480,743 B1 | 11/2002 | Kirkpatrick et al. | |
| 6,505,079 B1 | 1/2003 | Foster et al. | |
| 6,510,333 B1 | 1/2003 | Licata et al. | |
| 7,024,247 B2 | 4/2006 | Gliner et al. | |
| 7,551,952 B2 | 6/2009 | Gevins et al. | |
| 7,610,095 B2 | 10/2009 | Naisberg | |
| 7,813,802 B2 | 10/2010 | Tcheng et al. | |
| 7,818,515 B1 | 10/2010 | Umbehocker et al. | |
| 7,828,947 B2 | 11/2010 | Oki et al. | |
| 7,877,146 B2 | 1/2011 | Ansarinia et al. | |
| 7,894,905 B2 | 2/2011 | John et al. | |
| 7,966,073 B2 | 6/2011 | Pless et al. | |
| 7,988,917 B2 | 8/2011 | Roesicke et al. | |
| 8,121,694 B2 | 2/2012 | Molnar et al. | |
| 8,195,174 B2 | 6/2012 | Lee et al. | |
| 8,239,030 B1 | 8/2012 | Hagedorn et al. | |
| 8,290,596 B2 | 10/2012 | Wei et al. | |
| 8,301,265 B2 | 10/2012 | Starkebaum | |
| 8,349,554 B2 | 1/2013 | Bahrami et al. | |
| 8,380,316 B2 | 2/2013 | Hagedorn et al. | |
| 8,419,716 B2 | 4/2013 | Weissenrieder-Norlin et al. | |
| 8,473,063 B2 | 6/2013 | Gupta et al. | |
| 8,554,324 B2 | 10/2013 | Brocke | |
| 8,583,237 B2 | 11/2013 | Bedenbaugh | |
| 8,626,259 B2 | 1/2014 | Besio | |
| 8,706,181 B2 | 4/2014 | Stypulkowski et al. | |
| 8,795,174 B2 | 8/2014 | Manicka et al. | |
| 8,818,515 B2 | 8/2014 | Bikson et al. | |
| 8,838,247 B2 | 9/2014 | Hagedorn et al. | |
| 8,874,220 B2 | 10/2014 | Draghici et al. | |
| 8,874,227 B2 | 10/2014 | Simon et al. | |
| 8,880,173 B2 | 11/2014 | Diubaldi et al. | |
| 8,903,494 B2 | 12/2014 | Goldwasser et al. | |
| 8,938,301 B2 | 1/2015 | Hagedorn | |
| 8,979,837 B2 | 3/2015 | De La Rama et al. | |
| 8,989,863 B2 | 3/2015 | Osorio | |
| 9,002,458 B2 | 4/2015 | Pal et al. | |
| 9,080,918 B2 | 7/2015 | Fishel et al. | |
| 9,186,505 B2 | 11/2015 | Katsnelson | |
| 9,393,430 B2 | 7/2016 | Demers et al. | |
| 9,399,126 B2 | 7/2016 | Pal et al. | |
| 9,433,774 B2 | 9/2016 | Dar et al. | |
| 9,440,063 B2 | 9/2016 | Ho et al. | |
| 9,440,070 B2 | 9/2016 | Goldwasser et al. | |
| 9,486,618 B2 | 11/2016 | Wingeier et al. | |
| 9,517,345 B2 | 12/2016 | Meffin et al. | |
| 9,630,005 B2 | 4/2017 | Wingeier et al. | |
| 9,643,001 B2 | 5/2017 | Wu et al. | |
| 9,731,127 B2 | 8/2017 | Kealey et al. | |
| 9,913,973 B2 | 3/2018 | Yanaki | |
| 2002/0169485 A1 | 11/2002 | Pless et al. | |
| 2005/0165460 A1 | 7/2005 | Erfan | |
| 2006/0111754 A1 | 5/2006 | Ansarinia et al. | |
| 2006/0212093 A1 | 9/2006 | Pless et al. | |
| 2006/0229502 A1 | 10/2006 | Pollock et al. | |
| 2007/0015984 A1 | 1/2007 | Yeo et al. | |
| 2007/0093706 A1 | 4/2007 | Gevins et al. | |
| 2007/0118070 A1 | 5/2007 | Cormier et al. | |
| 2007/0237678 A1 | 10/2007 | Roesicke et al. | |
| 2007/0237797 A1 | 10/2007 | Peyman | |
| 2007/0238945 A1 | 10/2007 | Delic et al. | |
| 2007/0250145 A1 | 10/2007 | Kraus et al. | |
| 2008/0021520 A1 | 1/2008 | Dietrich | |
| 2008/0027345 A1 | 1/2008 | Kumada et al. | |
| 2009/0099627 A1 | 4/2009 | Molnar et al. | |
| 2009/0105785 A1 | 4/2009 | Wei et al. | |
| 2009/0187159 A1 | 7/2009 | Greger et al. | |
| 2010/0030129 A1 | 2/2010 | Nitzan et al. | |
| 2010/0268287 A1 | 10/2010 | Celnik | |
| 2010/0330589 A1 | 12/2010 | Bahrami et al. | |
| 2011/0040291 A1 | 2/2011 | Weissenrieder-Norlin et al. | |
| 2011/0112590 A1 | 5/2011 | Molnar et al. | |
| 2011/0118806 A1 | 5/2011 | Pascual-Leone et al. | |
| 2011/0276112 A1 | 11/2011 | Simon et al. | |
| 2011/0288610 A1 | 11/2011 | Brocke | |
| 2011/0319975 A1 | 12/2011 | Ho et al. | |
| 2012/0065699 A1 | 3/2012 | Bedenbaugh | |
| 2012/0071947 A1 | 3/2012 | Gupta et al. | |
| 2012/0078323 A1 | 3/2012 | Osorio | |
| 2012/0184894 A1 | 7/2012 | Imran et al. | |
| 2012/0191157 A1 | 7/2012 | Stypulkowski et al. | |
| 2012/0226127 A1 | 9/2012 | Asjes et al. | |
| 2012/0289869 A1 | 11/2012 | Tyler | |
| 2013/0204315 A1 | 8/2013 | Wongsarnpigoon et al. | |
| 2013/0281759 A1 | 10/2013 | Hagedorn et al. | |
| 2014/0069212 A1 | 3/2014 | Fishel et al. | |
| 2014/0148872 A1 | 5/2014 | Goldwasser et al. | |
| 2014/0172041 A1 | 6/2014 | Draghici et al. | |
| 2014/0277324 A1 | 9/2014 | Diubaldi et al. | |
| 2014/0350431 A1 | 11/2014 | Hagedorn | |
| 2015/0065838 A1 | 3/2015 | Wingeier et al. | |

(56) References Cited

U.S. PATENT DOCUMENTS

| | | |
|---|---|---|
| 2015/0335877 A1 | 11/2015 | Jeffery et al. |
| 2015/0352357 A1 | 12/2015 | Wei et al. |
| 2015/0352364 A1 | 12/2015 | Meffin et al. |
| 2015/0360027 A1 | 12/2015 | Bachinski et al. |
| 2015/0374971 A1 | 12/2015 | Dar et al. |
| 2015/0375007 A1 | 12/2015 | Takeuchi et al. |
| 2016/0017558 A1 | 1/2016 | French |
| 2016/0175589 A1 | 6/2016 | Wingeier |
| 2016/0256105 A1 | 9/2016 | Boyle et al. |
| 2016/0303362 A1 | 10/2016 | Wu et al. |
| 2016/0346530 A1 | 12/2016 | Jeffery et al. |
| 2016/0360990 A1 | 12/2016 | Altshuler et al. |
| 2016/0366507 A1 | 12/2016 | Hou et al. |
| 2017/0021158 A1 | 1/2017 | Wingeier et al. |
| 2017/0224978 A1 | 8/2017 | Lee |
| 2017/0224990 A1 | 8/2017 | Goldwasser et al. |
| 2017/0368344 A1 | 12/2017 | Ironi et al. |
| 2018/0021565 A1 | 1/2018 | Dar et al. |

FOREIGN PATENT DOCUMENTS

| | | |
|---|---|---|
| WO | 2013004763 A1 | 1/2013 |
| WO | 2013113059 A1 | 8/2013 |

TOP VIEW

TOP VIEW

TOP VIEW

CROSS-SECTIONAL VIEW

ELEVATION VIEW

* Where portions of the substrate region (50) that interface with pads (62), examples of which are shown in FIGURE 5D below, can serve as conductors (60).

PLAN VIEW (SIDE ELECTRODE)

PLAN VIEW (CENTER ELECTRODE)

BOTTOM VIEW (DISTAL SURFACE)

CHANNEL CROSS SECTION

BOTTOM VIEW (DISTAL SURFACE)

PROTRUSION CROSS SECTION

PROTRUSION CROSS SECTION

Configuration During Initial
Placement On Scalp

Configuration In Which
Hair Has Been Pushed Aside

Underside (Scalp Side)

volumetric expansion
of permeable body area expansion
of permeable body

Permeable Bodies
Expand in Place

Features Extend from Posts
to Close Gap

Posts retract, exposing the
Permeable Bodies

ELECTRODE SYSTEM FOR ELECTRICAL STIMULATION

CROSS-REFERENCE TO RELATED APPLICATIONS

This application is a continuation of U.S. application Ser. No. 14/878,647, filed 8 Oct. 2015, which is a continuation-in-part application of U.S. application Ser. No. 14/470,683 filed 27 Aug. 2015, which claims the benefit of U.S. Provisional Application Ser. No. 61/870,631, filed 27 Aug. 2013, U.S. Provisional Application Ser. No. 61/870,640, filed 27 Aug. 2013, U.S. Provisional Application Ser. No. 61/870,643 filed 27 Aug. 2013, U.S. Provisional Application Ser. No. 61/870,653, filed 27 Aug. 2013, U.S. Provisional Application Ser. No. 61/870,658, filed 27 Aug. 2013, U.S. Provisional Application Ser. No. 61/870,665, filed 27 Aug. 2013, U.S. Provisional Application Ser. No. 61/870,710, filed 27 Aug. 2013, U.S. Provisional Application Ser. No. 61/870,713, filed 27 Aug. 2013, and U.S. Provisional Application Ser. No. 61/870,715, filed 27 Aug. 2013, which are each incorporated in its entirety herein by this reference.

This application also claims priority to U.S. application Ser. No. 14/878,647, filed 8 Oct. 2015 which claims the benefit of U.S. Provisional Application Ser. No. 62/061,273, filed 8 Oct. 2014, U.S. Provisional Application Ser. No. 62/093,326, filed 17 Dec. 2014, U.S. Provisional Application Ser. No. 62/127,708, filed 3 Mar. 2015, U.S. Provisional Application Ser. No. 62/139,899, filed 30 Mar. 2015, U.S. Provisional Application Ser. No. 62/139,975, filed 30 Mar. 2015, and U.S. Provisional Application Ser. No. 62/221,475, filed 21 Sep. 2015, which are each incorporated in its entirety herein by this reference.

TECHNICAL FIELD

This invention relates generally to the biosignals field, and more specifically to a new and useful electrode system for electrical stimulation.

BACKGROUND

Electrode systems in the biosignals field are used to transmit electrical signals to a subject, and can additionally or alternatively be used to detect or measure biosignals from the subject. Current electrode systems for electrical stimulation and/or biosignal detection are, however, insufficient for many reasons including inadequate contact between the subject and the electrode(s) of a system, non-robust contact between the subject and the electrode(s) of a system in providing proper impedance characteristics at an electrode-user body interface, subject discomfort while using an electrode system, and/or limited use within multiple electrical simulation or biosignal detection paradigms.

Thus, there is a need in the biosignals field for a new and useful electrode system for electrical stimulation and biosignal detection. This invention provides such a new and useful system.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. System

Figure 1A:
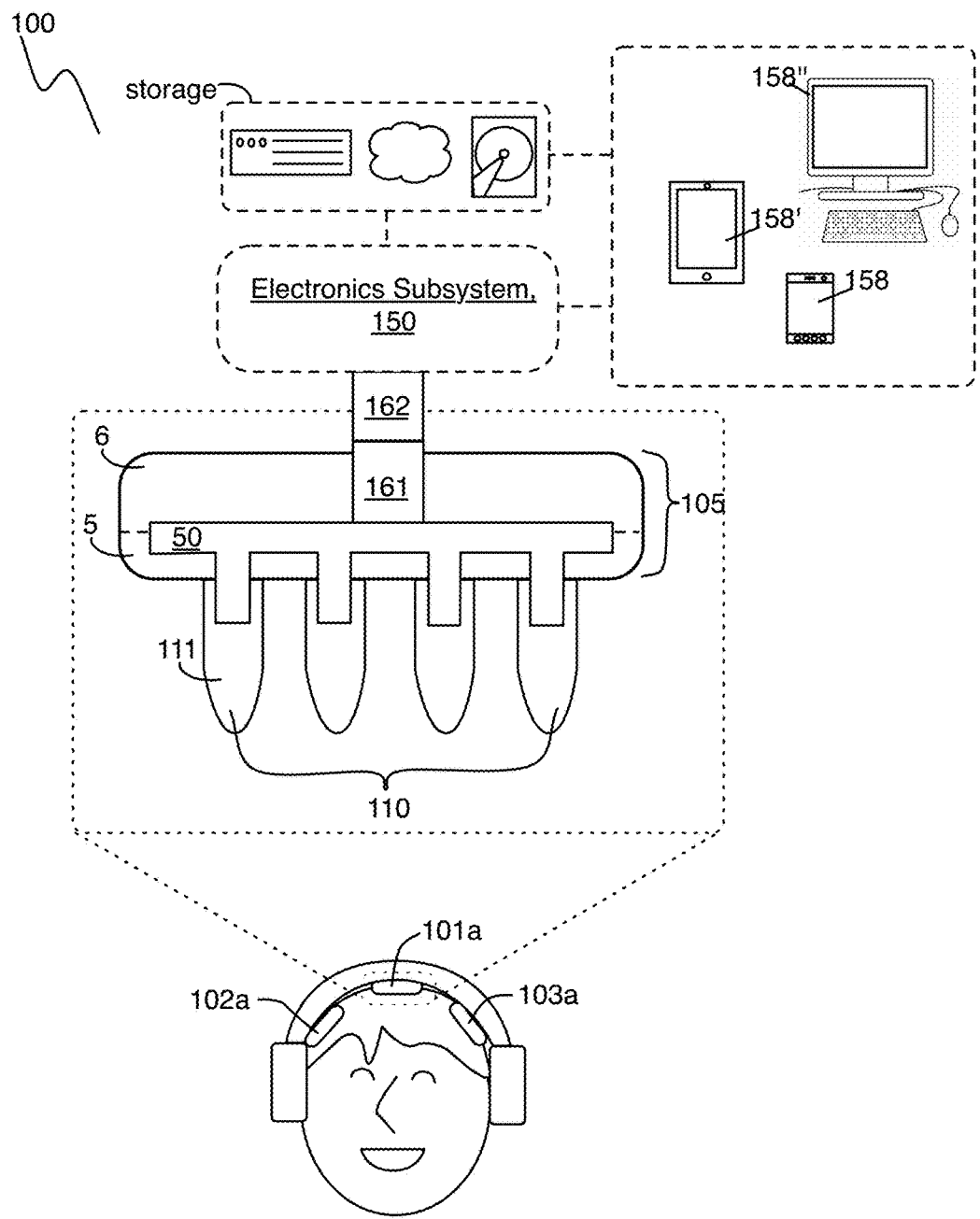
FIGS. 1A and 1B depict schematics of an embodiment of a system for providing electrical stimulation to a user.
Figure 1B:
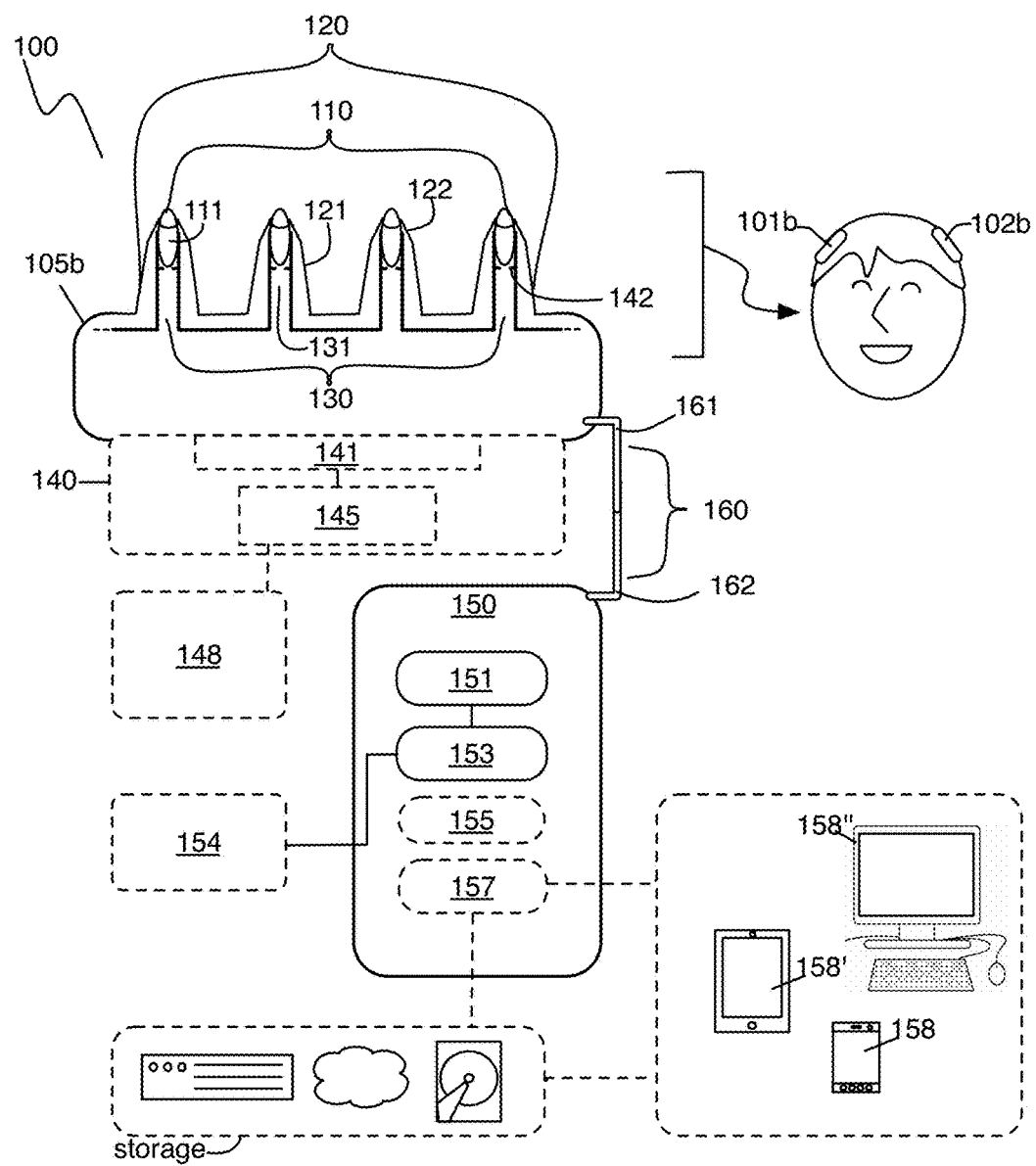

As shown in FIGS. 1A and 1B, embodiments of a system 110 for providing electrical stimulation to a user comprises: an array of permeable bodies 110 configured to absorb and deliver a solution that facilitates electrical coupling between the system and a body region of the user; a housing 105 supporting the array of permeable bodies; an electronics subsystem 150 configured to transmit stimulation to a body region of the user by way of the array of permeable bodies; and a coupling subsystem 160 comprising a first electrical coupling region 161 in electrical communication with the array of permeable bodies at an interior portion of the housing and a second electrical coupling region 162, configured to couple the first electrical coupling region to the electronics subsystem. In some variations, the system 100 can, however, omit one or more aspects of the electronics subsystem 150 described below.

The system 100 functions to transmit electrical stimulation to a user and can additionally or alternatively function to detect biosignals from the user by providing a robust connection between the user and a set of electrode contacts. Furthermore, the system 100 preferably functions to interface directly with the user in a non-invasive manner in order to transmit an electrical stimulus and/or detect a biosignal (e.g., passive signal, induced response) from the user. However, the electrode system 100 can alternatively interface with the user in an invasive manner (e.g., by including elements configured to penetrate skin of the user).

In embodiments, the system 100 can be configured to transmit electrical stimulation of a single form or of multiple forms. As such, in some examples, the system 100 can be configured to transmit one or more of: transcranial electrical stimulation (TES) in the form of transcranial direct current stimulation (tDCS), transcranial alternating current stimulation (tACS), transcranial magnetic stimulation (TMS), transcranial random noise stimulation (tRNS, e.g., band-limited random noise stimulation), transcranial variable frequency stimulation (tVFS), band-limited stimulation transformed to increase RMS power while minimizing transients and clipping (embodiments, variations, and examples of which are described in U.S. App. No. 62/127,708), and any other suitable form of TES. Furthermore, in any of the above examples and variations, the system 100 can be configured to deliver stimulation as anodal stimulation and/or cathodal stimulation. In other examples, the electrical stimulation can additionally or alternatively comprise any other form of electrical stimulation configured to stimulate any other suitable region of the user's body, with any suitable penetration depth, and/or any suitable tissue structure (e.g., neural, musculoskeletal). Furthermore, for some types of stimulation (e.g., tACS) that use biphasic waveforms (i.e., waveforms having phases of both positive and negative polarity, whether these phases are symmetrical or not), the electrodes may not strictly be characterized as anodes or cathodes but, rather, act as both at various times over the duration of stimulation; thus, the description of electrodes herein as cathodes or anodes is not intended to limit the application of the system 100 to forms of stimulation where the electrodes may be strictly characterized.

In some variations, robust connection with the user provided by the elements (e.g., mechanical aspects) of system 100 additionally or alternatively apply to transmission of non-electrical modes of stimulation. As such, the system 100 can additionally or alternatively be configured to transmit non-electrical modes of stimulation (e.g., ultrasound stimulation, optical stimulation) by using any appropriate transducer or set of transducers in place of or in addition to electrode contacts. For instance, one variation of the system 100 can be used to provide ultrasound transducing elements at a desired body region of the user, as facilitated by an array of protrusions configured to displace obstacles to ultrasound stimulation at the body region of the user. In this variation, ultrasound transducing elements can be configured at any suitable position along a length of a protrusion and/or at a distal end of a protrusion. Other variations can, however, be configured to incorporate any other element(s) for stimulating the user.

In some embodiments, the system 100 can additionally or alternatively be configured to detect biosignals from the user. In one example, the system 100 is configured to detect electroencephalograph (EEG) signals, which can be reflective of a cognitive state of the user. In other examples, the bioelectrical signals can additionally or alternatively include any one or more of: magnetoencephalograph (MEG) signals, galvanic skin response (GSR) signals, electrooculograph (EOG) signals, electromyelograph (EMG) signals, and any other suitable biosignal of the user. Other variations of the system 100 can be configured to detect any other suitable signal from the user, such as optical signals related to blood flow.

1.1 System—Electrode Contact Assembly

The electrode contact assembly preferably comprises the array of permeable bodies 110 and the housing 105, which together function to facilitate generation of a reliable and robust electrical connection between the system 100 and a body region of the user. In one embodiment, the system 100 can include multiple electrode contact assemblies, wherein one or more of the electrode contact assemblies include at least one anode region and at least one cathode region. In a first specific example of this embodiment, the system 100 includes a first electrode contact assembly 101*a* configured to interface with a superior central portion of the user's motor cortex as a "central" electrode unit, and a second and third electrode contact assembly 102*a*, 103*a* configured to interface with contralateral portions of the user's motor cortex as "side" electrode units, as shown in FIG. 1A. However, variations of the first specific example can have any other suitable configuration relative to any other suitable body region of the user.

In another embodiment, the system 100 can include two electrode contact assemblies, including a first electrode contact assembly 101*b* that functions as an anode electrode and a second electrode contact assembly 102*b* that functions as a cathode electrode, wherein both the first electrode contact assembly imb and the second electrode contact assembly 102*b* are coupled to the electronics subsystem 150, as described in further detail below and shown in FIG. 1B. However, variations of the system 100 with multiple electrode contact assemblies can have any other suitable configuration of regions (i.e., across different electrode contact assemblies, across a single electrode contact assembly) configured as anodes or cathodes.

In variations of the system 100 with multiple electrode contact assemblies, one electrode contact assembly can be configured to interface with a first body region of the user and another electrode contact assembly can be configured to interface with a second body region of the user. Furthermore, in some variations, an electrode contact assembly can additionally or alternatively be configured with a set of regions coupled to or multiplexed to the electronics subsystem 150, such that each region in the set of regions is configured to deliver stimulation in a distinct and/or controllable manner (e.g., with a desired amount of electrical current or voltage), independent of the other regions in the set of regions. The system 100 can, however, comprise any suitable number of electrode contact assemblies arranged in any other suitable manner, some variations of which are also described below.

1.1.1 Electrode Contact Assembly—Array of Permeable Bodies

The array of permeable bodies 110 functions to absorb and deliver a solution that facilitates electrical coupling between the system and a body region of the user. The body region is preferably a head region of the user, and in a specific example, is a region defined as a portion of the scalp of the user. As such, in the specific example, the array of permeable bodies is preferably configured to facilitate generation of an electrical connection to stimulate the brain of the user, through the user's hair, scalp, and skull. However, the body region of the user can alternatively be any other suitable region of the user's body (e.g., a torso region, a region of an extremity, a region of a limb, etc.) that can be treated with electrical stimulation by way of the array of permeable bodies 110, and/or that can transmit biosignals from the user for detection by the system 100.

The array of permeable bodies 110 preferably functions as a wet electrode contact that comprises a fluid-absorbing material configured to provide an electrically conductive connection to a power source (e.g., of an electrical subsystem for providing stimulation and detecting signals). The fluid-absorbing material preferably has a uniform matrix, but can alternatively have a non-uniform matrix. Furthermore, the fluid-absorbing material preferably has a high degree of wettability (e.g., as indicated by a low contact angle, as indicated by hydrophilic behavior, etc.), but can alternatively be characterized by any suitable wettability behavior. The fluid-absorbing material is preferably composed of a polymeric material, but can additionally or alternatively be composed of any other suitable hydrophilic material. The fluid-absorbing material can also be composed of a material, such as polyethylene, that is not highly wettable in its usual state but has been made wettable by application of a surface treatment such as plasma or corona treatment, by inclusion of a surfactant (e.g., a polysorbate surfactant, such as Polysorbate-20, Polysorbate-40, etc.), and/or in any other suitable manner. Furthermore, the material of the array of permeable bodies 110 is preferably non-brittle and can preferably undergo at least some amount of elastic deformation, such that substantially each of the array of permeable bodies 110 can comply against the body of the user during use, and then elastically recover against deformation. As such the composition of the array of permeable bodies 110 preferably contributes to reusability of the electrode system 100 (e.g., for up to 10 uses, for up to 30 uses, for up to 100 uses, etc.). However, the composition of the array of permeable bodies 110 can additionally or alternatively contribute to disposability of the system (e.g., in breaking down in function once the electrode system 100 should no longer be used). For instance, the material of the array of permeable bodies 110 can be configured to controllably decompose (e.g., due to tuning porosity, due to tuning polymer chemistry, etc.) or to visibly change (e.g., by including a material that gradually changes color after having first been exposed to air) or to visually indicate potential degradation in electrode performance (e.g., by including a material that changes color irreversibly after having reached a temperature of greater than 60 degrees Celsius) to promote disposing of a unit of the electrode system 100 once the unit should no longer be used. Also, the material of the array of permeable bodies 100 can additionally or alternatively be configured to signal when appropriate wetness is achieved (e.g., by inclusion of a material that changes color when wet). However, the material of the array of permeable bodies 110 can additionally or alternatively be configured to perform any other suitable function in relation to interfacing with the user.

In some variations, the fluid absorbing material of the array of permeable bodies 110 can comprise any one or more of: a foam material, a nonwoven or woven fiber material, a sintered porous material, a hydrogel material (e.g., silicon hydrogel, hydroxyethyl methacrylate hydrogel, polyvinyl alcohol hydrogel, sodium polyacrylate hydrogel, etc.), a hydrogel material processed (e.g., seeded, coated, layered, etc.) with conducting elements (e.g., by mixing, by template forming, by deposition, by printing, by electrospinning, etc.), natural sponge, synthetic sponge (e.g., cellulose sponge, polymer sponge), fabric (e.g., woven material), fluid-permeable material (e.g., a permeable or semipermeable membrane), and any other suitable fluid-absorbing material. In one such variation, the fluid-absorbing material can comprise a polymer material (e.g., an olefin polymer, a polypropylene-derived material, a polyethylene-derived material, etc.) processed with a solute at one stage that is extracted from the polymer matrix at a later stage to form a foam-like material of a substantially open-cell nature that can elastically recover against deformation. In specific examples of this variation, the material can have one or more of: a pore-size between 10 μm and 300 μm, a porosity between 60% and 90%, a density between 0.1 and 0.4 g/cm$^3$, a tensile strength between 200 and 2500 kPa, a percent elongation between 120% and 600%, and an ASKER-C Hardness between 7 and 55 or a Shore A harness between 45 and 60°. In particular, the material can have a pore size from 30-50 μm, a porosity from 63-65%, and a Shore A hardness from 50-55°. However, the material of examples of this variation can additionally or alternatively have any other suitable material properties.

In another variation, the fluid-absorbing material can comprise a polymer material combined with a foaming agent to form a foam-like material. In another variation, the fluid-absorbing material can comprise a fibrous (e.g. woven fibrous, nonwoven fibrous) polymer material (e.g., nylon, polyester). In yet another variation, the fluid-absorbing material can comprise sintered porous plastic material. However, in other variations, the material can be processed in any other suitable manner and/or composed of any other suitable material(s). Furthermore, variations of the permeable bodies can include permeable bodies having different regions with different material types. For instance, in one such example, a permeable body can comprise a hydrogel material partially or wholly encapsulated in a water-permeable membrane (e.g., porous polyethylene, porous textile, etc.) that allows wetting of the permeable body in, but prevents bulk escape of the hydrogel material into hair of the user. Additionally or alternatively, the hydrogel material can be processed with a binding agent (e.g., polyvinyl acetate, ethylene vinyl acetate) that allows the hydrogel to retain a certain desired morphology. Thus, the fluid absorbing material preferably provides a wet contact point and prevents escape of the solution for electrical coupling in an uncontrolled manner (e.g., as indicated by fluid leaking).

In some variations, the fluid-absorbing material of the array of permeable bodies 110 can be configured to undergo a morphological and/or geometric change upon fluid absorption. In one such example, the fluid-absorbing material can be compression-dried or vacuum-dried and provided in a dry, compressed state, allowing a permeable body iii of the array of permeable bodies 110 to be in a compressed state during application of the electrode system 100 to a user, and can be expanded upon fluid absorption in a wet configuration, thereby facilitating electrical coupling with the user, providing greater electrode-to-tissue contact area and/or a decrease in an electrical resistance of an electrode-to-tissue interface, and/or enabling displacement of a barrier (e.g., hair) to electrical coupling. In another such example, the fluid-absorbing material can be a shape memory material that undergoes a morphological change (e.g., a reversible morphological change, or an irreversible morphological change) in transitioning between wet and dry states. In yet another example, the fluid-absorbing material can undergo non-uniform expansion upon transitioning from a dry to a wet state (e.g., by spatial distribution of pores, by size-distribution of pores, by shape memory behavior, etc.).

In the above variations and examples, the fluid absorbed by the fluid-absorbing material can comprise saline, an electrolyte solution, an electrode gel, water, or any other suitable fluid that facilitates electrical coupling between the array of permeable bodies 110 and the user. Furthermore, the fluid can be used to facilitate administration of invasive, as well as non-invasive electrical stimulation and/or detection of biosignals from the user. Furthermore, the fluid-absorbing material of the array of permeable bodies 110 can be treated for any one or more of: biocompatibility (e.g., with a hypoallergenic agent), reusability (e.g., with an antibacterial agent or with an antimycotic agent), non-reusability (e.g., with an agent that promotes degradation in function of the fluid-absorbing material), sterilization, and any other suitable attribute. In any of the above treatments, the treatment(s) can be performed prior to, during, and/or after usage of the array of permeable bodies 110 by the user. Furthermore, the fluid can contain an agent (e.g., lidocaine hydrochloride) suitable for iontophoretic delivery to the tissue, or the material of the array of permeable bodies 110 can be treated with an agent suitable for iontophoresis such that the agent is eluted from the permeable bodies 110 and caused to pass into the tissue by electrical current. In this variation, the agent can be chosen to perform a therapeutic function related to delivery of electrical stimulation (e.g. reduction of undesired skin sensation associated with electrical stimulation), or any other desired therapeutic function.

In one embodiment, the array of permeable bodies 110 can be processed (e.g., impregnated) with electrolyte; for example, by treating with an electrolyte solution (e.g., an electrolyte solution such as 0.9% saline solution) and then transitioning to a dried state with electrolyte distributed throughout. Then, prior to use, the user or another entity can treat the array of permeable bodies 110 with water (e.g., by spraying, by dipping, etc.), thereby transitioning the array of permeable bodies 110 to a wet state with appropriate characteristics (e.g., in relation to impedance), for stimulation of the user. However, the array of permeable bodies 110 can be configured to be transitioned between any other suitable state(s) and/or processed in any other suitable manner for use by the user.

Figure 2A:
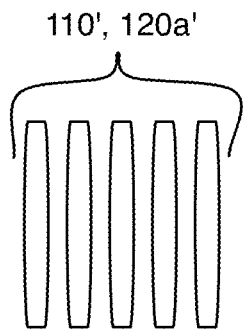
FIGS. 2A-2C depict variations of an array of permeable bodies in an embodiment of a system for providing electrical stimulation to a user.

The array of permeable bodies 110 is preferably arranged in a patterned array, in coordination with features of the housing 105, as described below; however, the array of permeable bodies 110 can alternatively be arranged in a non-patterned (e.g., irregular) array, in coordination with features of the housing 105. In one variation, as shown in FIG. 2A, the array of permeable bodies 110' is arranged as a one-dimensional array, wherein each permeable body 111 in the array of permeable bodies 110 is spaced apart from an adjacent permeable body by a space. The one-dimensional array can define a linear pattern or a non-linear pattern, and can additionally or alternatively comprise curved portions. Furthermore, upon absorption of fluid, a permeable body in of the array of permeable bodies can be configured to contact an adjacent permeable body (e.g., due to expansion upon fluid absorption), or can be configured to maintain a desired spacing with an adjacent permeable body.

Figure 2B:
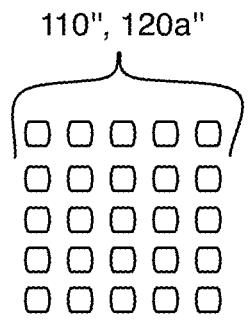
Figure 2C:
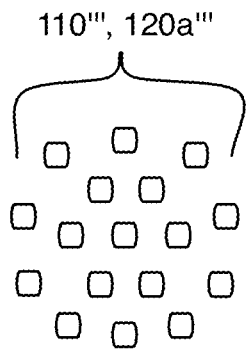

In another variation, the array of permeable bodies 110" is arranged as a two-dimensional array, wherein each permeable body 111 in the array of permeable bodies 110 is spaced apart from an adjacent permeable body by a space. The two-dimensional array can define any one or more of: a rectangular pattern, a polygonal pattern, a circular pattern, an ellipsoidal pattern, an amorphous pattern, and any other suitable pattern. Furthermore, upon absorption of fluid, a permeable body in of the array of permeable bodies can be configured to contact an adjacent permeable body (e.g., due to expansion upon fluid absorption), or can be configured to maintain a desired spacing with an adjacent permeable body. In one example of this variation, as shown in FIG. 2B, the array of permeable bodies 110" can be arranged as a rectangular grid, in another example of this variation, as shown in FIG. 2C, the array of permeable bodies 110'" can be arranged as a series of concentric circles, and in yet another example of this variation, the array of permeable bodies 110 can be arranged in a closest packed array (e.g., hexagonal closest packed array).

Figure 3A:
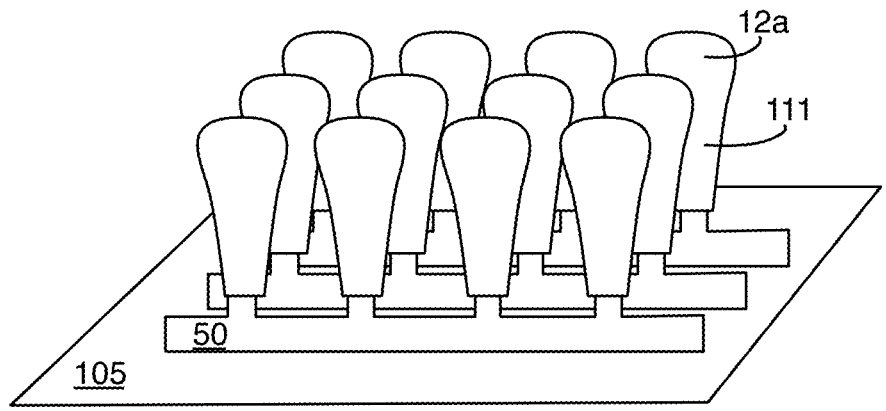
FIGS. 3A-3C depict variations of a portion of an embodiment of a system for providing electrical stimulation to a user.

Each permeable body 111 in the array of permeable bodies 110 can have a substantially uniform cross section along a length or height of the permeable body 111, or can alternatively have a non-uniform cross section. A non-uniform cross section, such as a cross-section providing a tapered tip region of the permeable body 111 can, for instance, facilitate penetration through hair of the user to promote formation of a robust electrode-user interface. In examples, the cross-section of a permeable body transverse to a longitudinal axis of the permeable body 111 can be polygonal (e.g., rectangular, triangular, etc.) or non-polygonal (e.g., circular, ellipsoidal, amorphous, etc.). Furthermore, in examples, the cross-section of a permeable body along a longitudinal axis of the permeable body 111 can be tapered to facilitate communication with a body region of the user, can be non-tapered, or can have any other suitable shape. Alternatively, a broad cross-section providing a blunted tip region 12a of the permeable body 111, an example of which is shown in FIG. 3A, can facilitate displacement of hair of the user while resisting bending at the tip of the permeable body 111, enhancing comfort when the tip is in contact with the user, and/or enhancing the appearance of the permeable bodies. Furthermore, in this example, a narrow base region of the permeable body 111 can promote localized bending at the base region, to increase contact between more distal portions of the permeable body in and the body region of the user. Furthermore, a wide base region of the permeable body 111 tapering to a narrow tip region of the permeable body 111 can promote smooth bending (as opposed to buckling) of the permeable body 111 when in contact with the body region of the user.

Figure 3B:
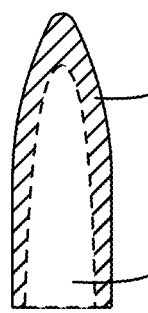
Figure 3B:
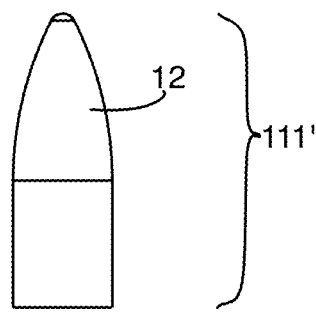

In a first variation, as shown in FIGS. 1A and 3B, a permeable body 111' of the array of permeable bodies 110 can have a circular cross section transverse to a longitudinal axis of the permeable body 111', and a tapered cross section defining a blunt tip region parallel to a longitudinal axis of the permeable body 111'. As such, in the first variation, the permeable body 111' can have a tapered distal portion 12 that facilitates electrical coupling with scalp through hair of the user. In the first variation, the permeable body 111' further can have a cavity 11 at a proximal portion configured to be supported by a substrate region 50 of the electrode contact assembly, described in further detail below. Alternative variations of the first variation can, however, omit a cavity 11 and be supported by the substrate region 50 of the system 100 in any other suitable manner. In an example of the first variation, as shown in FIG. 3B, a permeable body 111' has a height of 12.75 mm, a cross-sectional diameter of 4.3 mm at a proximal end of the permeable body 111'. In the example, the permeable body 111' has a tapered distal portion 12 beginning 5.50 mm from the proximal end of the permeable body 111', which terminates at a blunted tip region with a diameter of 1.00 mm. The specific example further has an internal cavity 11 with a depth of 10.50 mm from the proximal portion of the permeable body 111', with a cross-sectional diameter of 2.40 mm that tapers along the longitudinal axis, beginning 3.50 mm from the proximal end of the permeable body 111'. However, variations of the specific example of the first variation can alternatively have any other suitable dimensions. In another specific example, the cross section of the permeable body 111 is rectangular with a height of approximately 5 mm and a width of approximately 2 mm, wherein the permeable body in has a length of approximately 45 mm. In another specific example, the cross section of a permeable body 111 is square with a width of approximately 2 mm and a length of approximately 2 mm, wherein the permeable body in has a height of approximately 15 mm.

As such, one or more permeable bodies in the array of permeable bodies 110 can have a cross section that is non-uniform along a length or height of the permeable body in, wherein the cross section is polygonal, ellipsoidal, or of any other suitable morphology. Furthermore, a permeable body 111 in the array of permeable bodies 110 can additionally be characterized by any suitable concavity (e.g., convex surface, concave surface) at a distal end of the permeable body 111 (e.g., an end of the permeable body interfacing with the user) in order to facilitate bypassing and/or penetration of a barrier to electrical coupling. The array of permeable bodies 110 furthermore preferably span a footprint having an area below 40 cm$^2$ in order to provide stimulation to a gyrus or similarly-sized region of the brain; however, the array of permeable bodies 110 can alternatively span any other suitable footprint. In one example, a distal end of a permeable body 111 can have a convex surface (e.g., upon fluid absorption, or prior to fluid absorption), in order to facilitate passage of the permeable body 111 through a user's hair, and to increase a surface area of electrode-to-skin contact when the system 100 is held firmly against the user's skin. Furthermore, in examples, the array of permeable bodies can span a footprint having an area of 4.4 cm×6.4 cm to provide an area of stimulation of approximately 30 cm$^2$.

Figure 3C:
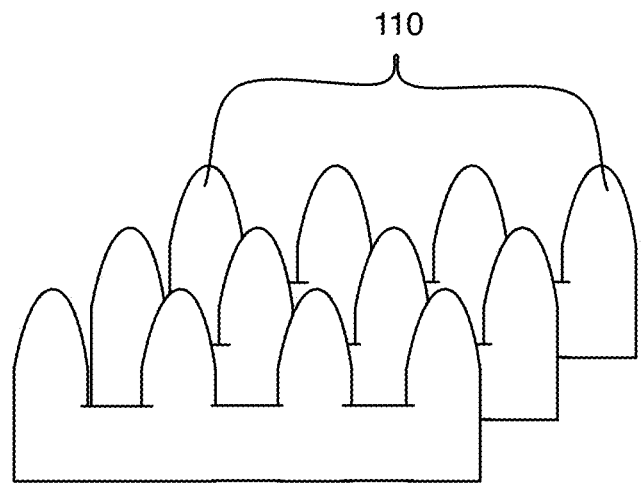

In some variations, two or more of the array of permeable bodies 110 can be coupled together in some manner (e.g., physically coextensive, of unitary construction), for instance, to facilitate manufacturing of the system 100. In one such variation, a subarray (e.g., row of bodies, column of bodies, one of a set of concentric ring of bodies, etc.) of the array of permeable bodies 110 can be coupled at proximal regions (i.e., base regions) of the permeable bodies, as shown in FIG. 3C, such that the array of permeable bodies 110 is configured as multiple subarrays of conjoined permeable bodies, as opposed to individual/separated permeable bodies. Furthermore, the configuration of subarrays of the array of permeable bodies 110 can correspond to anode and/or cathode regions associated with the substrate region 50 of the system 100 and/or the electronics subsystem 150 of the system 100, as described in further detail below.

In some variations, one or more of the array of permeable bodies 110, and/or a region of a permeable body 111 can be substituted with or supplemented with another suitable conductive material. In one such example, a core region of a permeable body 111 can comprise a substantially non-fluid absorbing conductive material, which is surrounded by fluid absorbing material. Variations of the core region are further described below, in relation to the substrate region 50 included in some embodiments of the system 100. In variations, a non-fluid absorbing conductive material can comprise any one or more of: a metal (e.g., gold, steel, platinum), a metal alloy (e.g., gold alloy, platinum alloy), a semiconductor (e.g., doped silicon, a carbon-based semiconductor), a conductive polymer (e.g., polyacetylene, polyphenylene vinylene, polythiophene, polyaniline, polyphenylene sulfide, polypyrrole), and any other suitable conductive material. Such conductive materials can be configured to provide or facilitate electrical conductivity without necessitating a solution (e.g., saline, electrolyte solution) for conduction; however, the conductive material can additionally be used with a solution or gel, in order to facilitate electrical coupling.

Figure 4A:
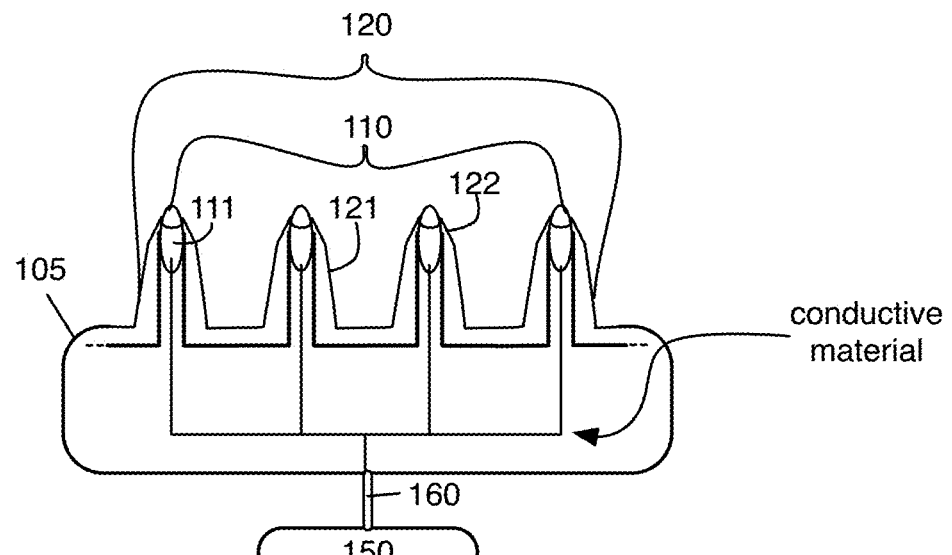
FIG. 4A depicts a variation of a system for providing electrical stimulation to a user.

In one such variation, as shown in FIG. 4A, a conductive material (e.g., metal conductor formed into wires, conductor formed into conductive traces) can be configured to provide electrical coupling between the electronics subsystem 150 and an array of permeable bodies 110 (e.g., an array of permeable bodies comprising a hydrogel material permeated with a conductive liquid or solution) situated at distal ends of an array of protrusions 120, wherein the conductive material is directly coupled to the material of the array of permeable bodies 110, without relying on the conductive liquid or solution, provided by a manifold 140, to carry electrical current proximal to the array of permeable bodies 110. In examples of this variation, the conductive material can travel along an internal and/or an external portion of the housing 105 to electrically communicate with permeable bodies positioned at distal portions of the array of protrusions (e.g., as described in further detail below in relation to the substrate region so), in order to provide electrical coupling between the array of permeable bodies 110 and the electronics subsystem 150 of the system 100. As such, some variations of the system 100 can omit a manifold 140 and provide direct coupling between permeable bodies of an array of protrusions and the electronics subsystem 150 using one or more conductive materials.

In one example of this variation, the system 100 can include an array of conductive traces coupled between the electronics subsystem 150 and each of the array of permeable bodies 110 (e.g., by way of the coupling subsystem 160, wherein each of the array of permeable bodies 110 is permeated (e.g., pre-saturated) or is configured to be permeated (e.g., via the user applying fluid to the permeable bodies before use) with an electrical coupling fluid configured to facilitate transmission of the electrical stimulation treatment to the user. In the example, each conductive trace is paired with a permeable body in a one-to-one manner; however, variations of the example can include coupling between the array of permeable bodies and the array of conductive traces in a less-than-one-to-one or a more-than-one-to-one manner. In more detail, in a specific example the conductive material can comprise an elastomeric material (e.g., molded silicone rubber elastomer) containing or otherwise doped with a conductive substance (e.g., carbon black particles). Such a composition can function to control electrochemical reaction products that would otherwise result with use of other materials (e.g., metal) for the junction between "electronic" conduction and "ionic" conduction. Furthermore, such a composition can be readily configured to conform morphologically with the morphology of the array of permeable bodies 110, as described in more detail below. Additionally, elastic properties of this material composition can facilitate a press-fit interface against metal to ensure reliable contact. Furthermore, such a composition can ensure good, but slightly less than perfect conductivity (e.g., with volume resistivity of ~2 to 50 Ohm-cm), which can provide a desired amount of current distribution. In more detail, if the path to each of the array of permeable bodies 110 has some resistance (e.g., a low amount of resistance in comparison to the tissue resistance), it is more likely that each of the array of permeable bodies 110 will receive some current even in the presence of variation in quality of contact between the permeable bodies and the user. However, any other suitable material (e.g., metallic conductor, rubber doped with metal, etc.) can be used, and the array of permeable bodies 110 can alternatively be configured to couple to the electronics subsystem 150 in any other suitable manner.

1.1.2 Electrode Contact Assembly—First Embodiment of the Housing and Array of Protrusions of the Substrate Region The housing 105 functions to convey the array of permeable bodies 110 to the body region of the user and to facilitate electrical coupling between the electronics subsystem 150 (described in more detail below) and the body region of the user. In one embodiment, as shown in FIGS. 1A and 5A-5D, the housing 105a can include a first housing portion 5 and a second housing portion 6, however, some variations of this embodiment housing 105 can additionally or alternatively omit either portion of the housing 105. For instance, in one such variation of this embodiment of the housing 105, the housing 105 can only include a second housing portion 6 that supports the substrate region 50 and array of permeable bodies 110. The first housing portion 5 in this embodiment preferably defines an array of openings 7 at a broad surface 8, wherein the array of openings 7 exposes distal portions of the array of permeable bodies 110 for interfacing with the body region of the user during use. The broad surface 8 of the first housing portion 5 is preferably a non-planar surface that is complementary to the body region of the user intended to be stimulated by the system 100; however, the broad surface 8 can alternatively be a planar surface (or any other suitable surface), such that at least one of 1) the broad surface 8 of the first housing portion 5 and, 2) collectively, distal portions of the array of permeable bodies 110 define a surface that is complementary to the body region of the user during use of the system 100.

Figure 5A:
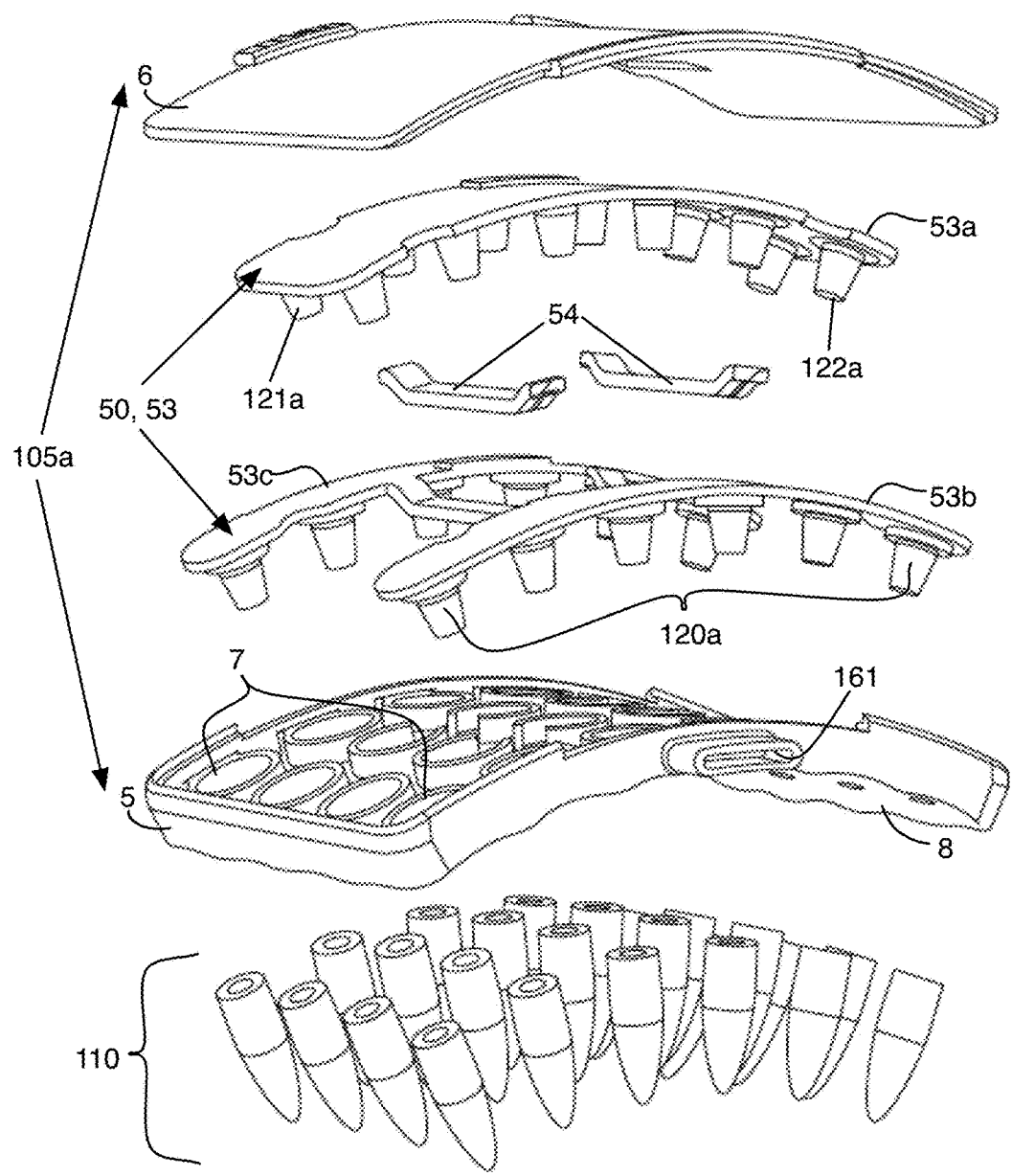
FIGS. 5A-5E depict variations of an embodiment of a system for providing electrical stimulation to a user.

The second housing portion 6 is preferably configured to couple to the first housing portion 5 to define a volume within which the substrate region 50 and the set of conductors 60 of the coupling subsystem 160 (described in more detail below) are sealed or otherwise protected from damage. In particular, as shown in FIG. 5A, portions of the substrate region 50 that interface with pads 62 (described in more detail below) can serve as the set of conductors 60. Furthermore, as described in more detail below, at least one of the first housing portion 5 and the second housing portion 6 can function to facilitate electromechanical coupling of conductive portions of the substrate region 50 and/or the set of conductors 60 to the electronics subsystem 150, for transmission of electrical stimulation through the array of permeable bodies 110 to the user.

The housing 105a is preferably composed of a rigid material (e.g., a rigid plastic material, etc.), such that the housing 105a does not deform in response to normal forces, shear stresses, bending stresses, or torsional stresses induced during use of the system 100. Alternatively, the housing 105a can be flexible to facilitate maintenance of compliance with a body region of the user (e.g., as the user performs a physical activity while the system 100 is coupled to the user). In variations wherein the housing 105a is flexible, other elements of the system 100 can also be flexible (e.g., the electronics subsystem 150 can comprise a flexible thin film battery, the electronics subsystem 150 can comprise flexible electronics, the electronics substrate 64 can comprise a flexible printed circuit board, etc.) to facilitate compliance with the body region of the user. In specific examples, the housing 105a can be composed of one or more of: a polycarbonate-derived material, an acyrlonitrile butadiene styrene (ABS)-derived material, and any other suitable material.

The housing 105a preferably has a profile that does not protrude a significant distance from the body region of the user when the user is being stimulated by the system 100. As such, the housing 105a preferably has a low aspect ratio that contributes to a thin form factor of the system 100. However, the housing 105a can alternatively define a volume with a high aspect ratio. Preferably, the external surface of the housing 105a is substantially smooth and has rounded edges, in order to avoid discomforting or injuring the user as the user interfaces with the system 100.

Furthermore, the housing 105a can define a substantially polygonal footprint (i.e., a quadrilateral footprint, a triangular footprint, a pentagonal footprint, a hexagonal footprint, etc.), or can alternatively define one or more of a circular footprint, an ellipsoidal footprint, and an amorphous footprint. In one example, as shown in FIG. 5A, the housing 105a defines a rectangular footprint and has a thickness substantially below 2 cm, a length below 15 cm, and a width below 10 cm, in order to produce a form factor with a low aspect ratio and sufficient surface area to facilitate stimulation of the user. Variations of the example of the housing 105a can, however, be configured in any other suitable manner.

As described briefly above, the housing 105a preferably forms a shell about its internal components, and preferably has a first housing portion 5 facing the body region of the user when the system 100 interfaces with the user and a second housing portion 6 facing away from the body region of the user when the system 100 interfaces with the user. The first housing portion 5 and the second housing portion 6 can be coupled together (e.g., using a hermetic sealing element) using one or more of: a snap fit, a mechanical press fit, a thermal bond, an adhesive, a compliant sealing material (e.g., putty), an o-ring, an x-ring, any other suitable ring, and/or any other suitable sealing element. As such, an interface between the first housing portion 5 and the second housing portion 6 can be configured to be waterproof in order to protect elements internal to the housing 105a, and/or can be configured to protect internal elements of the housing 105a in any other suitable manner. Alternatively, an interface between the first housing portion 5 and the second housing portion 6 can be configured to not be waterproof and, as stated above, some variations of this embodiment of the housing 105 can omit the first housing portion 5.

As described briefly above, the housing 105a preferably has an array of openings 7 defined at the first housing portion 5, wherein the array of openings 7 exposes distal portions of the array of permeable bodies 110 for interfacing with the body region of the user during use. Preferably, the array of openings 7 is defined entirely at the first housing portion 5;

however, in alternative variations, the array of openings 7 can be defined at both the first housing portion 5 and the second housing portion 6, or at only the second housing portion 6. The array of openings 7 can be a rectangular array of openings 7; however, the array of openings 7 can alternatively be configured in any other suitable manner (e.g., as a circular array of openings, as an ellipsoidal array of openings, as a polygonal array of openings, as an amorphous array of openings, etc.). Each opening in the array of openings 7 is also preferably a circular opening, but can alternatively be a non-circular opening (e.g., in complementing an external surface of a permeable body of the array of permeable bodies). Furthermore, each opening in the array of openings 7 is preferably identical to every other opening in the array of openings 7 in morphology; however, the array of openings 7 can alternatively comprise non-identical openings. In a specific example, as shown in FIGS. 5A-5D the array of openings 7 includes 24 identical circular openings arranged in a 4×6 rectangular array, each opening having a diameter of 4.30 mm and an inter-opening spacing of that prevents contact between adjacent permeable bodies in their undeformed state and minimizes overlap between adjacent permeable bodies when they are deformed in contact with the user; however, variations of the specific example of the array of openings 7 can be configured in any other suitable array.

Figure 5B:
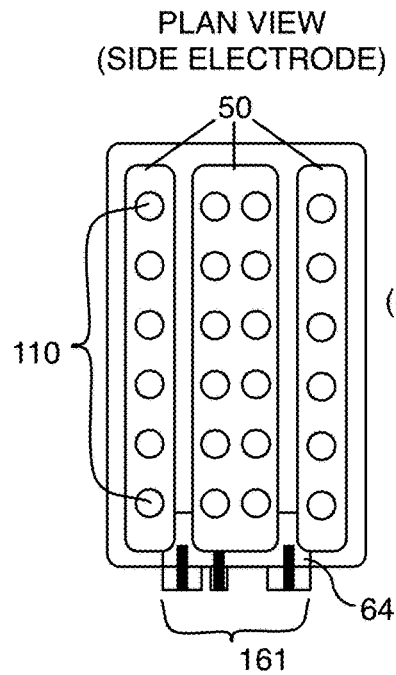
Figure 5C:
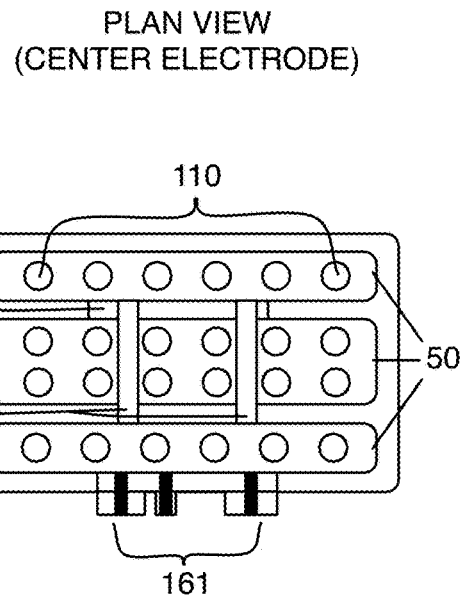
Figure 5D:
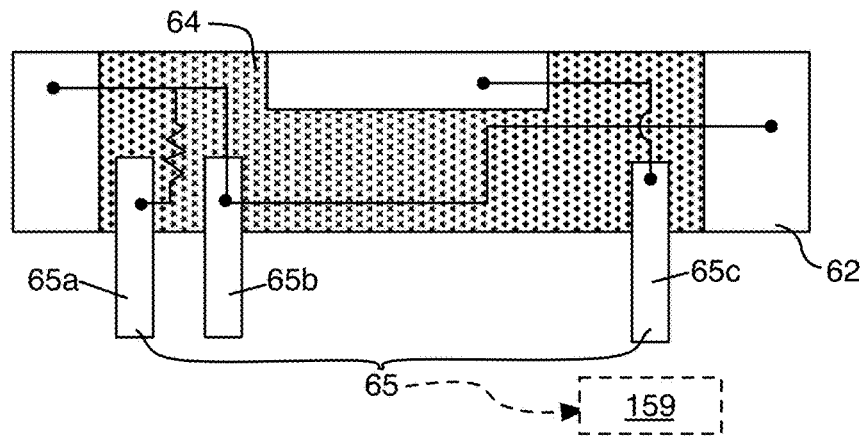
Figure 5E:
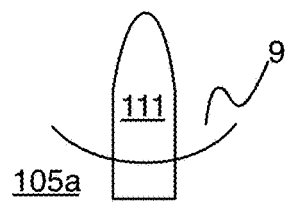

In some variations, as shown in FIG. 5E, a base region 9 of each opening of the array of openings 7 of the housing 105a can be recessed at the broad surface 8 facing the user, in order to facilitate retention of excess fluid at the housing 105a, in a controlled manner, during use of the system 100 by the user. For instance, in example scenarios where the user dips the array of permeable bodies 110 in water prior to use, or sprays the array of permeable bodies 110 with water prior to use, recesses at the base regions 9 of the array of openings 7 of the housing can help guide fluid to and/or retain fluid proximal the array of permeable bodies 110, such that they are properly saturated prior to use by a user. In one variation, the base region 9 of each opening of the array of openings 7 of the housing 105a can be concave, and in a specific example, the base region 9 of each opening can be a concentric bowl about its corresponding opening. In alternative variations, the recessed base region 9 can have any other suitable morphology (e.g., conical, pyramidal, stepwise, etc.).

Additionally or alternatively, portions of the base regions 9 of one or more openings of the array of openings 7 can additionally or alternatively protrude from (e.g., have a convex portion at) the housing 105, in order to support proximal portions of the array of permeable bodies 110. For instance, a protruding base region 9 can provide additional mechanical support to a permeable body 111, thereby providing a bending constraint at the base region 9.

While one embodiment of the housing 105a of the system 100 is described above, alternative embodiments of the housing 105a can be configured in any other suitable manner, one such embodiment of which is described below in Section 1.1.3.

As shown in FIGS. 1A and 5A, the first embodiment of the housing 105a preferably supports a substrate region 50, which functions to conduct current for electrically stimulating the user, to the array of permeable bodies 110. The substrate region 50 is thus preferably composed of a conductive material (e.g., metal, semiconductor, polymer, etc.); however, the substrate region 50 can additionally or alternatively be composed of an insulating material with conductive traces that transmit current from the electronics subsystem 150 through the conductive traces of the substrate region 50 to the array of permeable bodies 110, or a material such as silicone rubber that is not intrinsically conductive but is made conductive by inclusion of a conductive material such as carbon. The substrate region 50 can have some flexibility in relation to supporting the array of permeable bodies 110, such that the array of permeable bodies 110 can flex, with at least a portion of the substrate region 50, to conform to the body region of the user. However, the substrate region 50 can alternatively exhibit a higher degree of rigidity in supporting the array of permeable bodies 110. In one variation, the substrate region 50 is composed of a conductive polymer composition (e.g., polypyrrole, non-conductive polymer with a distribution of conductive components, silicone rubber made conductive by inclusion of carbon, etc.) that supports the array of permeable bodies 110. However, the substrate region 50 can alternatively be composed of a non-polymeric material.

In supporting the array of permeable bodies 110, the substrate region 50 is preferably coupled to the array of permeable bodies 110, such that the substrate region 50 is in physical communication with the array of permeable bodies 110 and thus, in electrical communication with an electrolyte solution absorbed by or contained within the array of permeable bodies 110. In coupling to the array of permeable bodies 110, the substrate region 50 can be removably coupled or alternatively, permanently coupled to the array of permeable bodies 110 using one or more of: an adhesive coupling mechanism, a mechanical coupling mechanism, a thermal coupling mechanism, a magnetic coupling mechanism, and any other suitable coupling mechanism. In one such variation, as shown in FIG. 5A, the substrate region 50 can define an array of protrusions 120a that support the array of permeable bodies 110. In more detail, and in relation to a variation of the array of permeable bodies 110 described in Section 1.1.1 above, the array of protrusions 120a can correspond to and be configured to reside within cavities 11 of the array of permeable bodies 110, such that each permeable body forms a sleeve around a corresponding protrusion of the array of protrusions 120a. However, the array of protrusions 120a of the substrate region 50 can additionally or alternatively cooperate with the array of permeable bodies 110 in any other suitable manner, such that the array of protrusions 120a corresponds to and supports the array of permeable bodies 110.

In more detail, the array of protrusions 120a can function, with the array of permeable bodies, to facilitate bypassing and/or penetration of barriers to electrical coupling, such that the system 100 can robustly interface with a body region of the user. Preferably, the array of protrusions 120a is configured to bypass the user's body hair; however, the array of protrusions can additionally or alternatively be configured to facilitate bypassing or penetration of any other barrier to electrical coupling (e.g., clothing, fur). The array of protrusions 120a is preferably configured to not penetrate the user's body, such that the system 100 is substantially non-invasive; however, the array of protrusions 120a can alternatively be geometrically configured to penetrate or abrade the stratum corneum of the user and/or any underlying tissue structure, such that the system 100 is configured to be invasive or minimally invasive. The array of protrusions 120a, in cooperation with the array of permeable bodies 110 preferably provides a region of contact between a body region of the user and the system 100, in order to facilitate electrical coupling. Furthermore, each protrusion 121a in the array of protrusions 120 is preferably associated with a permeable body in of the array of permeable bodies 110 in a one-to-one manner; however, the array of protrusions 120 and the array of permeable bodies 110 can alternatively be associated in a many-to-one manner or a less-than-one-to-one manner.

The array of protrusions 120a, in its entirety, is thus preferably geometrically configured to bypass or penetrate a barrier, for example, by spatial arrangement and/or distribution of protrusions 121a in the array of protrusions 120a. Similar to the array of permeable bodies 110, in one variation, the array of protrusions 120a' can be a linear array, in a manner analogous to the example shown in FIG. 2A, or can be a multi-dimensional array of protrusions 120a", 120a'" in manners analogous to examples shown in FIGS. 2B and 2C. All protrusions in the array of protrusions 120a can additionally be substantially identical to each other, or can be non-identical to each other in order to facilitate conformation to the user and/or to provide robust electrical coupling. For example, the protrusions in the array of protrusions 120a can be characterized by one or more of: different heights, different widths, different diameters, different cross-sectional profiles, different material compositions, different mechanical behavior, different electrical behavior, any other suitable property difference, and any suitable combination of property differences. Preferably, the height of each protrusion in the array of protrusions 120a is greater than the thickness of the barrier (e.g., a user's hair) during application of the system 100 to the user. However, in other variations, only a subset of protrusions in the array of protrusions 120a can have a height greater than the thickness of a barrier to electrical coupling, or no protrusion in the array of protrusions 120a is characterized by a height greater than the thickness of a barrier to electrical coupling. Furthermore, the array of protrusions 120a can be configured to define a non-continuous surface that forms a complementary surface to a surface of the user, by comprising protrusions of varying or variable lengths. Alternatively, and similar to the housing 105a, the array of protrusions 120a can be arranged at a non-planar surface of the substrate region 50 in order to complement a surface of the body region of the user. In one example, the array of protrusions 120a can be configured, with a non-planar surface of the substrate region 50, to define a concave surface that is complementary to a convex surface of the user's body (e.g., skull). However, the array of protrusions 120a can alternatively collectively define any other suitable surface.

Each protrusion 121a in the array of protrusions 120a can additionally or alternatively be configured to individually facilitate barrier bypassing and/or penetration. Preferably, each protrusion 121 is geometrically configured to facilitate barrier bypassing and/or penetration; however, any protrusion in the set of protrusions no can be configured to facilitate barrier bypassing and/or penetration in any other suitable manner. In one variation, at least one protrusion 121 in the set of protrusions 120 is characterized by a cross-sectional profile tapering continuously to at least one point 122a, as shown in FIG. 5A, wherein the point(s) 122 can be blunted or shielded in order to prevent penetration of the user's body. In one example of this variation, a protrusion 121a can be configured to taper in a direction perpendicular to the scalp of the user (e.g., in a proximal-to-distal direction), upon application of the system 100 to the user, such that the point 122a of the protrusion 121a is oriented normal to the scalp of the user. As such, the protrusion(s) 121a of the array of protrusions 120a can be configured to extend laterally from the substrate region 50, an example of which is shown in FIG. 5A. In alternative variations, protrusions of the array of protrusions 120a can be configured in any suitable orientation that facilitates delivery of distal ends of the protrusions to a scalp region of the user in any other suitable manner. For instance, protrusions extending from a substrate in an angled, whorled, and/or spiraled configuration (e.g., extending in a manner that is not directly perpendicular to the substrate) can provide a mechanism whereby the protrusions "screw" into position at the user's scalp.

At least one protrusion 121a of the array of protrusions 120a can be deflectable and/or deformable (e.g., elastically, plastically) in order to further enhance electrical coupling between the system 100 and the user. In one variation, a protrusion of the array of protrusions 110 can be configured to deflect laterally (e.g., based upon morphology, based upon inclusion of a joint at a portion of the protrusion), based upon inclusion of a hinge at a portion of the protrusion), such that application of the array of protrusions 110 at the user, along with lateral deflection of a protrusion during application (e.g., by applying pressure normal to a surface of the housing 105a and/or laterally moving the housing 105a during application of the system 100 to the user), facilitates contact between the system 100 and the user. Alternatively, at least a portion of a protrusion 121a can be configured to be substantially rigid, thus allowing no deflection or deformation (with deflection enabled by other regions of the substrate region 50). As such, a protrusion 121 can be characterized by any suitable combination of variations, or any other suitable variation. Furthermore, a protrusion 121a of the array of protrusions 120a can be substantially solid, or can define a hollow region in order to facilitate electrical coupling (e.g., for providing a pathway for an electrical connection, for delivering a fluid to the protrusion to facilitate deflection and/or expansion of a permeable body).

In a specific example, as shown in FIGS. 5A-5D, the array of protrusions 120a comprises 24 protrusions arranged in a 4×6 array, corresponding to an example of the array of permeable bodies 110; however, the array of protrusions 120a can alternatively comprise any other suitable configuration.

In some variations, one of which is shown in FIG. 5A, the substrate region 50 can be separated into a set of subregions 53, in relation to variations of the system 100 wherein different subsets of the array of permeable bodies 110 are configured to have different electrical stimulation parameters (e.g., different polarities, different current levels, different impedance levels, different operational states, etc.). For instance, a first subregion 53a of the substrate region 50 can be configured to have a first polarity (e.g., to function as an anode), and a second subregion 53b of the substrate region 50 that is separated or otherwise isolated from the first subregion 53a can be configured to have a second polarity (e.g., to function as an anode), upon coupling the substrate region 50 to a set of conductors 60 of a first electrical coupling region 161 of the coupling subsystem 160 (described in further detail below). The subregions 53a, 53b can be isolated from each other using one or more of: a spacing element positioned between the subregions 53a, 53b, an insulating material element positioned between the subregions 53a, 53b, a space between element the subregions 53a, 53b, and in any other suitable manner.

In a specific example, as shown in FIG. 5A, the substrate region is divided into a first subregion 53a with a first subset of protrusions configured to have a first polarity, and a second subregion 53b and a third subregion 53c with a second subset of protrusions and a third subset of protrusions, respectively, each of the second and the third subregions 53b, 53c configured to have a second polarity. As shown in FIGS. 5A-5D, the first, the second, and the third subregions 53a, 53b, and 53c each have rectangular footprints, and the second and the third subregions 53b, 53c each flank an opposing side of the first subregion 53a. In the specific example, in the first region 53a comprises 12 protrusions arranged in a 2×6 rectangular array, and each of the second and the third subregions 53b, 53c each comprise 6 protrusions arranged in a 1×6 linear array. Furthermore, to prevent shorting of the subregions 53a, 53b, 53c, the first subregion 53a is separated from both the second subregion 53b and the third subregion 53c by a set of spacers 54 (e.g., 2 insulating spacers), such that contact between the subregions 53a, 53b, 53c is prevented. Alternatively, the spacers 54 can be substituted with any other suitable insulator (e.g., air) to prevent undesired contact between the subregions 53a, 53b, 53c. Furthermore, variations of this specific example can alternatively be arranged in any other suitable manner.

1.1.3 Electrode Contact Assembly—Second Embodiment of the Housing, Array of Protrusions, and Manifold In another embodiment, as shown in FIG. 1B, the housing 105 can define an array of protrusions 120 and comprise one or more of: an array of channels 130 distributed across the array of protrusions, each channel 131 in the array of channels surrounding a permeable body of the array of permeable bodies 110 and configured to deliver the solution to the permeable body, and a manifold 140 configured to distribute the solution to the array of channels 130. In some variations, one or more channels 131 of the housing 105b can comprise or be coupled to a barrier 142 configured to prevent passage of a permeable body 111 past the barrier in a distal-to-proximal direction (e.g., in a direction into the housing or away from the body of the user). The housing 105b thus functions to convey the array of permeable bodies 110 to the body region of the user, to facilitate distribution of fluid to the array of permeable bodies, and to facilitate electrical coupling between an electronics subsystem 150 and the body region of the user.

Figure 4B:
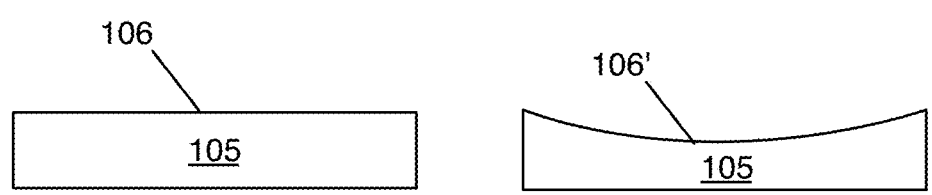
FIG. 4B depicts variations of a housing surface in an embodiment of a system for providing electrical stimulation to a user.

The housing 105b of this embodiment preferably serves as a substrate that functions to form a core or base structure to which other elements of the system 100 can be coupled and/or otherwise placed in communication (e.g., electrical communication). Preferably, the housing 105b is physically coextensive with the array of protrusions 120; however, the housing 105b can alternatively be of unitary construction with the array of protrusions 120, or can couple to the array of protrusions 120 using any suitable bonding method (e.g., thermal bonding, adhesive bonding, electrical bonding). In still other variations, the housing 105b can be configured to couple to the array of protrusions 120 in a manner that allows one or more protrusions of the array of protrusions 120 to have adjustable depths within the housing 105b (e.g., in order to be in communication with subsets of channels of the housing). In some variations, the housing 105b can be flexible, such that the array of protrusions 120 and/or the housing 105b is configured to flexibly conform to the user's body. In other variations, however, the housing can be entirely rigid, or can additionally or alternatively comprise portions that are substantially rigid. In variations wherein the housing 105b is rigid, the housing 105b can define a planar surface 106, as shown in FIG. 4B (left), configured to interface with the body region of the user, such that other elements (e.g., the array of protrusions 120) enable a configuration that conforms to the user, or the housing 105b can define a non-planar surface 106', as shown in FIG. 4B (right), that facilitates conformation of the system 100 to a body region of the user. In one such example, the housing 105b can include a concave surface 106' that is complementary to a head region of the user, such that the housing conforms to the user's head region. In still other variations, the housing 105b can be flexible in one environment and rigid in another environment (e.g., the substrate is a shape memory material), such that the housing 105b is characterized by different mechanical behavior in different environments. For example, the housing 105b can comprise a shape memory metal or polymer that is configured to be planar when the system 100 is not coupled to the user, and configured to conform to the user when the system 100 is coupled to the user. In variations wherein the housing 105b can undergo a rigid-to-flexible transition or a flexible-to-rigid transition, the transition can be reversible or non-reversible.

In variations, the housing 105b can comprise one or more of: a non-conductive material (e.g., plastic, polyethylene, ABS, polyethyl ethyl ketone, polyurethane, rubber, ceramic, etc.) and a conductive material (e.g., metal, stainless steel, etc.). However, the housing 105b can additionally or alternatively comprise any other suitable material(s).

The array of protrusions 120 functions to facilitate bypassing and/or penetration of barriers to electrical coupling, such that the system 100 can robustly interface with a body region of the user. Preferably, the array of protrusions 120 is configured to bypass the user's body hair; however, the array of protrusions can additionally or alternatively be configured to facilitate bypassing or penetration of any other barrier to electrical coupling (e.g., clothing, fur). The array of protrusions is preferably configured to not penetrate the user's body, such that the system 100 is substantially non-invasive; however, the array of protrusions can alternatively be geometrically configured to penetrate or abrade the stratum corneum of the user and/or any underlying tissue structure, such that the system 100 is configured to be invasive or minimally invasive. The array of protrusions 120, in cooperation with the array of permeable bodies 110 preferably provides a region of contact between a body region of the user and the system 100, in order to facilitate electrical coupling. Furthermore, each protrusion 121 in the array of protrusions 120 is preferably associated with a permeable body in of the array of permeable bodies 110 in a one-to-one manner; however, the array of protrusions 120 and the array of permeable bodies 110 can alternatively be associated in a many-to-one manner or a less-than-one-to-one manner. The array of protrusions 120 can be configured with an inter-protrusion spacing that facilitates delivery of a substantially uniform density of electrical current to the body region of the user during use, and in examples, an inter-protrusion spacing can be between 5 and 20 mm.

Figure 6A:
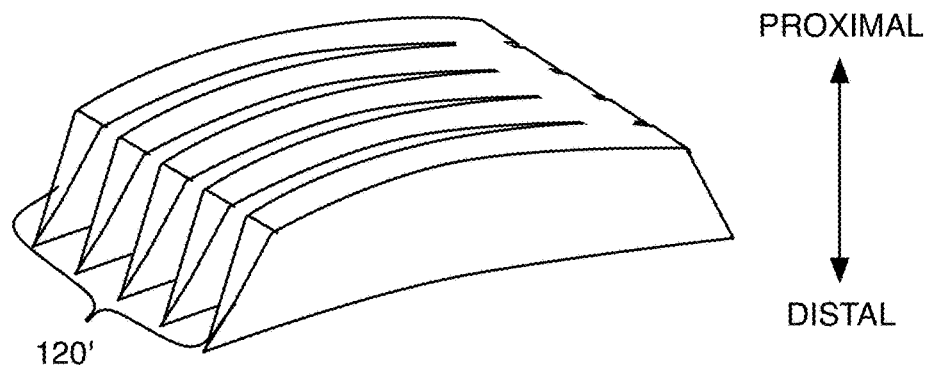
FIGS. 6A-6C depict variations of an array of protrusions in an embodiment of a system for providing electrical stimulation to a user.
Figure 6B:
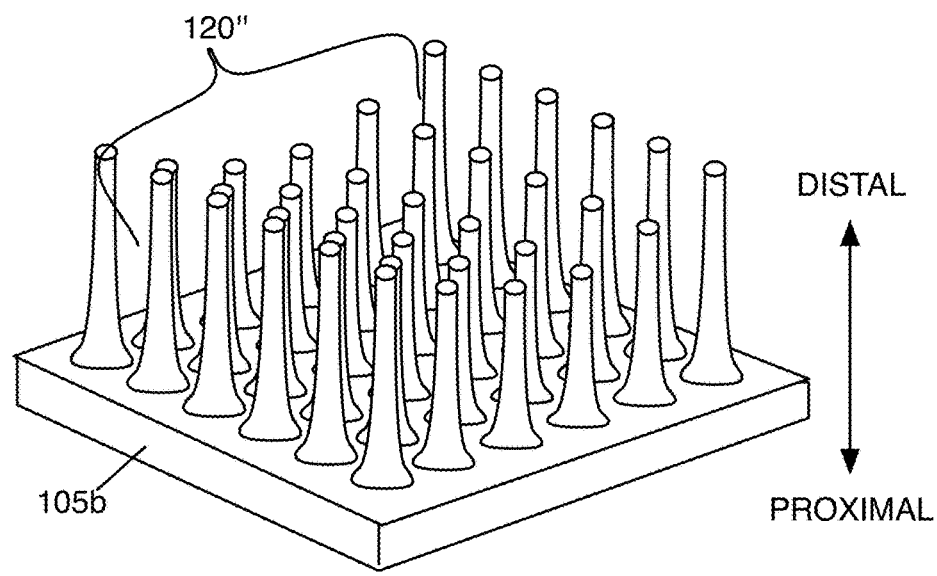

The array of protrusions 120, in its entirety, is thus preferably geometrically configured to bypass or penetrate a barrier, for example, by spatial arrangement and/or distribution of protrusions 121 in the array of protrusions 120. Similar to the array of permeable bodies 110, in one variation, the array of protrusions 120' can be a linear array, an example of which is shown in FIG. 6A, or can be a multi-dimensional array of protrusions 120", an example of which is shown in FIG. 6B. All protrusions in the array of protrusions 120 can additionally be substantially identical to each other, or can be non-identical to each other in order to facilitate conformation to the user and/or to provide robust electrical coupling. For example, the protrusions in the array of protrusions 120 can be characterized by different heights, different widths, different diameters, different cross-sectional profiles, different material compositions, different mechanical behavior, different electrical behavior, any other suitable property difference, and/or any suitable combination of property differences. Preferably, the height of each protrusion in the array of protrusions 120 is greater than the thickness of the barrier (e.g., a user's hair) during application of the system 100 to the user. However, in other variations, only a subset of protrusions in the array of protrusions 120 can have a height greater than the thickness of a barrier to electrical coupling, or no protrusion in the array of protrusions 120 is characterized by a height greater than the thickness of a barrier to electrical coupling. Furthermore, the array of protrusions 120 can be configured to define a non-continuous surface that forms a complementary surface to a surface of the user, by comprising protrusions of varying or variable lengths. In one example, the array of protrusions 110 can be configured to define a concave surface that is complementary to a convex surface of the user's body (e.g., skull).

Each protrusion 121 in the array of protrusions 120 can additionally or alternatively be configured to individually facilitate barrier bypassing and/or penetration. Preferably, each protrusion 121 is geometrically configured to facilitate barrier bypassing and/or penetration; however, any protrusion in the set of protrusions 110 can be configured to facilitate barrier bypassing and/or penetration in any other suitable manner. In one variation, at least one protrusion 121 in the set of protrusions 120 is characterized by a cross-sectional profile tapering continuously to at least one point 122, as shown in FIG. 1B, wherein the point(s) 122 can be blunted or shielded in order to prevent penetration of the user's body. In a first example of this variation, a protrusion 121 can be configured to taper in a direction tangential to the scalp of the user, upon application of the system 100 to the user, such that the point 122 of the protrusion 121 facilitates combing of the protrusion 121 through the user's hair in a tangential direction. In a second example of this variation, a protrusion 121 can be configured to taper in a direction perpendicular to the scalp of the user (e.g., in a proximal-to-distal direction), upon application of the system 100 to the user, such that the point 122 of the protrusion 121 is oriented normal to the scalp of the user. As such, the protrusion(s) 121 of the array of protrusions 120 can be configured to extend laterally from a substrate defined by the housing 105, an example of which is shown in FIG. 6A, and/or to extend perpendicularly from a substrate defined by the housing 105, an example of which is shown in FIG. 6B. In alternative variations, protrusions of the array of protrusions 120 can be configured in any suitable orientation that facilitates delivery of distal ends of the protrusions to a scalp region of the user in any other suitable manner. For instance, protrusions extending from a substrate in an angled, whorled, and/or spiraled configuration (e.g., extending in a manner that is not directly perpendicular to the substrate) can provide a mechanism whereby the protrusions "screw" into position at the user's scalp. In one such specific example, the protrusions can extend from the substrate in a manner whereby a geometric projection of each protrusion onto the plane of the substrate is approximately tangential to one of a set of circles (e.g., concentric circles, non-concentric circles). Additionally or alternatively, base regions of the array of protrusions 120 that interface with the broad surface of the housing 105*b* can be one or more of: chamfered, rounded, or beveled to reduce stress concentration factors at protrusion-housing interfaces.

Figure 6C:
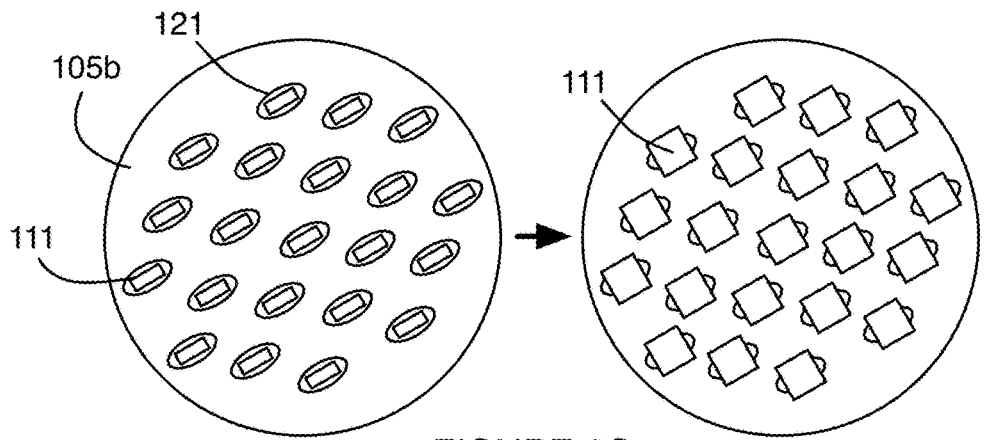

A protrusion 121 can further be defined by a rotational axis of symmetry (e.g., as in a conical, screw, auger, or barb-tipped protrusion) about a longitudinal axis, a single axis of symmetry, multiple axes of symmetry (e.g., as in a pyramidal or prismatic protrusion), or any other suitable symmetry or asymmetry. Furthermore, a protrusion 121 can be characterized by a cross-sectional profile (e.g., profile transverse to a longitudinal axis) with straight or curved edges (e.g., in a non-circular manner, in an ellipsoidal manner, etc.), an example of which is shown in FIG. 6C, and can additionally or alternatively define a non-planar surface configured to conform to a suitable surface of the user (e.g., at a region of contact for an electrode contact). For example, a protrusion 121 can comprise a concave surface (e.g., extending laterally from the housing, extending perpendicularly from the housing), which, along with a permeable body, facilitates coupling to a convex portion of a user's body (e.g., skull). In another example, a protrusion 121 can comprise a convex surface, which, along with a permeable body, facilitates coupling to a concave portion of a user's body. Furthermore, any protrusion 121 in the array of protrusions can comprise a feature at any suitable portion of the protrusion 121 (e.g., a wedge shaped profile at a distal end of the protrusion) configured to deflect a barrier to electrical coupling (e.g., hair).

At least one protrusion 121 can be deflectable and/or deformable (e.g., elastically, plastically) in order to further enhance electrical coupling between the system 100 and the user. In one variation, a protrusion of the array of protrusions 110 can be configured to deflect laterally, such that application of the array of protrusions no at the user, along with lateral deflection of a protrusion during application (e.g., by applying pressure normal to a surface of the housing 105*b* and/or laterally moving the housing 105*b* during application of the system 100 to the user), facilitates contact between the system 100 and the user. In another variation, a protrusion 121 can be configured to outwardly expand, thus laterally displacing a barrier to electrical coupling or a portion of a barrier to electrical coupling, in order to facilitate application of the system 100 to the user. In examples of this variation, the protrusion 121 can be configured to expand upon any one or more of: absorption of a fluid, infilling by a liquid or gas, transfer to a different environment (e.g., as in a shape memory material), mechanical deformation or actuation, and any other suitable mechanism of expansion. Alternatively, at least a portion of a protrusion 121 can be configured to be substantially rigid, thus allowing no deflection or deformation. As such, a protrusion 121 can be characterized by any suitable combination of variations, or any other suitable variation. Furthermore, a protrusion 121 of the array of protrusions 120 can be substantially solid, or can define a hollow region in order to facilitate electrical coupling (e.g., for providing a pathway for an electrical connection, for delivering a fluid to the protrusion to facilitate deflection and/or expansion), as described further below.

Figure 7A:
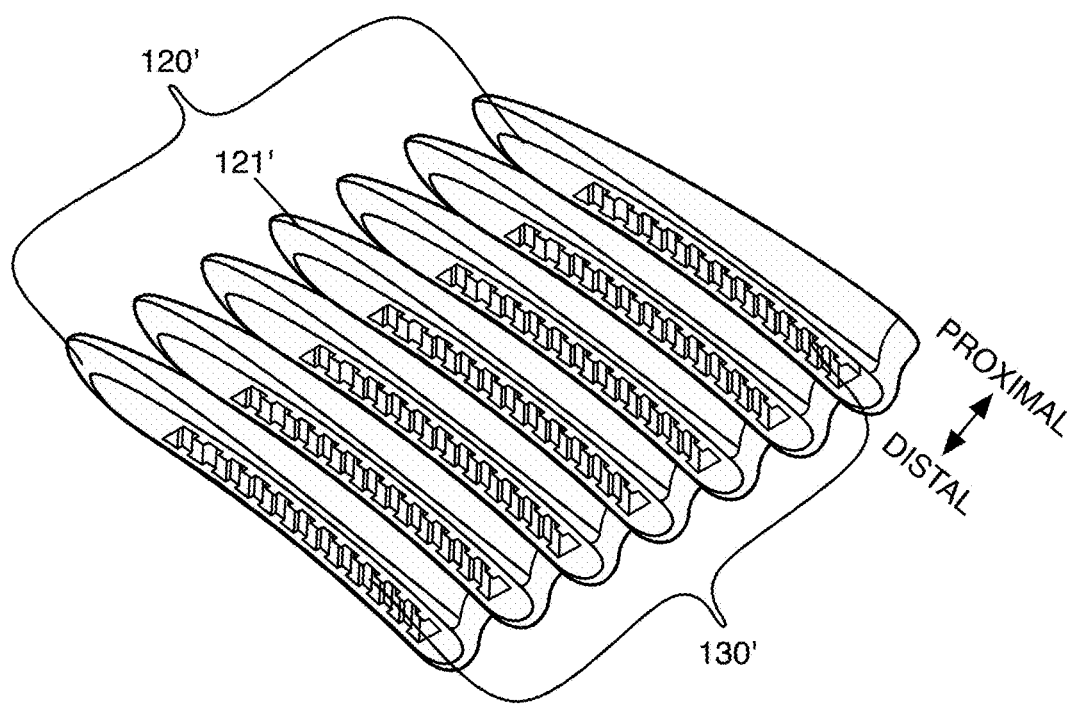
FIGS. 7A-7C depict a first example of portions of an embodiment a system for providing electrical stimulation to a user.
Figure 7B:
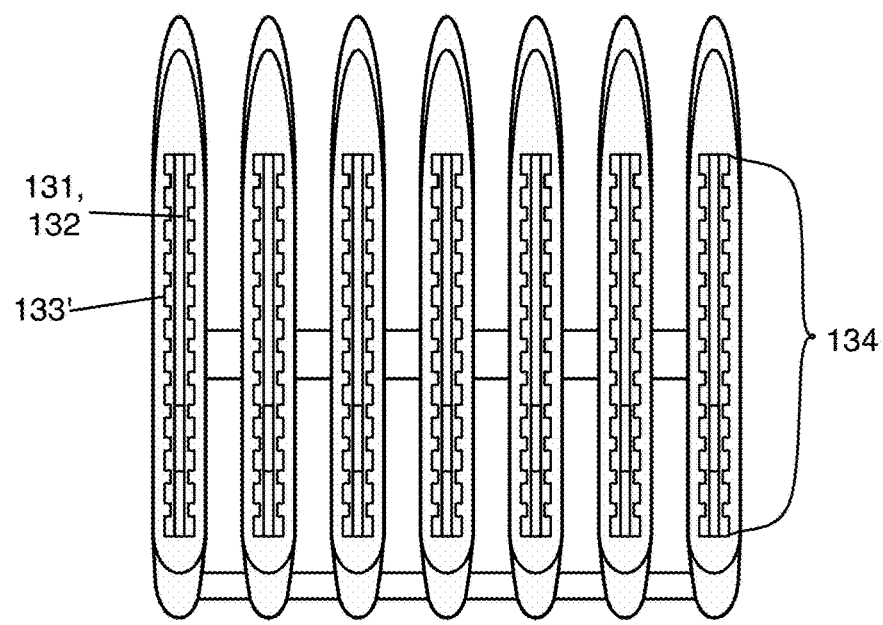
Figure 8A:
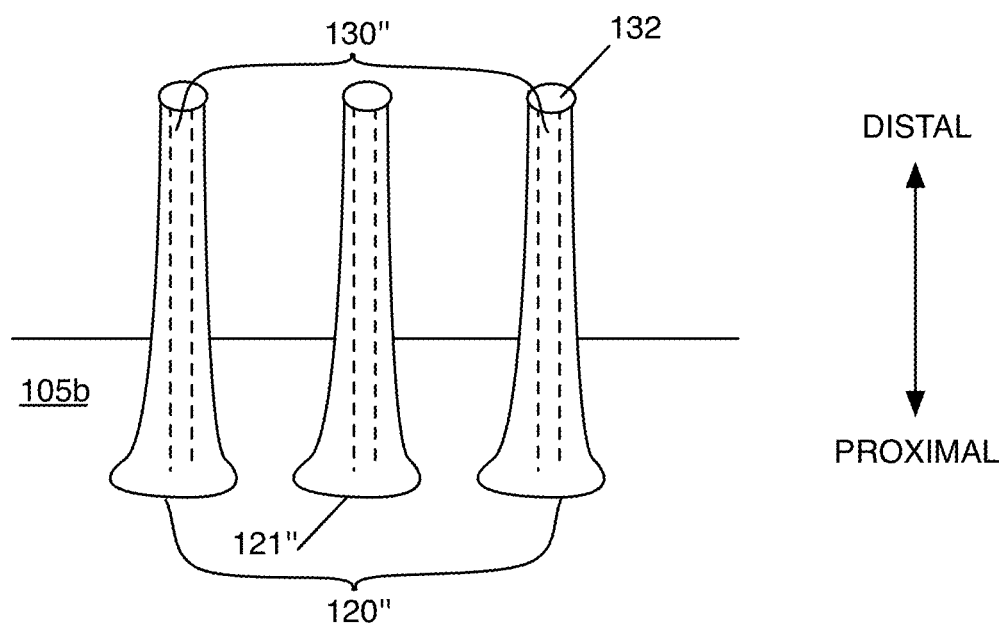
FIGS. 8A-8C depict a second example of portions of an embodiment of a system for providing electrical stimulation to a user.
Figure 8B:
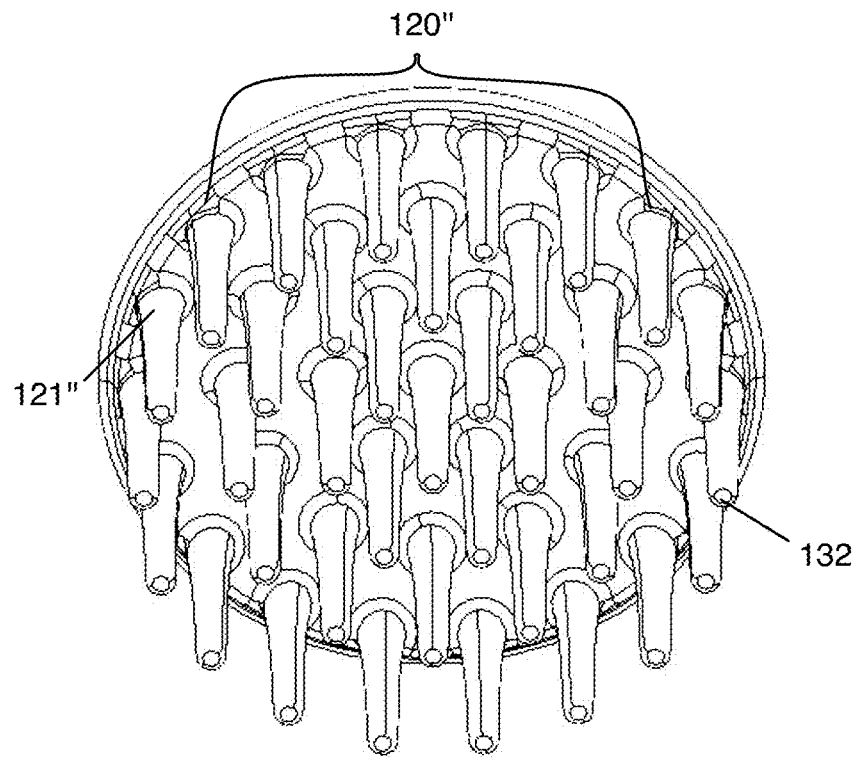

The array of channels 130 of the housing 105*b* is preferably distributed across the array of protrusions, and functions to facilitate delivery of a solution for electrical coupling to the permeable bodies associated with the array of protrusions 120. As such, the array of channels 130 is preferably in fluid communication with the array of permeable bodies 110, but can alternatively be configured to deliver the solution to the array of permeable bodies 110 in any other suitable manner. Each channel 131 of the array of channels 130 is preferably defined as a void within a protrusion 121 of the array of protrusions 120, wherein the void has an opening 132 that provides access into the channel 131 from the exterior of the housing 105; however, one or more channels of the array of channels 130 can alternatively be sealed to prevent access from the exterior of the housing 105. The array of channels 130 can be associated with the array of protrusions 120 in a one-to-one manner, in a many-to-one manner, or a less-than-one-to-one manner. In one example, as shown in FIGS. 7A and 7B, the array of channels 130' is defined as a set of voids that longitudinally pass through the array of protrusions 120 in a one-to-one manner, wherein each channel is open to the exterior of the housing 105*b* along a longitudinal surface of a corresponding protrusion 121' configured to interface with the scalp of the user. In another example, as shown in FIGS. 8A and 8B, the array of channels 130" is defined as a set of voids that longitudinally pass through the array of protrusions 120" in a one-to-one manner, wherein each channel is open to the exterior of the housing at a distal portion of a corresponding protrusion 121" configured to interface with the scalp of the user. The array of channels 130 can, however, be defined relative to the array of protrusions 120 in any other suitable manner.

A lumen of a channel 131 of the array of channels 130 can have any suitable cross-section. For instance, in variations, cross-sections at one or more regions of a channel 131 can be polygonal or ellipsoidal, and in a specific example, a non-circular cross section can prevent rotation of a permeable body 111 situated within a channel 131.

Preferably, each channel 131 in the array of channels 130 is configured to at least partially surround one or more permeable bodies of the array of permeable bodies 110, such that the permeable body(ies) are at least partially contained within an interior portion of the array of channels 130. In a first variation, an opening along a longitudinal surface of a protrusion 121 extending laterally from the housing 105*b* can be configured to receive one or more permeable bodies of the array of permeable bodies 110 into an associated channel 131, as shown in FIG. 7A. In a second variation, an opening at a distal portion of a protrusion 121 extending perpendicularly from a broad surface of the housing 105*b* can be configured to receive one or more permeable bodies of the array of permeable bodies 110 into an associated channel 131, as shown in FIGS. 8A and 8B. In surrounding the permeable bodies, the array of channels 130 preferably exposes portions of the permeable bodies (e.g., in wet and dry states) such that at least a portion of a permeable body 111 extends beyond a channel 131; however, the array of channels 130 can alternatively substantially surround the permeable bodies, at least in a dry state, such that delivery of a solution for electrical coupling to the permeable bodies allows the permeable bodies to expand beyond boundaries of the array of channels 130.

Figure 7C:
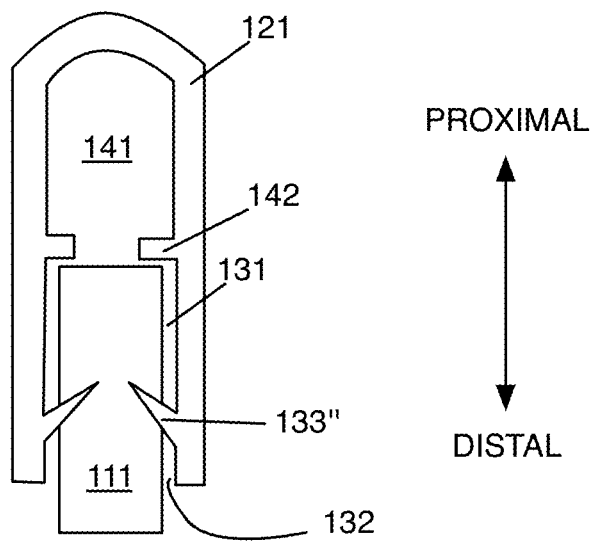

The array of channels 131 and/or the array of protrusions can, however, be alternatively configured in any other suitable manner. For instance, multiple protrusions 121 of the array of protrusions 120 can be configured to grip a single or multiple permeable bodies, such that a permeable body 111 is retained within a space defined external to protrusions of the array of protrusions 120. Furthermore, in any of the above variations and examples, one or more protrusions and/or one or more channels can include features configured to retain a permeable body 111 in position. In a first variation, an interior portion of a channel 131 can include protruding elements configured to retain a permeable body 111. In one example, as shown in FIGS. 7A and 7B, an interior portion of a channel 131 can include a corrugated surface 134 having ridges 133' that are medially oriented relative to (e.g., within) an opening 132 of the channel 131, wherein the ridges 133' facilitate retention of a permeable body 111 within the channel 131 and the spaces between ridges 133' facilitate passage of solution from the channel 131 to more completely wet the permeable body 111. In providing medially oriented ridges 133', the ridges 133' can thus define protruding elements that extend from a surface (i.e., an inner surface) of an opening 132 and protrude into the opening 132 to provide permeable body retention and/or solution passage functions. In another example, as shown in FIG. 7C, an interior portion of a channel 131 can include spiked ridges 133" that are medially oriented relative to an opening 135" of the channel 131, wherein the spiked ridges 133" facilitate retention of a permeable body 111 within the channel 131. In variations of this example, the spiked ridges 133" can be angled away from the opening (e.g., into the housing, in a distal-to-proximal direction) to provide a mechanism that prevents extraction of the permeable body in from the channel 131, or can alternatively be oriented at any other suitable angle. In a second variation, an exterior surface can include protruding elements 133 configured to retain a permeable body 111. In examples similar to those described above, an exterior surface of a protrusion 121 can include a corrugated surface 134 of ridges 133' and/or spiked ridges 133 that facilitate retention of a permeable body within a spaced defined between protrusions.

In any of the above variations and examples of the array of channels 130, protruding elements can be located throughout the depth of the channel 133, or can be isolated to regions of a channel. For instance, in some variations, the protruding elements can be isolated to distal portions of a channel 131 (e.g., portions configured close to the user's body upon application of the system 100 to the user), and substantially void from proximal portions of the channel 131.

Figure 8C:
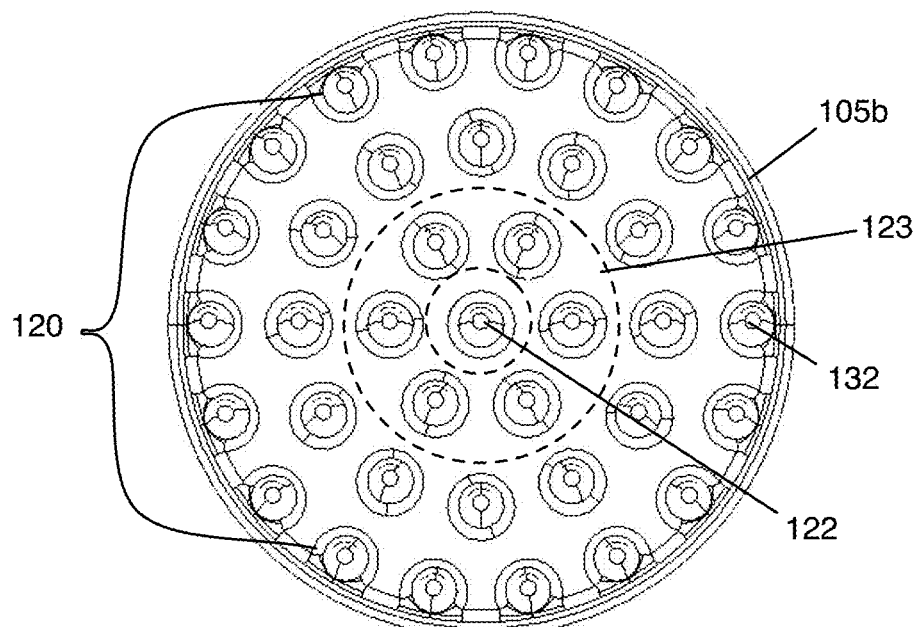
Figure 9A:
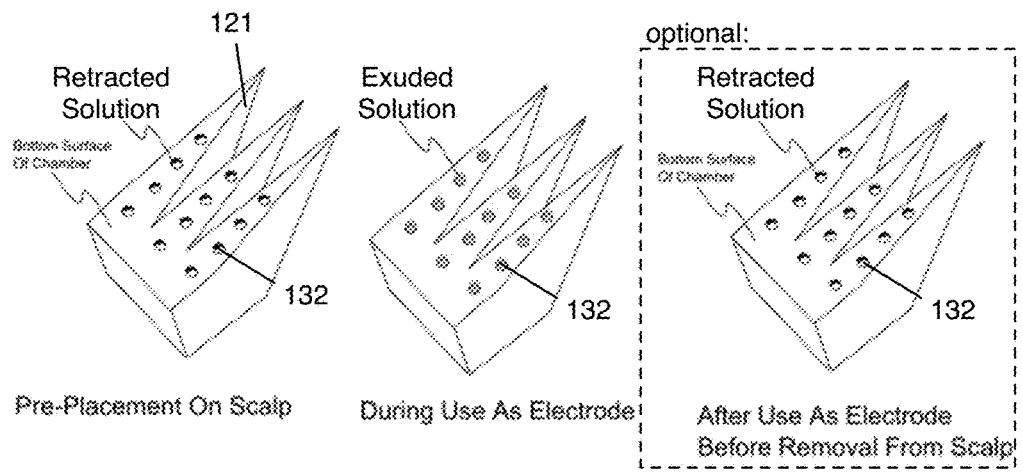
FIGS. 9A and 9B depict additional variations of portions of embodiments of a system for providing electrical stimulation to a user.

Furthermore, some variations of the system 100 can entirely omit permeable bodies, and utilize appropriately sized openings 132 of the array of channels 130 to control delivery of a solution that facilitates electrical coupling between the system 100 and the body region of the user. For instance, in one variation, as shown in FIG. 9A, a lumen of a channel can terminate in an opening 132 configured at a distal portion of the channel 131/protrusion 121 (e.g., proximal the user's scalp upon coupling of the system 100 to the user), wherein the opening 132 is sized such that an absence of forcing pressure maintains solution within the channel 131 without uncontrollable leaking of solution from the opening 132. To this end, the channel 131 can be formed of a wettable or hydrophilic substance or treated on its interior surface with a wettable or hydrophilic agent to further retention of the solution within the channel 131. Alternatively, a permeable body or membrane can be included entirely within the channel 131 (i.e. with minimal or no contact between the permeable body or membrane and the user), in order to minimize or limit solution flow in the absence of forcing pressure. In these variations, provision of a forcing pressure would then allow a controlled amount of solution for electrical coupling to be exuded from the opening 132 to facilitate electrical coupling between the system 100 and the user, without a porous body as an intermediary. In one specific example of this variation, as shown in FIG. 8C, each of an array of protrusions 120 extending perpendicularly from a broad surface of the housing 105*b* can include a channel that terminates in an opening 132 at a distal end of the protrusion 121, wherein the opening has a dimension from 0.5-0.8 mm in diameter (e.g., to accommodate saline). In another specific example of this variation, each of an array of protrusions 120 extending laterally from the housing 105*b* can include a channel that terminates in a set of openings configured along a length of a surface of the protrusion 121 configured to interface with the body region of the user, wherein the opening(s) each have a dimension from 0.5-0.8 mm in diameter (e.g., to accommodate saline). In variations of the above examples, the opening(s) 132 can alternatively comprise any other suitable dimensions. For instance, larger dimensions for the opening(s) 132 can be configured to accommodate a solution for electrical coupling that is more viscous than saline. In other variations of the system 100, the permeable bodies can be replaced by permeable or semi-permeable membranes (e.g., a thin film composite membrane, a permeable textile), located at the distal portion of at least one channel 131 of the array of channels 130, in order to make wetted contact with the user's scalp while minimizing bulk fluid flow in the absence of forcing pressure.

Figure 9B:
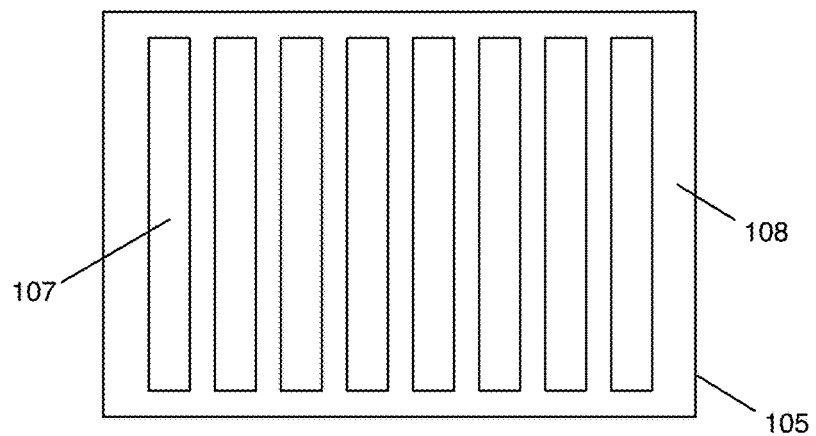

In still another variation, an example of which is shown in FIG. 9B, a permeable substrate material of a housing 105b can be processed (e.g., treated with radiation to form a mask) to define open regions 107 configured to absorb and deliver a solution of electrical coupling fluid toward a body region of the user, and closed regions 108 configured to block transmission of the solution of electrical coupling fluid. In one such example, the open regions 107 can comprise an open cell foam and the closed regions 108 can comprise a closed-cell or impermeable foam, or open-cell foam made substantially impermeable by treatment with a surface treatment such as heat or a chemical sealant, configured to substantially block transmission of a solution of electrical coupling fluid.

The manifold 140 is fluidly coupled to the array of channels 130, and functions to distribute the solution to the array of channels 130. Preferably, the manifold 140 is defined within a cavity of the housing 105b that is in fluid communication with the array of channels 130; however, the manifold 140 can alternatively be defined external to the housing 105, while being in fluid communication with the array of channels 130 through the housing. As shown in FIGS. 1, 7C, 10A, and 10B, the manifold preferably includes a set of conducting pathways 141 in fluid communication with the array of channels 130, and a reservoir 145 coupled to the set of conducting pathways 141, wherein the reservoir is configured to retain a volume of a solution for delivery into the set of conducting pathways 141 and to the array of channels 130.

Figure 10A:
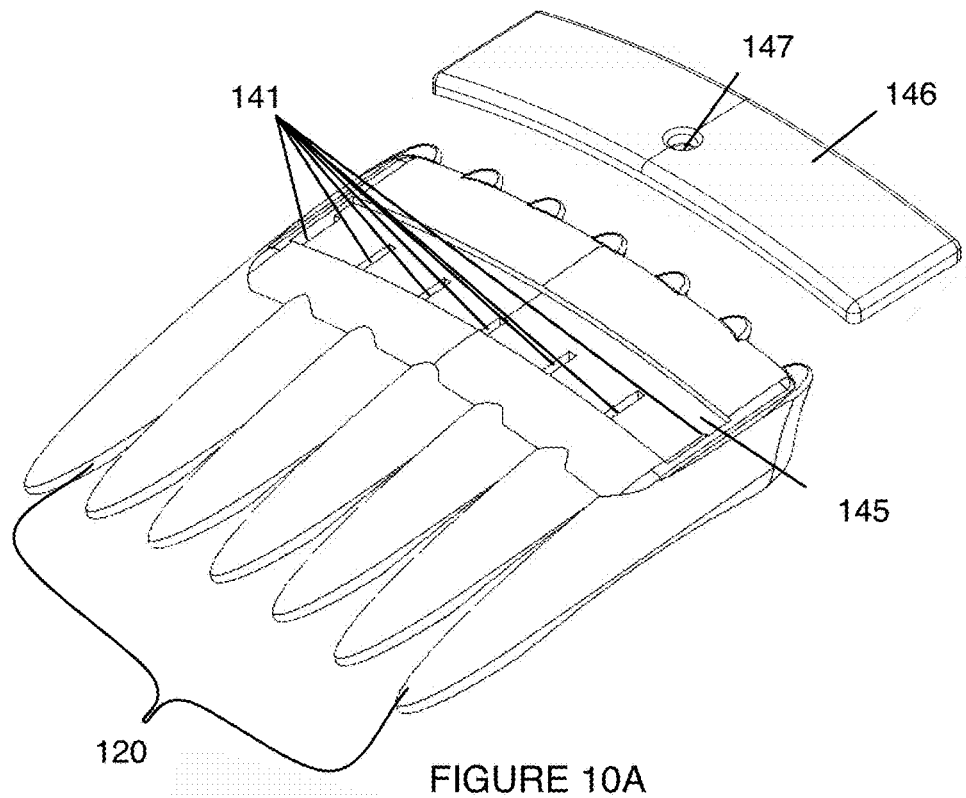
FIGS. 10A and 10B depict additional portions of the first example of a system for providing electrical stimulation to a user.
Figure 10B:
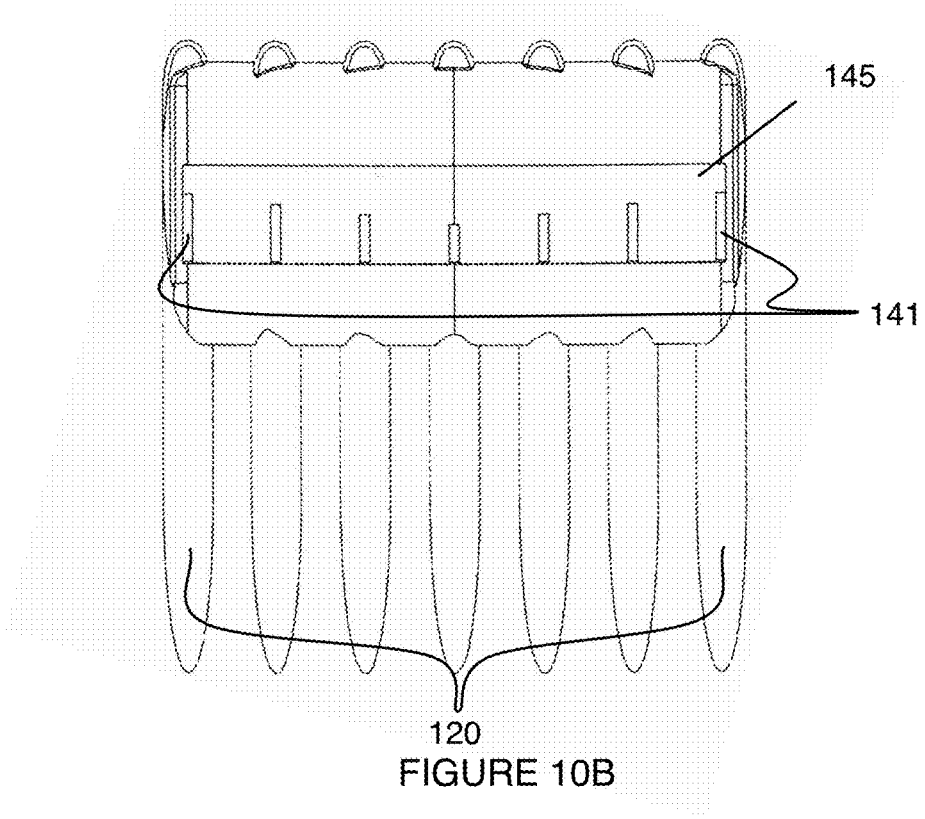

The set of conducting pathways 141 functions to convey a solution of electrical coupling fluid to the array of permeable bodies 110 (or alternatively, to openings 132 of the array of channels), such that the body region of the user can be coupled to the electronics subsystem 150 upon application of the system 100 to the user. As such, the set of conducting pathways 141 preferably comprises at least one pathway through the array of protrusions 120. In some variations, the set of conducting pathways 141 can travel from the reservoir 145 to fluidly couple to the array of channels 130, wherein at least one of the set of conducting pathways 141 and the reservoir 145 is in electrical communication with the electronics subsystem 150 by way of one or more electrical coupling regions, as described in further detail below. In these variations, the set of conducting pathways 141 can be defined through a single cavity within the housing 105b and/or within cavities of the array of protrusions 110. Furthermore, in these variations, the set of conducting pathways 141 can be associated with the array of channels 130 in a one-to-one manner, in a many-to-one manner, or in a less-than-one-to-one manner. In some variations, wherein the set of conducting pathways 141 extend from a single reservoir 145, as described in further detail below, conducting pathways positioned further from a central portion of the reservoir 145 can be configured to provide a lower amount of fluid resistance, as compared to conducting pathways positioned closer to the central portion of the reservoir 145, in order to facilitate substantially uniform delivery of a solution within the reservoir 145 to the set of conducting pathways 141. In examples, as shown in FIGS. 10A and 10B, conducting pathways positioned further from a central portion of the reservoir 145 can be configured to have a greater cross-sectional dimension (e.g., width, height), as compared to conducting pathways positioned closer to the central portion of the reservoir 145, and/or conducting pathways positioned further from a central portion of the reservoir 145 can be configured to have a greater exposed volume (e.g., greater length, greater width, greater depth) within the reservoir 145, as compared to conducting pathways positioned closer to the central portion of the reservoir 145.

Figure 11A:
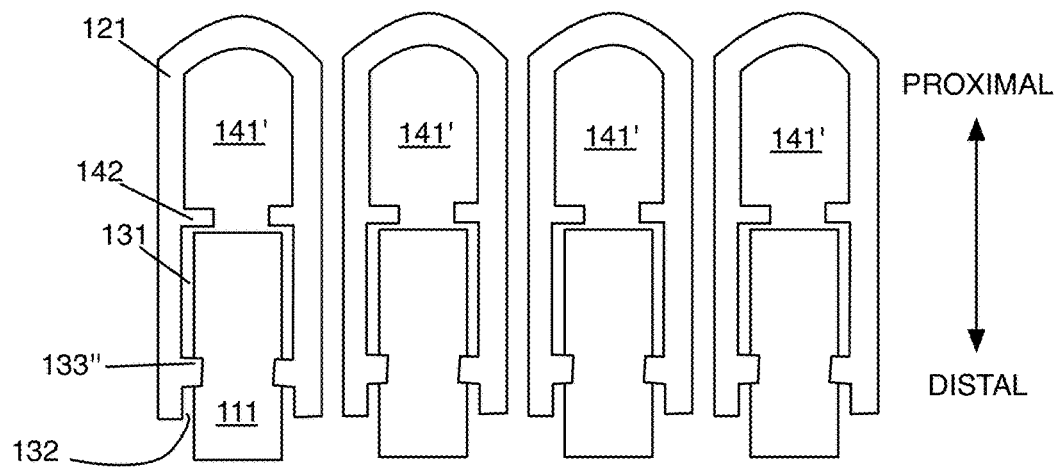
FIGS. 11A and 11B depict variations of a portion of a system for providing electrical stimulation to a user.
Figure 11B:
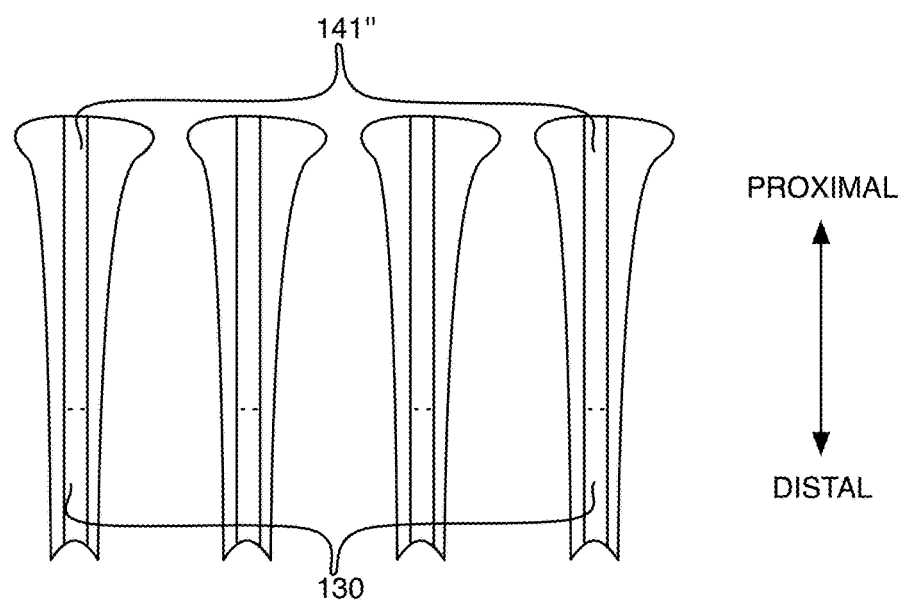

In a specific example, as shown in FIG. 11A, the set of conducting pathways 141' can be configured adjacent to and run parallel to the array of channels 130, wherein each conducting pathway of the set of conducting pathways 141' is paired with a channel 131 in a one-to-one manner. In this specific example, the set of conducting pathways 141' is configured to extend through protrusions that extend laterally from the housing 105, and the set of conducting pathways 141' is configured immediately proximal to (e.g., side-by-side with) the array of channels 130 in order to facilitate delivery of the solution to the array of channels 130. In another specific example, as shown in FIG. 11B, the set of conducting pathways 141" can be configured to run in series with the array of channels 130 in a one-to-one manner. In this specific example, the set of conducting pathways 141" is configured to extend through protrusions that extend perpendicularly from a broad surface of the housing 105, and the set of conducting pathways 141" is configured immediately proximal to (e.g., end-to-end with) the array of channels 130 in order to facilitate delivery of the solution to the array of channels 130. However, in other variations and examples, the set of conducting pathways 141 can alternatively be configured relative to the array of channels 130 in any other suitable manner.

As shown in FIGS. 1B, 7C and 11A, in some variations, one or more channels 131 of the housing 105b can comprise or be coupled to a barrier 142 configured to prevent passage of a permeable body 111 past the 142 in a distal-to-proximal direction. As such, in these variations, a permeable body 111 can be retained in position by the barrier 142 that prevents passage of the permeable body from a channel 131 into one of the set of conducting pathways 141. In examples, the barrier 142 can comprise any one or more of: an extension that protrudes into an interior portion of a channel 131 and/or one of the set of conducting pathways 141 and allows fluid transmission between the channel and the conducting pathway, a membrane spanning a cross-section of a channel 131 and/or one of the set of conducting pathways 141 that allows fluid transmission across the membrane but blocks passage of the permeable body, and any other suitable barrier that allows fluid transmission but prevents passage of a permeable body 111 into one of the set of conducting pathways 141. Variations of the housing 105b can, however, entirely omit barriers 142 between the set of channels 130 and the set of conducting pathways 141.

In alternative variations, one or more of the set of conducting pathways 141 can be configured to travel along an exterior portion of one or more of the array of protrusions 120. In still other variations, the set of conducting pathways 141 can be configured to travel along a portion of an exterior of the array of protrusions 120, and to pass into a protrusion of the array of protrusions 120, in order to facilitate electrical coupling of the array of porous bodies 110 to the electronics subsystem 150. The electrical coupling to the electronics subsystem 130 can, however, be provided in any other suitable manner.

The reservoir 145 of the manifold 140 is fluidly coupled to the set of conducting pathways 141, as shown in FIGS. 1B, 10A, and 10B, and functions to actively facilitate delivery of a solution of electrical coupling fluid into the set of conducting pathways 141 (e.g., toward permeable bodies of the array of permeable bodies). The reservoir 145 can be an on-board reservoir integrated with housing 105, or can alternatively be an off-board reservoir temporarily or permanently coupled to the housing 105b to facilitate delivery of the solution of electrical coupling fluid into the set of conducting pathways 141. The reservoir 145 can be a refillable reservoir or a single-use reservoir, and in some variations, can be configured to receive a container of fluid (e.g., a sealed fluid packet) that can be penetrated or broken in order to facilitate fluid delivery. In a single-use variation, the reservoir 145 can be configured with a burstable membrane that can be penetrated or broken, e.g. by forcing pressure or a plunger acting to provide forcing pressure, in order to facilitate fluid delivery in the activated state while preventing fluid delivery prior to activation. In one variation, as shown in FIGS. 10A and 10B, the reservoir 145 can be a recess at a superior portion of the housing 105b (i.e., in the orientation shown in FIG. 10A) configured to receive the solution, wherein the recess is fluidly coupled to the set of conducting pathways 141. In an example of this variation, the reservoir 145 can include a cap 146 that seals fluid within the reservoir 145, wherein the cap 146 allows the reservoir 145 to be accessed in order to enable replenishing of the solution. In this example, the cap 146 can provide a hermetic seal for the reservoir 145 and can additionally or alternatively enable venting of the reservoir for metering of fluid delivery. Furthermore, the cap 146 can include a port 147 configured to facilitate delivery of the solution into the reservoir 145/manifold 140, and in some instances, to facilitate driving of the solution from the reservoir into the set of conducting pathways 141. Alternatively, the reservoir 145 can omit a cap and be prepackaged with or configured to receive the solution in any other suitable manner.

In some variations, the system 100 can additionally or alternatively comprise a fluid delivery system 148, as shown in FIG. 1B, configured to actively deliver fluid into the set of conducting pathways 141 of the manifold 140, for example by producing positive pressure flow, negative pressure flow, or any combination of positive and negative pressure flow (e.g., in bidirectional flow). The fluid delivery system 148 can comprise an actuator (e.g., motor, solenoid, plunger system, diaphragm, external compressor, etc.), pump, or any other suitable element that facilitates fluid flow. Alternatively, a solution of electrical coupling fluid can be delivered from the reservoir 145 passively, for example, by gravity, or can alternatively be delivered into permeable bodies of the array of permeable bodies 110 by absorbing a fluid present in the environment. The amount of fluid delivered is preferably configured to reduce hair-wetting of the user; however, any other suitable amount of fluid can be delivered into the set of conducting pathways 141 to facilitate electrical coupling between the system 100 and the user.

In one example of the manifold 140 of the housing 105b comprising a reservoir 145 and a fluid delivery system 148, as shown in FIGS. 1B and 9A, the reservoir 145 and the fluid delivery system 148 are configured to provide a pressure that forces the solution of electrical coupling solution into the set of conducting pathways toward openings 132 of the array of channels 130, thus enabling electrical coupling between the user and the system 100, while minimizing hair-wetting. In one variation of this example omitting permeable bodies and including a solution of viscous electrical coupling fluid (e.g., electrode gel), the solution can have sufficient surface tension, such that the solution does not exit from the openings 132 unless pressure is increased within the reservoir 145. Upon placement of the housing 105b with the openings 132 facing the user's scalp, an increase in pressure within the reservoir 145, provided by the fluid delivery system 148, forces the solution of viscous electrical coupling fluid out of the openings 132 in a manner that provides electrical contact (e.g., a contiguous connection) with the user's scalp while minimizing an amount of exuded material from the openings 132. Then, when the system 100 is desired to be uncoupled from the user, the fluid delivery system 148 of this example can be configured to decrease pressure within the reservoir 145 (e.g., to a pressure level equal to or less than a pressure level provided before placement at the user's scalp). The pressure decrease allows the solution of viscous electrical coupling fluid to be retracted, through the openings 132, and back into the reservoir 145 until a subsequent period of usage. In this example, exuding the solution of viscous electrical coupling fluid during use and retracting the solution between usages can further function to preserve the solution and extend its lifetime of usability as well as minimize the amount of solution left on the user's scalp and hair. Additionally, in another example, the decrease in pressure and corresponding retraction of electrical coupling fluid can be omitted. In another variation omitting permeable bodies and including a solution of electrical coupling fluid, an increase in pressure within the reservoir 145 can force the solution out of the openings 132 in a manner that provides electrical contact, but once this occurs, contact can be maintained by a combination of mechanical compliance of the array of protrusions 120, surface tension, and wetting between the solution and the openings 132 as well as the user's scalp, rather than by high viscosity of the electrical coupling fluid. The manifold 140 of the housing 105, including the reservoir 145, the set of conducting pathways 141, and/or the fluid delivery system 148 can, however, be configured in any other suitable alternative manner. For instance, subsets of the array of protrusions 120, the array of channels 130, and the set of conducting pathways 141, as defined by the housing 105, can form independent (e.g., isolated) conducting units, such that each unit can be configured individually (e.g., one unit can serve as a cathode, and another unit can serve as an anode). Additionally or alternatively, a single housing 105b can comprise multiple sets of manifold-reservoir-conducting pathway assemblies, wherein each assembly is held at a different potential, and wherein one or more subsets of the array of channels 130 and/or openings 132 of the array of channels 130 can be configured to couple to assemblies at different potentials.

While two embodiments are described above, variations of the system 100 can include any suitable combination of one or more portions of the first embodiment and the second embodiment described above with each other, or with any other suitable electrode system 100. A few such examples of the electrode contact assembly are described in Section 1.1.4 below.

1.1.4 System—Electrode Contact Assembly Examples

In a first example, the array of protrusions 120 of a housing 105 comprises a linear array of teeth extending laterally from the housing 105, each protrusion 121/tooth defining a wedge-shaped leading edge configured to deflect hair in order to facilitate coupling. In this example, each tooth comprises a length longer than the thickness of the user's hair, in order to facilitate electrical coupling with the scalp of the user. In this example, a distal portion of each protrusion 121/tooth includes an opening 132 in fluid communication with one of an array of conducting pathways 141 and configured to surround a permeable body 111 of an array of porous bodies 110, wherein the permeable body 111 is configured to transmit a solution of electrical coupling fluid that contacts the user's skin. Furthermore, in this example, the distal portion of each protrusion 121/tooth comprises a concave surface configured to complement a convex surface of the user's scalp. In the example, the permeable body 111 is seated within a channel 131 of its protrusion 121/tooth in a dry and compressed state, such that it extends minimally or does not extend beyond the concave surface of the tooth in the dry state; however, upon absorption of the solution of electrical coupling fluid, the permeable body 111 expands both parallel and perpendicular to the user's skin surface, in order to provide an increased contact surface area, displace hair, and decrease an electrical resistance of the electrode-to-skin interface. Placement of housing 105, in this example, comprises passing a leading edge of the array of protrusions 120 through the user's hair to make contact with the skin, wherein initial contact is made posterior to a desired final electrode location. Placement further comprises movement of the array of protrusions 120 parallel to a skin surface of the user, while following a path of the leading edge of the array of protrusions 120, such that hair is deflected about the wedged-shaped leading edge and contact is made with the user's skin at a desired final location. Upon reading the desired final location, a reservoir 145 coupled to a set of conducting pathways 141 in fluid communication with the array of permeable bodies 110 is configured to deliver the solution to the array of permeable bodies 110, thus enabling fluid absorption and electrical coupling with the skin of the user.

In a second example, the array of protrusions 120" of a housing 105 comprises a two-dimensional array of conical protrusions or "spikes" extending perpendicularly from a broad surface of the housing 105, each spike in the array tapering to a blunted end configured to facilitate coupling without penetrating the skin of a user. In this example, each protrusion 121/spike comprises a length longer than the thickness of the user's hair in order to facilitate electrical coupling with the user, and furthermore, distal portions of the array of protrusions 120 defines a non-continuous concave surface configured to conform to a convex surface of the user's skull. In this example, a distal portion of each protrusion 121/spike includes an opening 132 of a channel 130 configured to partially surround a porous body 111 that contacts the user's skin after hair deflection has occurred. Furthermore, in this example, the distal portion of each protrusion 121/spike also comprises a concave surface configured to complement a convex surface of the user's skull. Furthermore, in the example, the permeable body 111 is seated within a channel 131 of a protrusion 121/spike in a dry and compressed state, such that it does not extend beyond the channel 131 of the spike in the dry state; however, upon fluid absorption, the permeable body 111 expands both parallel and perpendicular to the user's skin surface, in order to increase a contact surface area provided by the permeable body 111, displace hair, and decrease an electrical resistance of the electrode-to-skin interface. Placement of the housing 105, in this example, comprises placement of the array of protrusions 120/spikes onto a target surface of the user's body, applying pressure to the array of protrusions 120 in a direction perpendicular to the surface of the user's body, and laterally moving the array of protrusions 120 (e.g., in circular or side-to-side motions) while applying pressure, thus displacing hair, until contact between the array of permeable bodies 110 and the user's skin occurs. In this example, placement occurs by a ratchet-like mechanism, due to the tendency of hair to behave in a spring-like manner near hair follicle-skin junctions. Upon placement at the target location, a reservoir 145 coupled to a set of conducting pathways 141 in fluid communication with the array of permeable bodies 110 is configured to deliver the solution to the array of permeable bodies 110, thus enabling fluid absorption and electrical coupling with the skin of the user.

In a third example, as shown in FIGS. 8B-8C, the array of protrusions 120 of a housing 105b comprises a two-dimensional array of conical protrusions extending perpendicularly from a broad surface of the housing 105, each spike in the array tapering to a blunted end configured to facilitate coupling without penetrating the skin of a user. In this example, each protrusion 121 comprises a length longer than the thickness of the user's hair in order to facilitate electrical coupling with the user, and the array of protrusions 120 defines a circular footprint having a diameter of approximately 5 cm. In this example, the array of protrusions 120 is arranged in a series of concentric circles, with a central protrusion 122 and a first ring 123 of six protrusions (or between four and six protrusions) surrounding the central protrusion 122. Variations of the third example can, however, include any suitable number of concentric rings of protrusions, as shown in FIG. 6C. In one variation of the third example, each protrusion 121 can surround a channel 131 of an array of channels 130 configured to receive a permeable body, wherein the channel 131 is configured in series with a conducting pathway 141 of a manifold 140 configured to distribute a solution of coupling fluid to the channel 131. The channel can be configured to receive one or more seated permeable bodies in, wherein the permeable bodies do not extend beyond distal portions of the channels 131 in a dry and compressed state; however, upon fluid absorption, the permeable bodies 111 can expand both parallel and perpendicular to the user's skin surface, in order to increase a contact surface area provided by a permeable body 111, displace hair, and decrease an electrical resistance of the electrode-to-skin interface. Alternatively, the channels may not be configured to receive permeable bodies, and instead terminate in openings at distal ends of the array of protrusions that enable fluid to be exuded in a controlled manner. Placement of the housing 105, in this example, comprises placement of the array of protrusions 120 onto a target surface of the user's body, applying pressure to the array of protrusions 120 in a direction perpendicular to the surface of the user's body, and laterally moving the array of protrusions 120 (e.g., in circular or side-to-side motions) while applying pressure, thus displacing hair, until contact between the array of permeable bodies 110 and the user's skin occurs. In this example, placement occurs by a ratchet-like mechanism, due to the tendency of hair to behave in a spring-like manner near hair follicle-skin junctions. Upon placement at the target location, a reservoir 145 coupled to a set of conducting pathways 141 in fluid communication with the array of permeable bodies 110 is configured to deliver the solution to the array of permeable bodies 110, thus enabling fluid absorption and electrical coupling with the skin of the user.

Figure 12A:
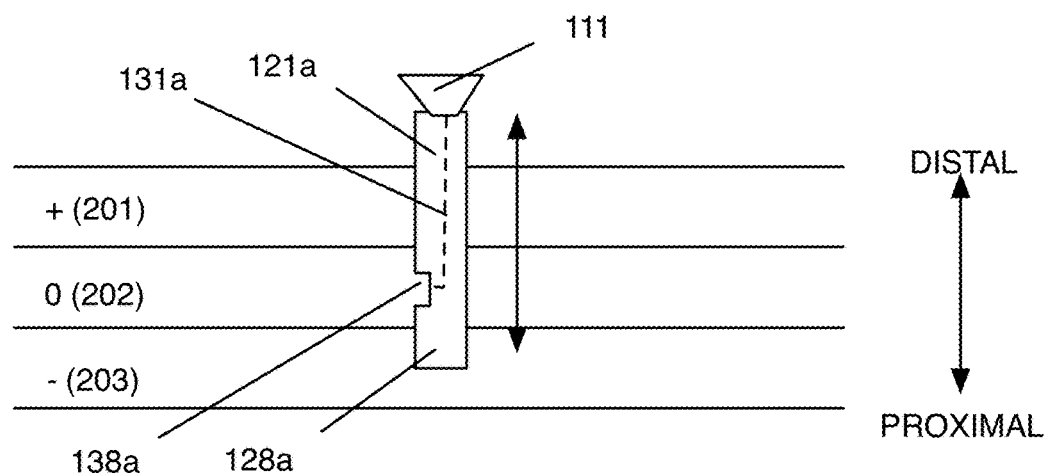
FIGS. 12A and 12B depict variations of a protrusion configuration in a system for providing electrical stimulation to a user.
Figure 12B:
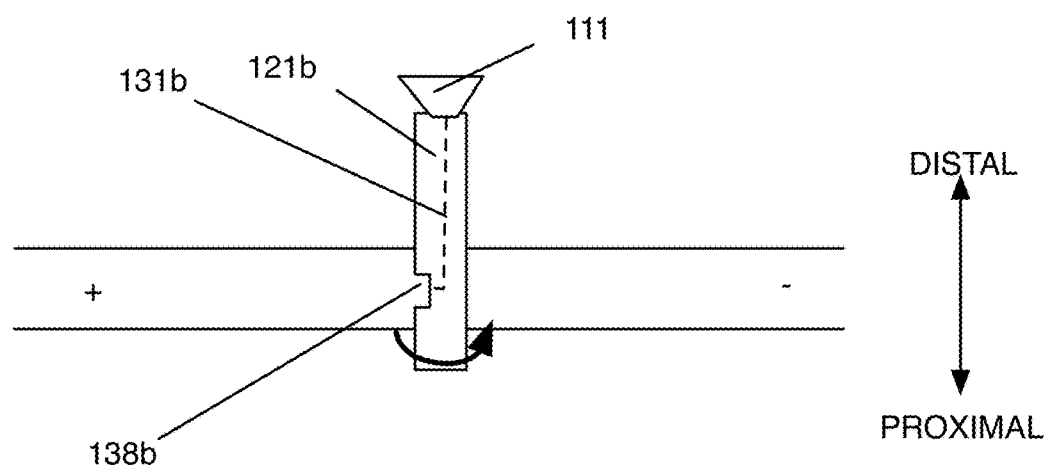

In variations of the third example, the housing 105 can include multiple sets of manifold-reservoir-conducting pathway assemblies, wherein each assembly is held at a different potential, and wherein one or more subsets of the array of channels 130 and/or openings 132 of the array of channels 130 can be configured to couple to assemblies at different potentials. In one such variation, as shown in FIG. 12A, a protrusion 121a can include a channel 131a that has an opening 138a at a proximal end 128a, wherein transitioning the opening 138a between proximal and distal positions (e.g., relative to the scalp of the user) enables the channel 131a to access volumes of solutions of electrical coupling fluid that are held at different potentials (e.g., a first potential 201, a neutral potential 202, and a second potential 203). In a similar variation, the protrusion 121a includes a non-fluid conductor, such as a metallic electrical conductor, one part of which is in electrical contact with the solution and another part of which can be transitioned (e.g. with an electromechanical switch) between electrical connectivity with metallic electrical conductors that are held at different potentials (e.g. a first potential 201, a neutral potential 202, and a second potential 203). In another such variation, as shown in FIG. 12B, a protrusion 121b can include a channel 131b that has an opening 138b along a length of the protrusion 121b, wherein rotating the opening 138b enables the channel 131b to access volumes of solutions of electrical coupling fluid that are held at different potentials (e.g., a first potential 201, a neutral potential 202, and a second potential 203). Variations of the third example can, however, be configured in any other suitable manner.

1.1.5 System—Sham Electrode Embodiment

In a first embodiment, the system 100 comprises electrode contact assemblies 101, 102 that function as either a cathode or an anode, in order to provide a level of electrical stimulation adequate for treatment (e.g., a non-control treatment). The cathode and the anode of the first embodiment of the system 100 are thus preferably separated by a distance that provides an adequate current to achieve the level of electrical stimulation needed for treatment. In an example application of the first embodiment, the separation between the cathode and the anode causes a current transmitted between them to penetrate the scalp and the brain, thus achieving a treatment level of electrical stimulation. The first embodiment thus comprises a "normal" electrode that is able to facilitate transmission of an electrical stimulation treatment (e.g., non-control treatment, or treatment intended to affect physiological function) to a user.

In a second embodiment, the electrode system 100 can include an electrode contact assembly that includes both a cathode and an anode, in order to provide a level of electrical stimulation adequate for a control treatment. In comparison to the first embodiment, the cathode and the anode of the second embodiment are separated by a smaller distance, thus providing a smaller current that achieves a lower level of electrical stimulation. In an example of the second embodiment, the close proximity of the cathode and the anode causes a current transmitted between them to pass primarily through the scalp (and not into or through the brain), thus achieving a control level of electrical stimulation. The second embodiment thus comprises a "sham" electrode that is able to facilitate transmission of a control level of electrical stimulation (e.g., control treatment, non-therapeutic treatment, or treatment not substantially affecting physiological function) to a user.

The second embodiment can function to replicate a duration of sensation (e.g., itching/tingling sensation) comparable to that provided by a first embodiment electrode system 100 without providing non-control treatment-level stimulation; thus, the second embodiment of the system 100 can provide a suitable control treatment for applications in which an electrical stimulation treatment requires an appropriate control treatment. In examples similar to those of the examples described in Section 1.1.1, "sham" electrodes are preferably configured to appear identical to "normal" electrodes (e.g., both the "sham" and the "normal" electrodes can comprise an array of teeth and/or an array of spikes), in order to facilitate conduct of clinical studies with appropriate blinding and control treatments.

1.2 System—Electronics and Coupling Subsystems

As shown in FIGS. 1A and 1B, the system 100 can further comprise an electronics subsystem 150 comprising a power module 151 and a stimulus generator 153. The electronics subsystem 150 functions to transmit stimulation and facilitate bioelectrical signal detection in cooperation with elements of the housing 105 and the array of permeable bodies 110. In some embodiments, the electronics subsystem 150 can additionally or alternatively include a signal processing module 155 configured to condition and/or to preprocess biosignals received from the user to facilitate further analyses. The electronics subsystem 150 can comprise a printed circuit board (PCB) configured to provide a substrate and to facilitate connections between electronic components, but can alternatively comprise any other suitable element(s). The electronics subsystem 150 is preferably configured to couple to the user by way of a coupling subsystem 160 described in further detail below, and can be integrated with a housing 105 or entirely distinct from the housing 105.

The power module 151 of the electronics subsystem 150 functions to serve as an electrical power source for the system 100, in order to provide regulated power to the system 100. The power module 151 can comprise a battery, but can alternatively comprise any other suitable electrical power source. In variations wherein the power module 151 comprises a battery, the battery is preferably a lithium-ion battery that is configured to be rechargeable, but can alternatively be any other appropriate rechargeable battery (e.g., nickel-cadmium, nickel metal hydride, or lithium-ion polymer). Alternatively, the battery may not be a rechargeable battery. The battery is also preferably configured to have any appropriate profile such that the battery provides adequate power characteristics (e.g., cycle life, charging time, discharge time, etc.) for stimulation and/or sensing using the electrode system 100.

In embodiments wherein the power module 151 comprises a battery, and wherein the battery is rechargeable, the electronics subsystem 130 can also comprise a charging coil that functions to facilitate inductive charging of the battery. The charging coil can be coupled to the battery and configured to convert energy from an electromagnetic field (e.g., provided by a charging dock), into electrical energy to charge the battery. Inductive charging provided by the charging coil thus facilitates user mobility while interacting with the system 100. In alternative variations, however, the charging coil can altogether be omitted (e.g., in embodiments without a rechargeable battery), or replaced by a connection configured to provide wired charging of a rechargeable battery.

The stimulus generator 153 of the electronics subsystem 150 is preferably electrically coupled to the power module 151 and a control module 154, and functions to transmit an electrical stimulation treatment, through the electrode contact assemblies 101, 102, and provide adjustability in the parameters of the electrical stimulation treatment. The stimulus generator 153 preferably comprises a current generator, but can additionally or alternatively include a voltage generator and/or any other suitable generator configured to facilitate transmission of an electrical stimulation treatment. The stimulus generator 153 is preferably configured to facilitate transmission of transcranial electrical stimulation (TES) in the form of at least one of: transcranial direct current stimulation (tDCS), transcranial alternating current stimulation (tACS), transcranial magnetic stimulation (TMS), transcranial random noise stimulation (tRNS, e.g., band-limited random noise stimulation), and transcranial variable frequency stimulation (tVFS). Additionally or alternatively, the stimulus generator 153 can be configured to provide stimulation in a pulsatile manner. As such, the stimulus generator 153 can provide any one or more of: a direct current (DC), an alternating current (AC), an AC component superimposed on a DC component, a monophasic pulsatile waveform, a symmetrical biphasic pulsatile waveform, an asymmetrical biphasic pulsatile waveform, and any other suitable stimulation profile. The waveform produced by the current generator 153 preferably can be described by parameters comprising amplitude and duration, but additionally or alternatively comprising any other suitable parameter(s), such as modulation frequency, step size, mean amplitude, or RMS value. Furthermore, any one or more of the above parameters can be configured to be modulated by the stimulus generator 153, such that the stimulus generator 153 can produce any one or more of: modulated amplitudes, modulated frequencies, and modulated pulse durations (e.g., modulated parameters characterized by exponential decay, exponential growth, or any other suitable growth or decay profiles). In coupling to a control module 154, the control module 154 is preferably configured to receive a treatment command and to provide an output to the stimulus generator 153 that adjusts one or more parameters of the electrical stimulation treatment as facilitated by the stimulus generator 153 and an electrode contact assembly 101, 102. The outputs from the control module 154 can be delivered to the stimulus generator 153 continuously, intermittently, in real time, in non-real time, and/or in any other suitable manner. While one stimulus generator 153 is described, the electronics subsystem 150 can, in some variations, comprise more than one stimulus generator 153, where the electronics subsystem 150 is configured to multiplex output of the additional stimulus generators to one or more electrode contact assemblies 101 and 102 or subsections thereof.

The signal processing module 155 of the electronics subsystem 150 functions to preprocess biosignals received from the user to facilitate further analyses of received biosignals. Preferably, the signal processing module 155 is configured to amplify biosignals from the user; however, the signal processing module can additionally or alternatively be configured to perform any one or more of: filtering of biosignals from the user, conversion of analog signals from the user into digital signals (e.g., by an analog-to-digital converter), and preprocessing of biosignals in any other suitable manner. As such, the signal processing module 155 can comprise an amplifier configured to amplify signals and/or shift signals relative to a reference voltage, wherein the amplified signals can be amplified before and/or after multiplexing. The signal processing module 155 can also comprise a filter configured to filter noise, interfering signals, and/or transients, wherein the filter can comprise a low pass filter, a high pass filter, and/or a band pass filter.

The electronics subsystem 150 can comprise any other suitable element, such as a data link 157, which functions to transmit an output of at least one element of the system 100 to a mobile device 158 or other computing device. Preferably, the data link 157 is a wireless interface; however, the data link can alternatively be a wired connection. In a first variation, the data link 157 can include a Bluetooth module that interfaces with a second Bluetooth module included in a mobile device or external element, wherein data or signals are transmitted over Bluetooth communications. The data link 157 of the first variation can alternatively implement other types of wireless communications, such as 3G, 4G, radio, or Wi-Fi communication. In the first variation, data and/or signals are preferably encrypted before being transmitted by the data link. For example, cryptographic protocols such as Diffie-Hellman key exchange, Wireless Transport Layer Security (WTLS), or any other suitable type of protocol may be used. The data encryption may also comply with standards such as the Data Encryption Standard (DES), Triple Data Encryption Standard (3-DES), or Advanced Encryption Standard (AES).

The coupling subsystem 160 comprises a first electrical coupling region 161 in electrical communication with an interior portion of the housing 105 and a second electrical coupling region 162, configured to couple the first electrical coupling region to the electronics subsystem. The coupling subsystem 160 thus functions to allow outputs of the electronics subsystem 150 (e.g., of the stimulus generator 153) to be transmitted through the solution of electrical coupling fluid (e.g., saline) in communication with (e.g., saturating, absorbed by, etc.) the array of permeable bodies 110, in order to enable transmission of electrical stimulation to the body region of the user. The coupling subsystem 160 can additionally or alternatively function to enable reception of signals (e.g., signals from the user, signals indicative of impedance from any electrical interface of the system 100, etc.), which can facilitate biosignal detection from the user and/or ensure proper function of the system 100. The first electrical coupling region 161 and the second electrical coupling region 162 are preferably composed of conductive metallic elements (e.g., copper, gold, silver, brass, aluminum, etc.), but can additionally or alternatively be composed of any other suitable element(s). Preferably, the first electrical coupling region 161 and the second electrical coupling region 162 are configured (e.g., processed, positioned, etc.) in a manner that prevents corrosion; however, the first and the second electrical coupling regions 161, 162 can alternatively be configured in any other suitable manner. For instance, variations of either the first electrical coupling region 161 and the second electrical coupling region 162 may not be processed to prevent corrosion, such that one or more aspects of the system 100 are configured for one-time-use.

In interfacing with each other, the first electrical coupling region 161 and a second electrical coupling region 162 can mate with each other in a reversible manner, such that an electrode unit can be removably and reversibly coupled to other portions of the system (e.g., portions including the electronics subsystem 160). However, the first electrical coupling region 161 and a second electrical coupling region 162 can alternatively couple with each other in a not easily reversed manner. In variations, coupling between the first electrical coupling region 161 and a second electrical coupling region 162 can be provided using one or more of a mechanical coupling mechanism and a magnetic coupling mechanism. In a first specific example, as shown in FIGS. 5A, 5B and 5C, the first electrical coupling region 161 can comprise a tab (i.e., as a male connection) that mechanically mates with a pin within a socket (i.e., as a female connection) of the second electrical coupling region 162.

Additionally or alternatively, in a second specific example, as shown in FIG. 5C, the first electrical coupling region 161 and a second electrical coupling region 162 can be promoted to couple with each other by using magnetic/ ferromagnetic materials at desired regions of the system 100, wherein the magnetic/ferromagnetic materials enable magnetic coupling and consequently promote physical and electrical coupling between the first electrical coupling region 161 and the second electrical coupling region 162.

The first electrical coupling region 161 preferably has portions at least partially situated within an interior portion of the housing 105, and functions to enable stimulation transmission from the electronics subsystem 150 through the array of permeable bodies 110 to the user. In relation to the first embodiment of the housing 105 and substrate region 50 described in Section 1.1.2 above, the first electrical coupling region 161 preferably interfaces with a set of conductors 60 that provide different subregions of the substrate region 50 with different characteristics (e.g., different polarities). However, the set of conductors 60 (and/or other aspects of the system 100) can additionally or alternatively be configured to provide all regions of the substrate region 50 with substantially the same characteristics (e.g., in terms of polarity) In variations, the portion of the first electrical coupling region 161 that is interior to the housing 105 can include a metallic pad 62 (or other conducting pad) that interfaces with at least a portion of the substrate region 50, and an electronics substrate 64 (e.g., printed circuit board, flex printed circuit, etc.) that interfaces with the metallic pad 62. The electronics substrate 64 can further include one or more connectors 65 that interface with the second electrical coupling region 162 that is coupled to the electronics subsystem 160, as shown in FIG. 5D.

In variations, the connectors 65 of the electronics substrate 64 can include one or more of a detection connector 65a and a stimulation connector 65b. In one example, as shown in FIG. 5D, a detection connector 65a can be coupled, from the electronics substrate 64, to a stimulation connector 65b with a resistor. In the example, one or more stimulation connectors 65b, as shown in FIG. 5D, can be coupled from the electronics substrate 64 to the metallic pad 62 in order to provide a conductive path to at least a portion of the array of permeable bodies. Also shown in FIGS. 5A-5D, the electronics substrate can comprise more than one stimulation connector 65b that each couple to different regions of the metallic pad 62, in providing a conductive path to corresponding sub-portions of the array of permeable bodies 110.

In more detail, each unit of the electrode system 100 can be provided with a characteristic resistor value (e.g., 1 MOhm for a central unit 101a of the electrode system, 500 kOhm for a side unit 102a, 103a of the electrode system, etc.), with detection of the type of electrode unit associated with the characteristic resistor value, and/or detection of stimulation-related parameters enabled through a detection circuit of the electronics subsystem 160. In one such example detection circuit, the detection circuit 59 can be configured to provide a probe voltage to the stimulation connector(s) 65b with respect to a ground, (e.g., a voltage created by a voltage-controlled current source circuit), while not providing a complete return path for current to flow through the user. The probe voltage thus causes a characteristic voltage to occur at the detection connector 65a, which depends upon the value of the resistor and the value of the probe voltage. This characteristic voltage can thus be sensed by the detection circuit 59, which can be used to trigger an alert state (e.g., to output an alert output in relation to appropriateness of the electrode units being used for a desired stimulation program, in relation to proper electrical behavior of an electrode unit, in relation to a scenario wherein no electrode unit is installed prior to a desired period of use of the system, in relation to a scenario where a foreign body is installed, etc.). However, the first electrical coupling region 161 can alternatively be configured in any other suitable manner.

In one example, the set of conductors 60 of the first electrical coupling region 161 can provide a first subregion 53a of the substrate region 50 with a first polarity, and both a second subregion 53b and a third subregion 53c of the substrate region 50 with a second polarity (e.g., with one subregion acting as an anode and with another subregion acting as a cathode, for delivering of band-limited random noise stimulation, etc.). However, the set of conductors 60 can alternatively be configured relative to the substrate region 50 in any other suitable manner.

In relation to the second embodiment of the housing 105 described in Section 1.1.3 above, the first electrical coupling region 161 can be configured proximal at least one of an interior surface of the manifold 140, the set of conducting pathways 141, and the array of channels 130. The first electrical coupling region 161 is preferably configured to maintain contact with the solution of electrical coupling fluid while stimulation is being provided to the user and/or while signals are being detected, and as such, is preferably configured along a path of fluid flow of the solution throughout the housing. In one variation, the first electrical coupling region 161 is positioned near a distal portion of an interior of the housing 105 (e.g., at a distal portion within the manifold 140), upon coupling of the housing 105 to the user, such that gravitational force facilitates maintenance of contact between the first electrical coupling region 161 and the solution of electrical coupling fluid. Additionally, in this variation the electrical coupling region can be configured to extend from the distal portion of the interior of the housing 105, and to exit from the housing 105, in order to couple to the electronics subsystem 150 (i.e., by way of the second electrical coupling region). The first electrical coupling region 161 can, however, be configured in any other suitable manner. For instance, the first electrical coupling region 161 can include one or more leads that extend into the set of conducting pathways 141/array of channels 130 to enable stimulation transmission to the user and/or signal detection from the user.

The second electrical coupling region 162 is preferably positioned exterior to the housing 105, and configured to couple to the first electrical coupling region 162 to enable stimulation transmission to the user and/or signal detection from the user. The second electrical coupling region 162 and the first electrical coupling region 161 are preferably composed of identical materials in order to prevent galvanic corrosion; however, the second electrical coupling region 162 and the first electrical coupling region 161 can alternatively be composed of non-identical materials. Preferably, the second electrical coupling 162 and the first electrical coupling 161 are configured to be reversibly coupled to each other, such that a portion of the first electrical coupling 161 and the second electrical coupling 162 mate with each other. As such, in examples, the first and the second electrical couplings 161, 162 can form a male-female coupling 163 that is isolated from the solution of electrical coupling fluid in order to provide modularity in the system 100. As such, any corrosion or passivation of the first electrical coupling region 161, within the housing 105, can be isolated from the second electrical coupling region 162 (e.g., in a variation in which the elements of the housing 105 are not configured to be reusable). Alternatively the first electrical coupling region 161 and the second electrical coupling region 162 can be of unitary construction, such that the first electrical coupling region 161 and the second electrical coupling region 162 have a single joined configuration and cannot be uncoupled from one another. In an additional variation, the coupling subsystem 160 projects distally to the array of permeable elements 110 (e.g., through channels of the array of channels 130), allowing outputs of the electronics subsystem 150 (e.g., of the stimulus generator 153) to be transmitted to the array of permeable bodies 110 without the need for a manifold 140 or a continuous path of electrical coupling fluid from the interior portion of the housing 105 to each permeable body 111.

1.3 System—Other Elements

Figure 13:
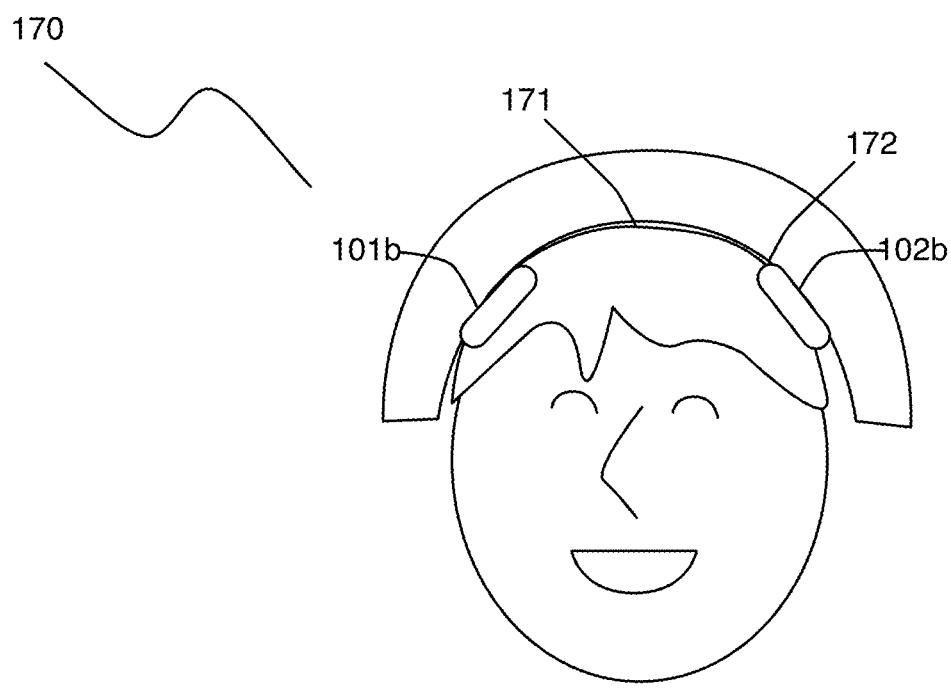
FIG. 13 depicts a variation of a positioning module in a system for providing electrical stimulation to a user.

The system 100 can additionally further comprise a positioning module 170, as shown in FIG. 13, which is configured to facilitate placement of the electrode system 100 at the user's scalp. The positioning module 170 preferably couples to an element of the system 100 (e.g., a housing) in a reversible manner and/or a reconfigurable manner, but can alternatively couple to the element of the system 100 in a permanent or a semi-permanent manner. Additionally, the positioning module 170 can be configured to house at least a portion of the electronics subsystem 150, and to provide an electromechanical connection between the electronics subsystem 150 and an electrode contact assembly 101*b*, 102*b* by way of the positioning module 170. The positioning module 170 can additionally or alternatively be configured to guide motion of the array of protrusions 120 of a housing 105 of the system 100, in order to facilitate formation of an electrical connection between the user and the system 100. In one variation, as shown in FIG. 13, the positioning module 170 is configured to follow the contour of the user's skull (e.g., as in a helmet, cap, headband, halo, or headset), and includes at least one track 171 with a carriage 172 configured to couple to at least one of the array of protrusions 120. However, the track 171 can be configured to couple to any other suitable element of the system 100. In this variation, the track(s) 171 conform to the surface of the scalp and run parallel or antiparallel with a prevailing grain of hair growth, such that placement of the positioning module 170 at the user's scalp "combs" the array of protrusions 120 through the user's hair and facilitate electrical coupling between the system 100 and the user. In other variations, the positioning module 170 can be configured to couple to the system 100 in any other suitable manner, couple to any other suitable portion of the user's body, and guide motion of the system 100, relative to the user, along any other suitable direction.

In some variations, the positioning module 170 can be configured to communicate in a one-way or two-way manner with one or more electrode contact assembly 101, 102. As such, detection that an electrode contact assembly 101, 102 was properly coupled, and identification of which electrode contact assembly(ies) were coupled to the electronics subsystem 150 can be determined. In variations, communication between the positioning module 170 and the electrode contact assembly(ies) 101*a*, 102*a*, 103*a*, 101*b*, 102*b*, can be provided by one or more of: an electromechanical connection, an optical sensor, an identification sensor (e.g., RFID), and any other suitable mechanism of communication. In an example, communication includes communication of the approximate shape, position, and/or area of the electrode-to-user contact region provided by the electrode contact assembly 101, 102 from the electrode contact assembly 101, 102 to the positioning module 170; additionally, this information or derived information (e.g., charge density) can be presented to the user (e.g. using a mobile device 158) or used by the electronics subsystem 150 to prevent delivery of stimulation that would increase a value such as charge density or accumulated charge density past a predetermined limit.

Figure 14A:
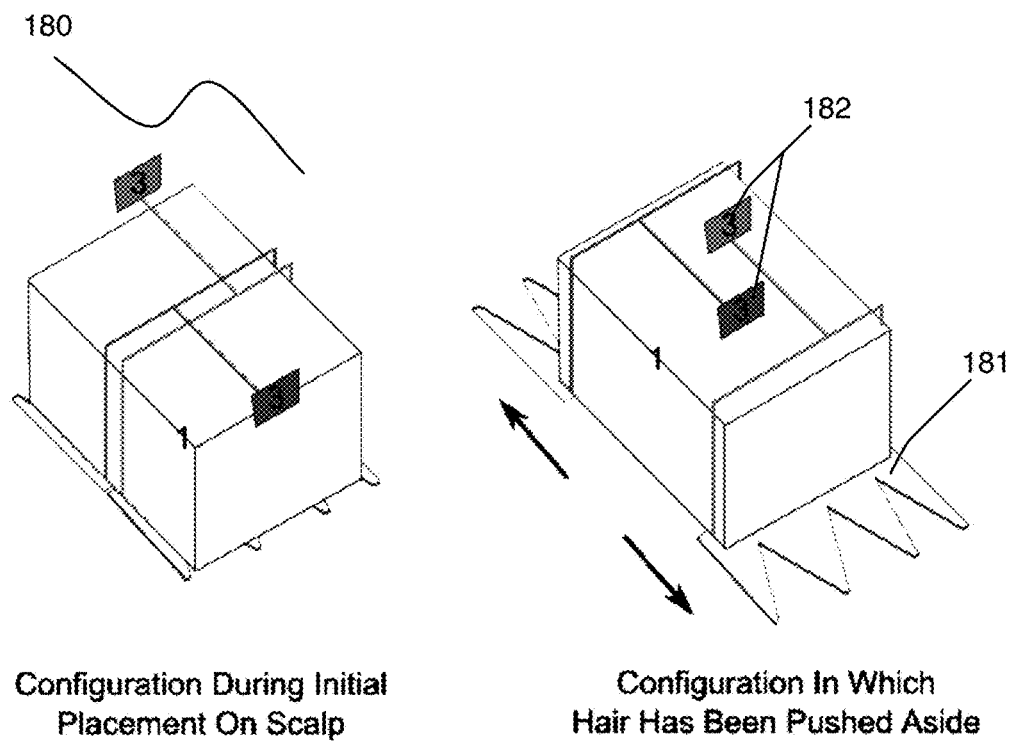
FIGS. 14A-14B depicts an embodiment of a module for displacing a user's hair, in an embodiment of a system for providing electrical stimulation to a user.
Figure 14B:
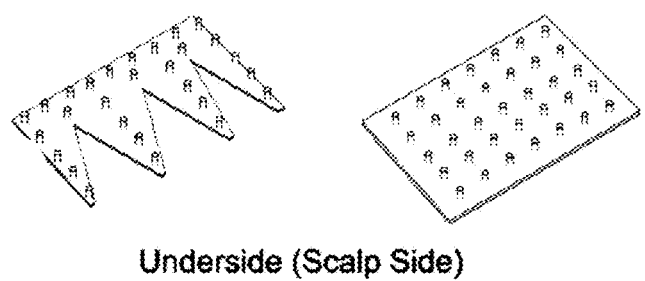
Figure 15A:
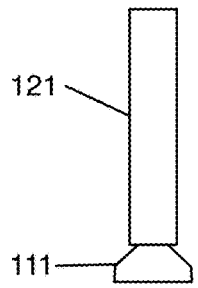
FIGS. 15A-15B depict variations of a portion of a system for providing electrical stimulation to a user.
Figure 15B:
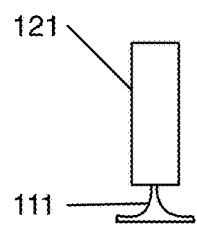

As shown in FIGS. 14A-14B, the electrode system 100 can additionally further comprise a hair displacement module 180, which functions to facilitate stimulation and/or signal recording by the system 100, by providing access, through the user's hair, to the user's skin. The hair displacement module 180 preferably facilitates the displacement of hair to allow contact between the system 100 and the skin of the user, by way of a mechanism that laterally displaces the user's hair (e.g., when the user pushes a button, when the user turns a knob, when the user slides a post, when the user activates any other suitable input device, etc.), an example of which is shown in FIG. 14A. The hair displacement module 180 can, however, displace the user's hair in any other suitable manner. As described briefly above, one or more portions of the system 100 can be configured to expand outward to laterally displace hair of the user (e.g., upon absorption of fluid). In one such variation, examples of which are shown in FIGS. 15A and 15B, one or more regions of a permeable body 111 situated within a protrusion/channel of the housing 105 can be configured to undergo at least one of volumetric expansion (as shown in FIG. 15A) and area expansion (as shown in FIG. 15B) to promote contact between the system 100 and skin of the user. However, in achieving a desired contact area condition at a system-user body interface, a permeable body 111 configured for area expansion can use a significantly smaller volume of fluid for saturation of the permeable body 111.

Figure 16A:
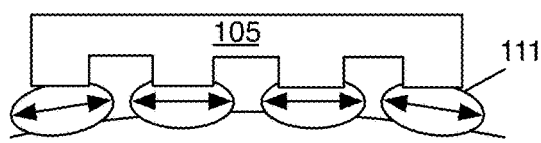
FIGS. 16A-16D depict variations of a portion of a system for providing electrical stimulation to a user.
Figure 17:
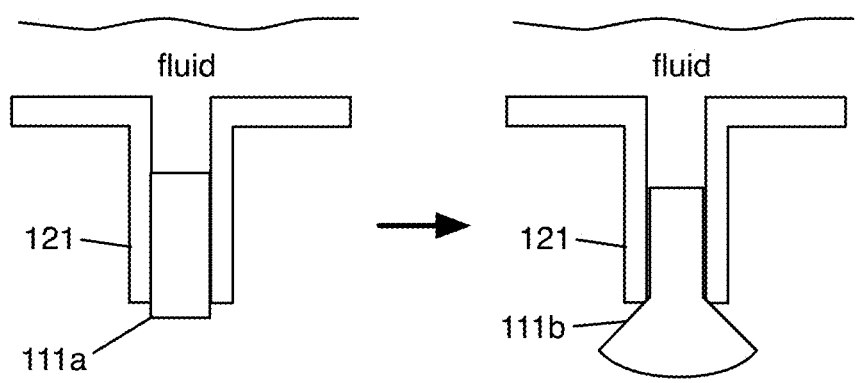
FIG. 17 depicts a first example of a first variation of a portion of a system for providing electrical stimulation to a user.

In deploying tip regions of the array of permeable bodies 110 for contact with the body region of the user, the housing 105 and/or any other suitable portion of the system 100 can be configured to transition the array of permeable bodies 110 from a contracted state 111*a* to an extended state 111*b* relative to the housing 105 (and/or any other suitable portion of the system 100). In a first variation, as shown in FIG. 16A, the array of permeable bodies 110 can be configured to expand in place, once the system 100 is positioned on the user, in establishing contact between the array of permeable bodies 110 and the body region of the user. In examples of the first variation, one of which is shown in FIG. 17, the material of the permeable bodies 110, as described above, can absorb fluid and volumetrically expand within a confined region (e.g., channel of the housing no) having an opening, such that the material expands outward from the opening to establish contact with the body region of the user. Additionally or alternatively, in another example of the first variation, microfluidic channels of the manifold 140 can be designed to improve consistency of fluid distribution to the array of permeable bodies 110 to promote expansion of the array of permeable bodies 110 in place at the user.

Figure 16B:
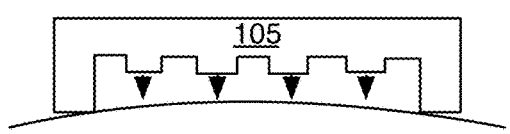
Figure 18A:
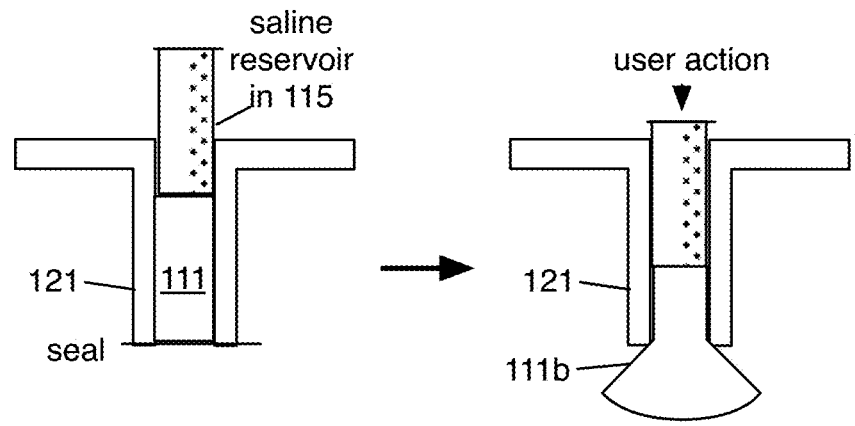
FIGS. 18A-18D depict examples of a second variation of a portion of a system for providing electrical stimulation to a user.

In a second variation, as shown in FIG. 16B, the array of permeable bodies 110 can be transitioned to the extended state 111*b*, from the housing 105, in establishing contact between the array of permeable bodies 110 and the body region of the user. In a first example of the second variation, as shown in FIG. 18A, a chamber 115 that is actuatable within a channel of the housing 105 can support a permeable body 111 in a contracted state ma, wherein the contracted state is maintained by way of a seal (e.g., foil seal, plastic seal, paper seal, seal configured to dissolve when wet, cap, etc.) coupled at a distal end of the channel. In the first example, the chamber 115 can include a reservoir for a volume of fluid that saturates the permeable body, upon displacement of the chamber 115 in a distal direction to transition the permeable body to the extended state 111*b*

Figure 18B:
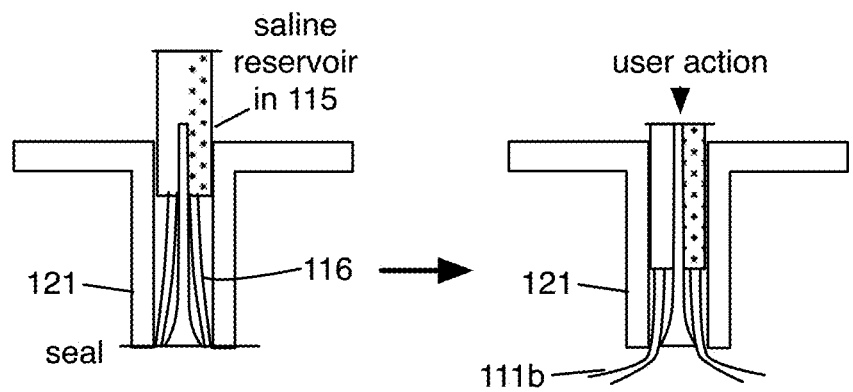
Figure 18C:
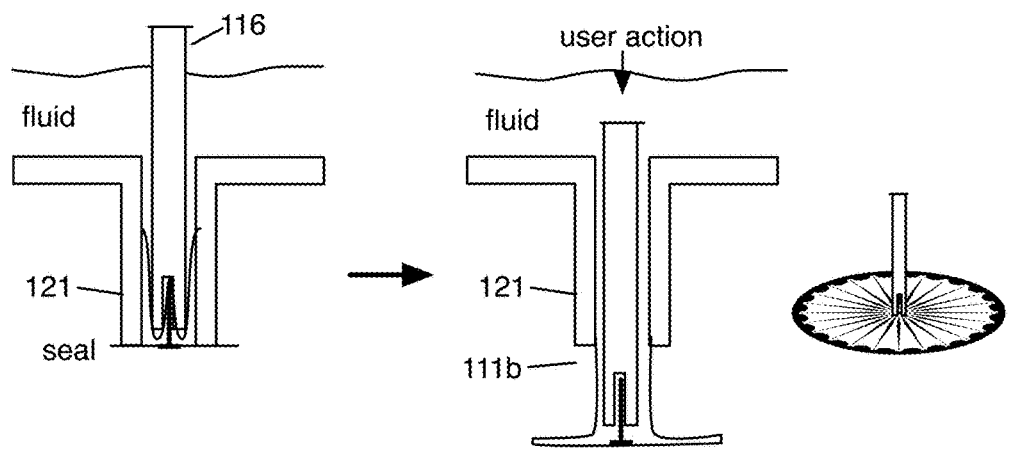
Figure 18D:
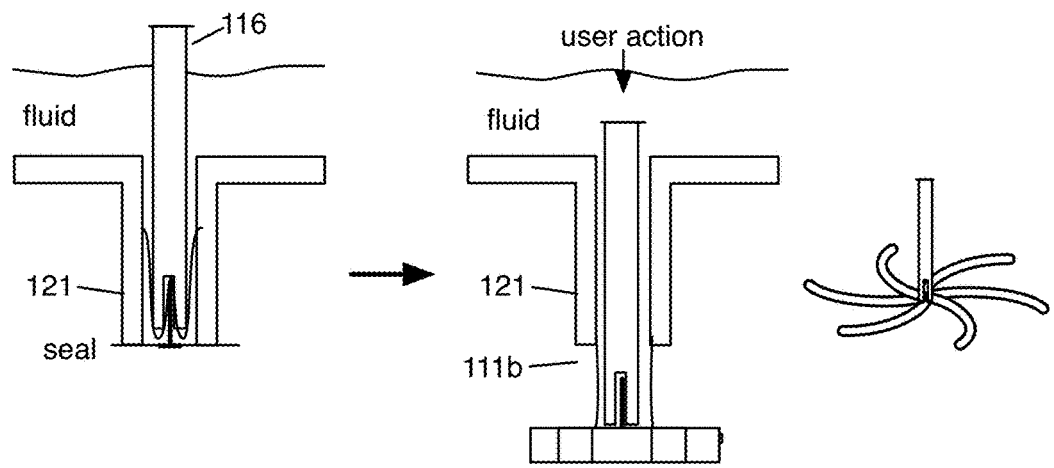
Figure 19A:
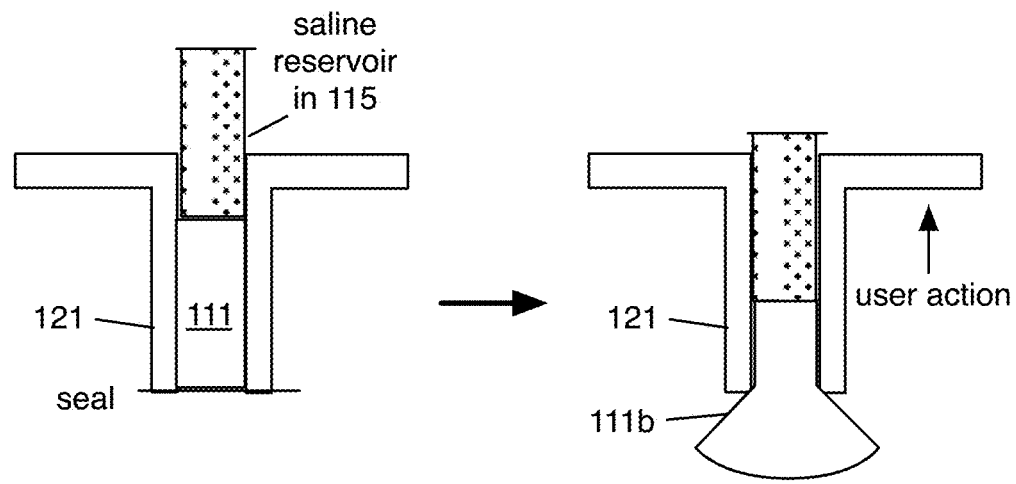
FIGS. 19A-19D depict examples of a third variation of a portion of a system for providing electrical stimulation to a user.
Figure 19B:
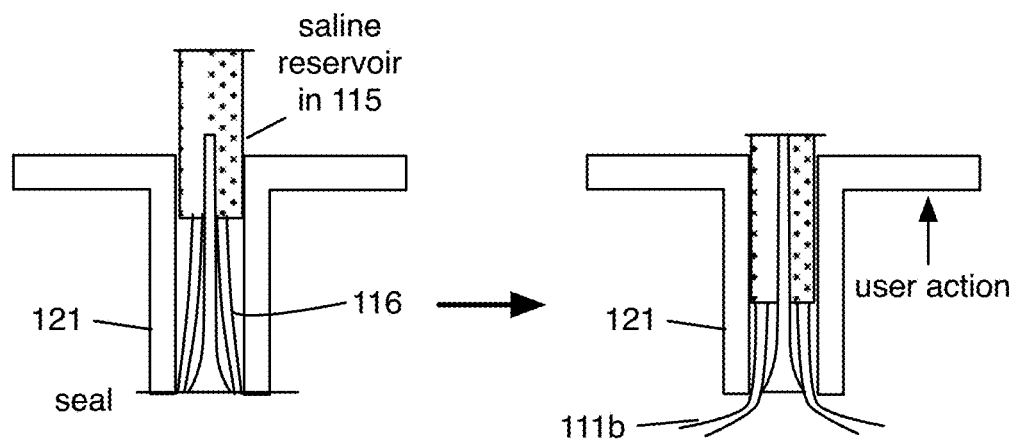
Figure 19C:
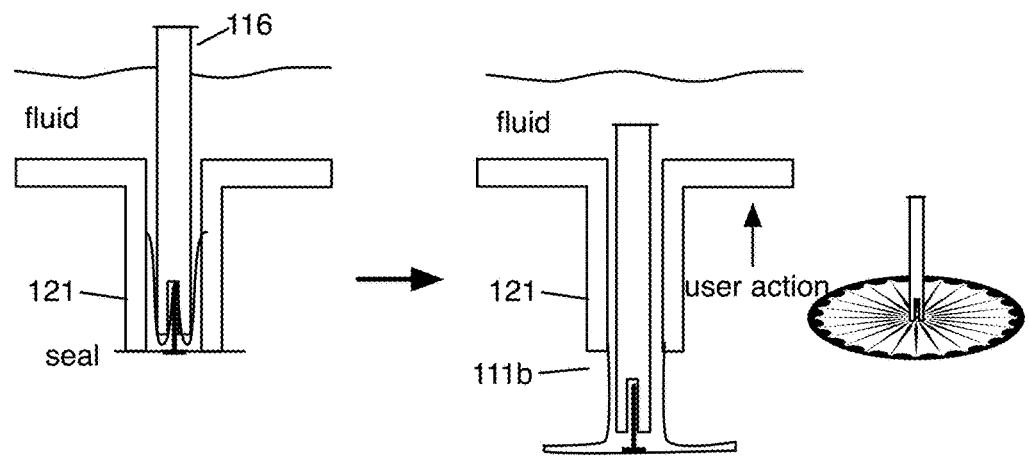
Figure 19D:
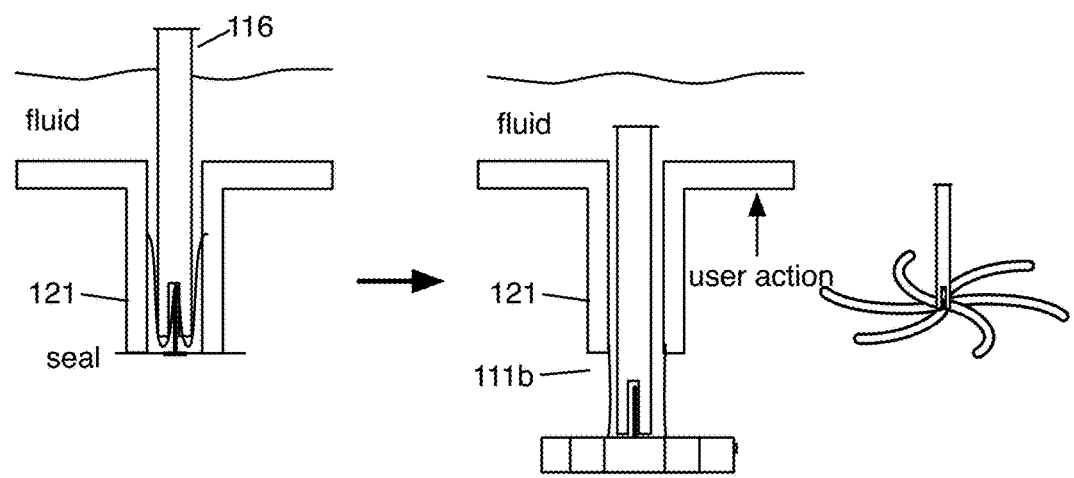

(with breaking of the seal). In a second example related to the first example, as shown in FIG. 18B, the array of permeable bodies 110 can comprise a set of wicking elements 116 configured to splay outward about a flanged portion of the housing 105 upon transitioning the permeable bodies 110 from the contracted state 111a to the extended state 111b. In a third example related to the first example, as shown in FIG. 18C, the chamber 115 can be substituted with a post 116 configured to couple with a portion of a permeable body in having a folded configuration, that expands outward (e.g., as in a fanned configuration) upon transitioning the permeable body in from the contracted state 111a to the extended state 111b. In a fourth example related to the third example, as shown in FIG. 18D, the portion of a permeable body in configured to expand can have a spiral-wound configuration, that unwinds outward upon transitioning the permeable body in from the contracted state 111a to the extended state 111b.

Figure 16C:
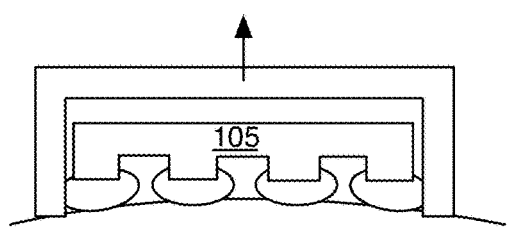

In a third variation, as shown in FIG. 16C, the array of permeable bodies 110 can be configured to be exposed upon retracting of one or more portions of the housing 105, and/or elements associated with the housing 105 in establishing contact between the array of permeable bodies 110 and the body region of the user. In examples of the third variation that are analogous to the examples of the second variation, as shown in FIGS. 19A-19D, the housing 105 can be displaced relative to an object (e.g., chamber 115, post 116) supporting a permeable body 111, thereby transitioning the permeable body from the contracted state 111a to the extended state 111b.

Figure 16D:
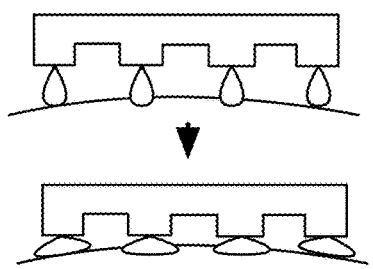
Figure 20A:
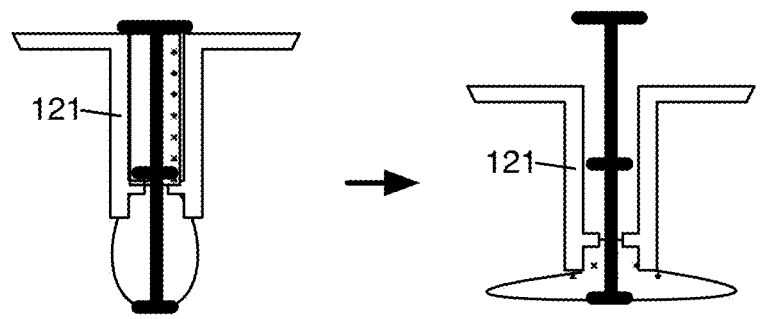
FIGS. 20A-20C depict examples of a fourth variation of a portion of a system for providing electrical stimulation to a user.
Figure 20B:
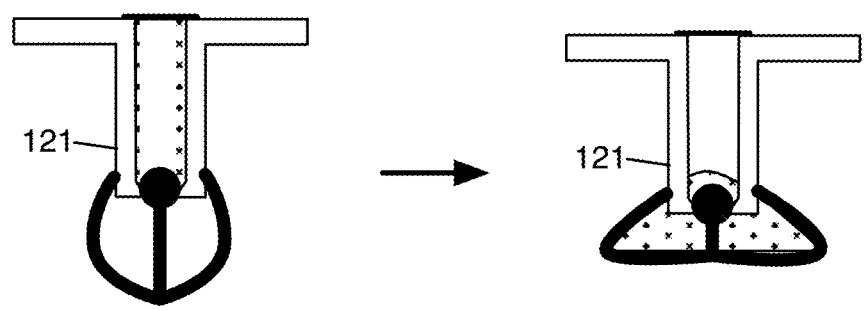
Figure 20C:
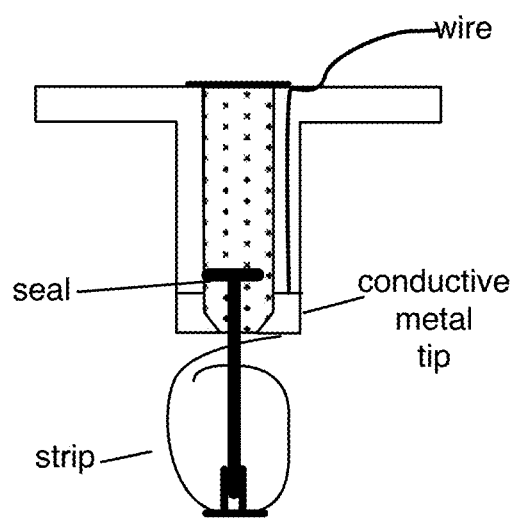

In an alternative variation, as shown in FIG. 16D, the array of permeable bodies 110 can be in an extended state 111b with an ability to undergo elastic deformation (e.g., as sprung tips), such that contact with the body region of the user, or biasing of the array of permeable bodies 110 toward the body region of the user allows the tip regions to elastically deflect outward to enhance contact between the array of permeable bodies 110 and the body region of the user. In examples, as shown in FIGS. 20A-20C, a permeable body 111 having a compliant tip region can be coupled to a valve 117 within a channel of the housing 105, wherein biasing the tip region of the permeable body 11 toward the body region of the user simultaneously displaces the valve 117 to release a volume of fluid toward the tip region and allows the tip region to deflect outward to enhance contact with the body region of the user. In these examples, the tip region can interface with the housing 105 in any suitable manner (e.g., the tip region can be at least partially seated within a channel of the housing, the tip region can be coupled to an external portion of the housing 105, etc.). Additionally or alternatively, portions of the housing 105 in communication with a permeable body 111 can be configured to conduct current be being composed of a conductive material and/or by coupling to a conductive trace that is in communication with the electronics subsystem 160.

Any one or more of the above variations and examples can additionally or alternatively use a material with shape-memory behavior (e.g., nitinol, etc.) to drive transitioning of a permeable body 111 between a contracted state 111a and an extended state 111b. Furthermore, to support formation of an electrical interface between the system 100 and the body region of the user, a conductive material (e.g., putty, material with non-Newtonian behavior, a material with temperature-dependent viscosity, a memory foam saturated with electrolyte, etc.) can be used to promote a desired level of contact between the system 100 and the body region of the user during use of the system 100. Additionally or alternatively, vibration (e.g., ultrasonic vibration, mechanical vibration) can be used by a vibration module of the system 100 to encourage movement of the array of permeable bodies 110 through hair of the user and into position at the body region of the user. Vibration can also be used to indicate, to the user, that proper positioning of the array of permeable bodies 110 at the body region is occurring or has occurred.

In still alternative variations, the hair displacement module 180 comprises at least one comb 181 and at least one actuator 182 (e.g., automatic or manual actuator) that facilitates actuation of the comb 181 in a direction parallel to the surface of the user's skin. In this variation, the comb(s) can be flexible or rigid, and can comprise any suitable shape/configuration of protrusions. In this variation, upon application of the system 100 to the user, the comb(s) 181 can be laterally displaced by the actuator(s) 182, thus parting the user's hair and allowing stimulating/sensing elements of the system 100 to contact the user's skin. In a specific example of this variation, the combs 181 include protrusions that are oriented in a lateral direction, as well as protrusions that are oriented in a direction perpendicular to the user's skin surface, which cooperate to facilitate hair gripping and lateral displacement of hair. In the specific example, the combs 181 are also flexible to allow the combs 181 to bend upward away from the skin after they have been laterally displaced. In this manner, the hair displacement module 180 can also function to mitigate a biasing force on the system 100 by the user's hair. Variations of the combs are shown in FIG. 14B.

Combinations of the above variations and examples can, however, be configured in any other suitable manner.

As shown in FIGS. 21A-21D, the electrode system 100 can additionally or alternatively further comprise a hair gripping module 190, which functions to provide a biasing force between the user's scalp and the system 100, in order to provide robust coupling between the system 100 and the user. In the orientation shown in FIGS. 21A-21D, the hair gripping module 190 preferably provides a downward force (e.g., toward the user's scalp), and can additionally or alternatively be configured to provide opposing lateral forces, relative to the surface of the user's skin, thereby facilitating robust coupling between the user and the system 100. The hair gripping module 190 can be configured at any position proximal a housing 105 of the system 105 or proximal any other suitable element of the system 100.

In one variation, the hair gripping module 190 comprises at least one elastic element 191 (e.g., spring, elastomer) configured to deform and define openings 192 that can receive a user's hair. The elastic element(s) 191 is/are preferably polymeric and non-conducting, which inhibits shorting of any current to the user during stimulation, and reduce electronic noise that interferes with any detected signals. However, the elastic element(s) 191 can be composed of any suitable conducting material (e.g., metal) or non-conducting material. In this variation, the elastic element(s) 191 are oriented about a periphery of a footprint of an element of the system 100 (e.g., a housing 105 of the electrode system 100). In a first configuration (e.g., a default state), with no force applied to the elastic element, openings 192 of the elastic element 191 are smaller than a defining dimension of the user's hair, and the user's hair is unable to be received within the openings 192 of the elastic element(s) 191. In a second configuration, however, a force applied to the elastic element(s) 191 causes a deformation in the elastic element(s) 191 that enables the openings 192 to expand and receive the user's hair. Then, in a return to the first configuration, the user's hair is trapped within the openings 192 of the elastic element(s) 191, in a manner that can be reversed by reapplying a force to the elastic element(s) 191. In specific examples, the elastic element(s) 191 can include springs with coils defining openings 192, and/or elastomeric elements with openings 192 defined within the elastomeric elements.

Figure 21A:
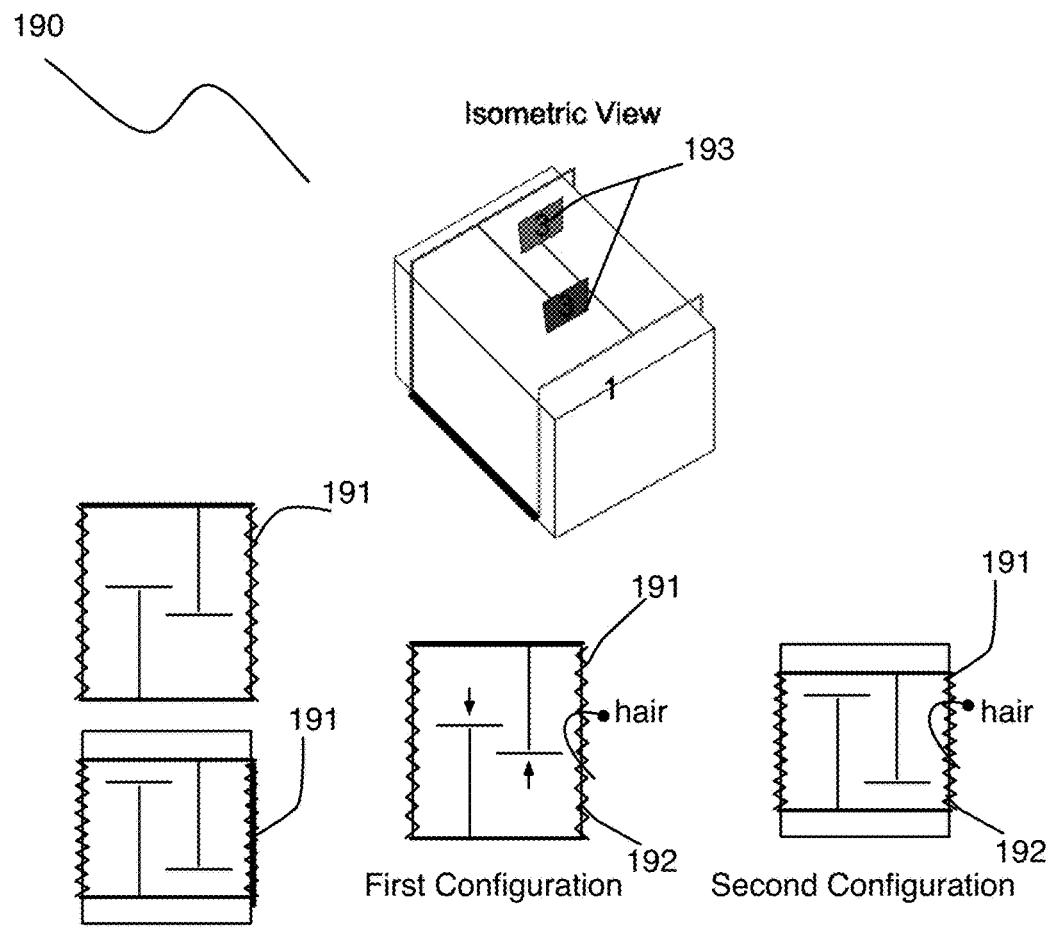
FIGS. 21A-21D depict embodiments of modules for gripping a user's hair, in embodiments of a system for providing electrical stimulation to a user.

In an example of this variation of the hair gripping module 190, as shown in FIG. 21A, an axial force can be applied to one or more ends of an elastic element 191, in a manner that facilitates expansion of the openings 192 (e.g., an increase in an inter-coil distance) to a dimension greater than or equal to a defining dimension (e.g., hair diameter) of the user's hair. In this example, forces exerted by the user's hair on a housing 105 of the system 100 enhance coupling between the housing 105 of the system and the user, as facilitated by anchoring of the user's hair at the user's scalp. The axial force(s) can be enabled by at least one actuator 193, as shown in FIG. 21A, such as a solenoid motor, a DC motor, an AC motor, and/or a stepper motor.

Figure 21B:
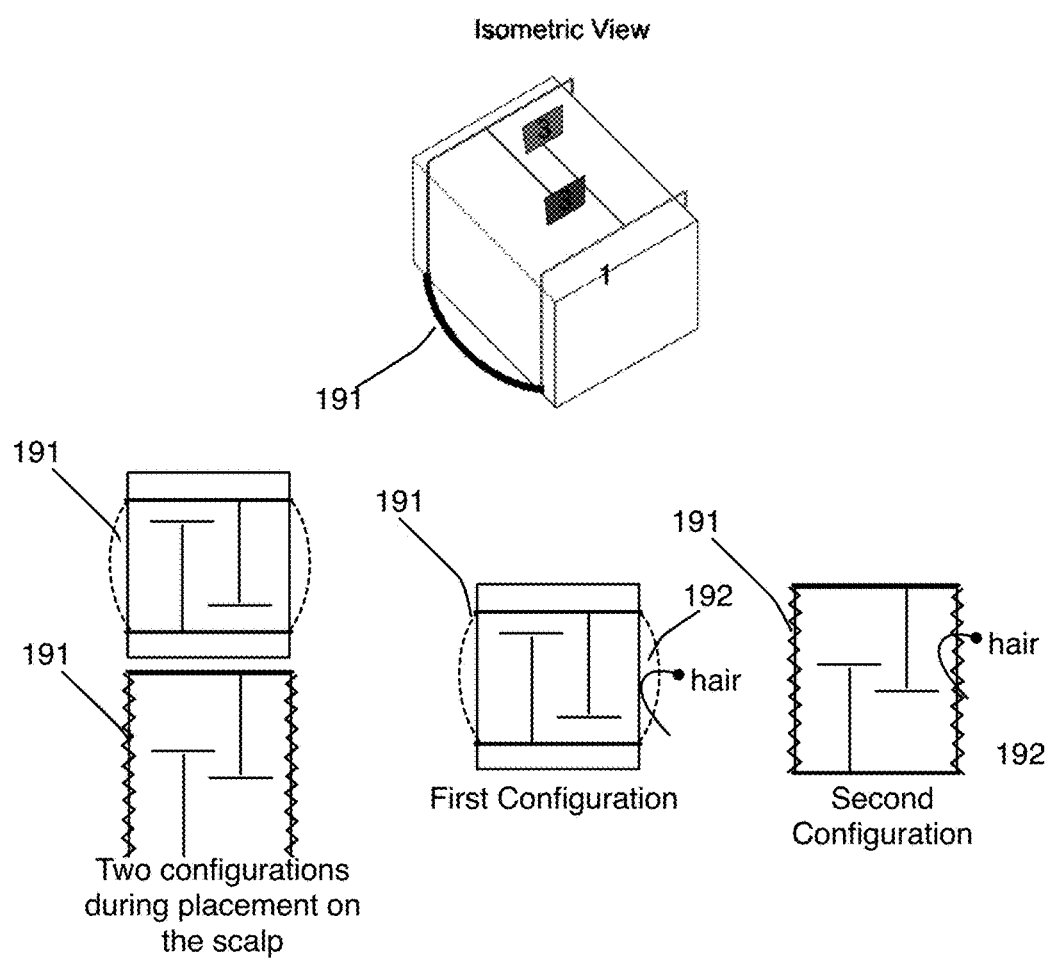

In a second example of this variation of the hair gripping module 190, as shown in FIG. 21B, a transverse force and/or a bending force can be applied to a portion of an elastic element 191, which produces bending of the elastic element 191. The bending allows expansion of the openings 192 of the elastic element 191 (e.g., expansion of inter-coil spacing near an apex of bending in a spring), thereby initiating and enabling hair gripping. In this example, forces exerted by the user's hair on a housing 105 of the system 100 enhance coupling between the system 100 and the user, as facilitated by anchoring of the user's hair at the user's scalp. Furthermore, in this example, lateral forces directed away from the system 100 (e.g., in a direction parallel with the user's scalp) can be provided that further enhance coupling between the system 100 and the user. Lateral forces occur in response to straightening of a bent elastic element, which reduces an opening dimension (e.g., an inter-coil distance) below hair-width before the elastic element has fully returned to a straightened state. In this manner, the user's hair is gripped by the elastic element(s) and then pulled along with the elastic element(s) 191 during straightening of the elastic element(s) 191. Thus, elastic elements located at opposing sides of a housing 105 of the system 100 can be configured to provide lateral forces directed away from the system 100, thereby maintaining a position of the electrode system 100 on the surface of the scalp.

Figure 21C:
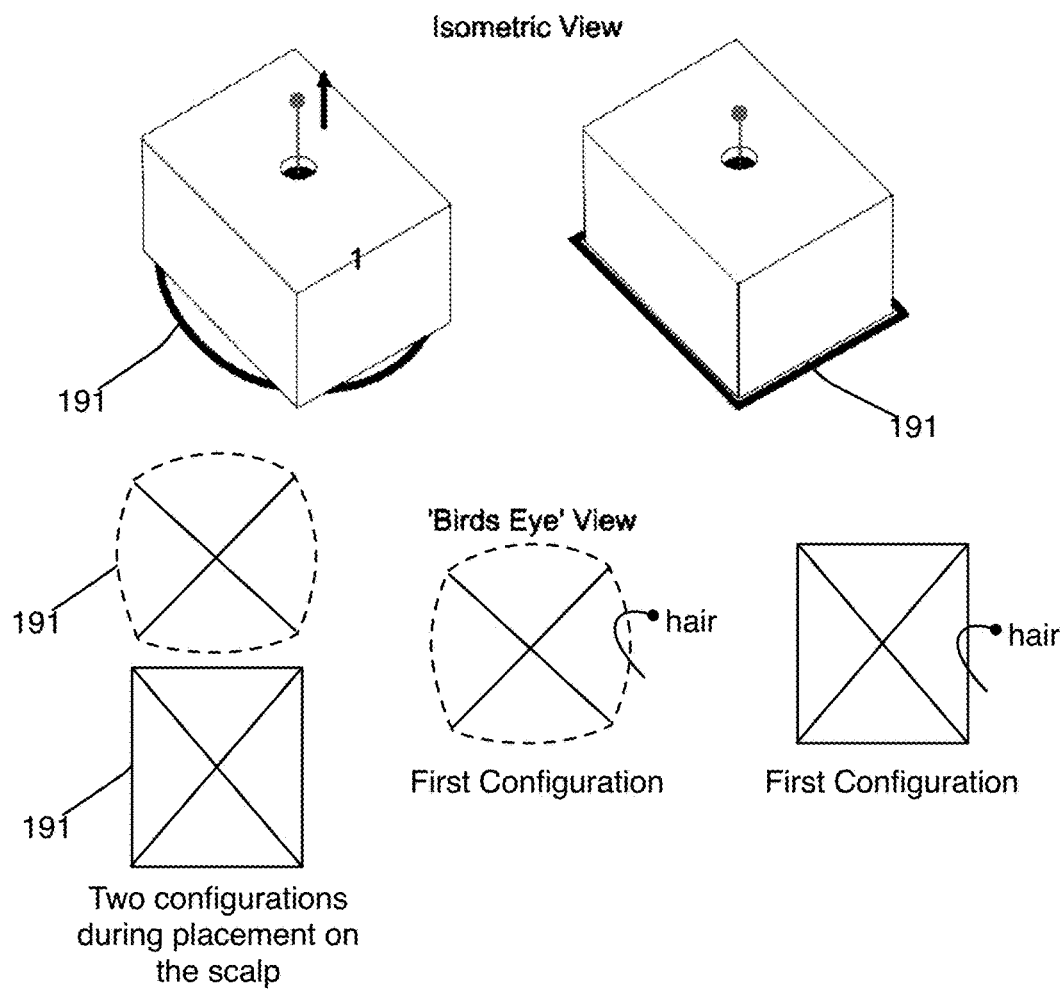
Figure 21D:
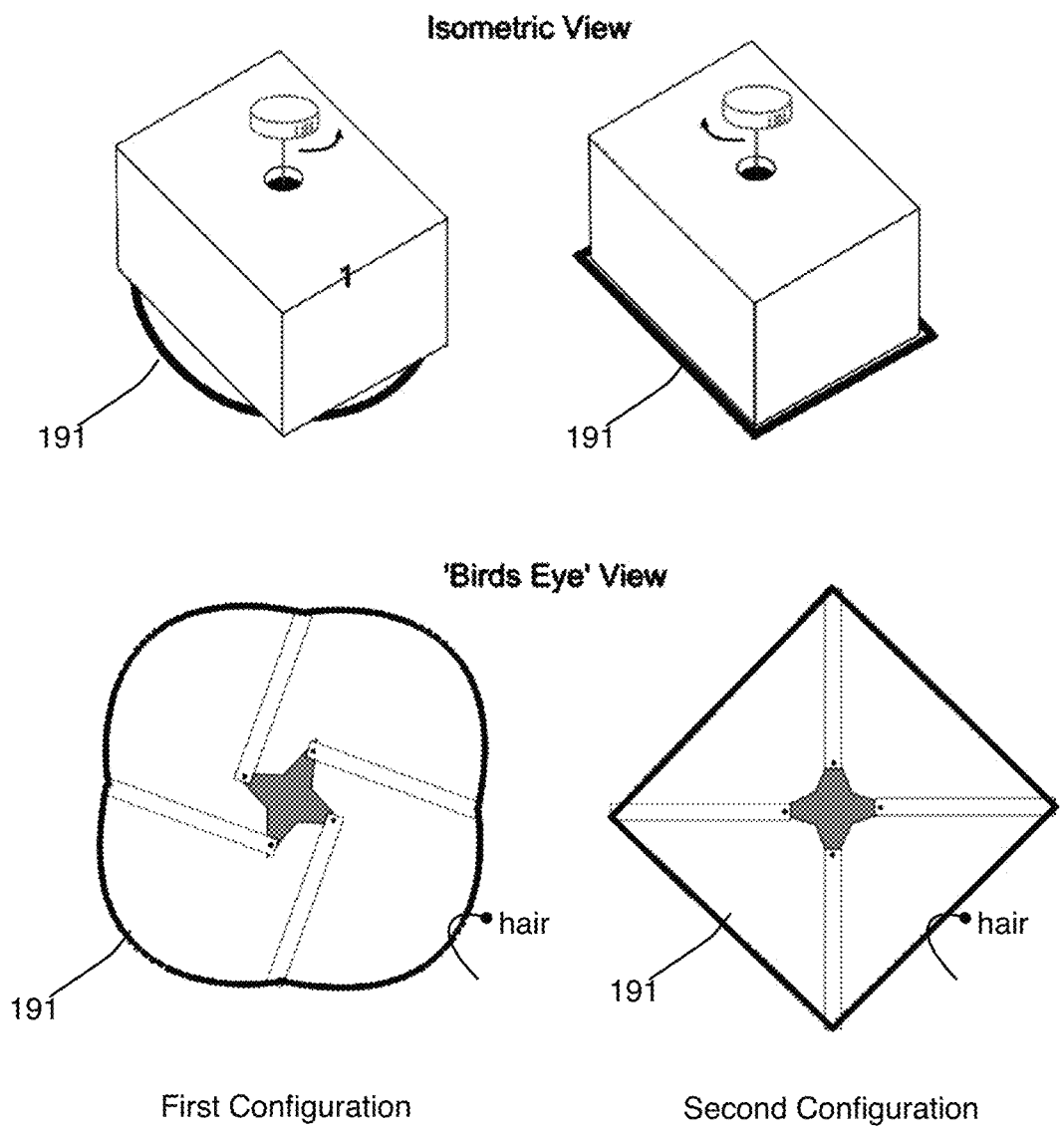

In the second example of this variation of the hair gripping module 190, the transverse/bending force can be applied to the end(s) of an elastic element 191 by any one or more of: of a sliding mechanism, as shown in FIG. 21B, a force provided in an out-of-plane direction to a plane defined by the elastic element(s) 191, as shown in FIG. 21C, and by way of a torsional mechanism, as shown in FIG. 13D. In the examples shown in FIGS. 21C-21D, out-of plane forces and/or torsional forces can be applied to one or more elastic elements 191 arranged about a periphery of a footprint of the housing 105 of the system 100, by way of couplers (e.g., filament, fiber, string, wire, flexible coupler, rigid coupler) coupling the elastic element(s) 191 to at least one actuator 193 providing the out-of-plane/torsional force. The actuator 193 in these examples can include a solenoid motor, a DC motor, an AC motor, a stepper motor, and/or any other suitable actuator, and can be coupled to a pulley subsystem or any other suitable subsystem configured to transmit the out-of-plane and/or torsional force(s).

The system 100 can, however, comprise any other suitable element(s) or combination of elements that enable displacement of a user's hair and/or enhance coupling between the electrode system 100 and the user.

The system 100 and method of the preferred embodiment and variations thereof can be embodied and/or implemented at least in part as a machine configured to receive a computer-readable medium storing computer-readable instructions. The instructions are preferably executed by computer-executable components preferably integrated with the system 100 and one or more portions of the processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the field of biosignals or neurostimulation will recognize from the previous detailed description and from the figures and claims, modifications and changes can be made to the preferred embodiments of the invention without departing from the scope of this invention defined in the following claims.

We claim:

1. A system for electrically stimulating a user, the system comprising:
   an array of permeable bodies that facilitates electrical coupling between the system and a body region of the user during use,
   wherein each of the array of permeable bodies has a cavity at a proximal portion and a tapered distal portion, is configured to transmit an electrolyte solution, through hair of the user, to the body region of the user during use and is composed of an olefin polymer that elastically deforms upon interfacing with the body region of the user;
   a substrate region defining an array of protrusions corresponding to and configured to reside within cavities of the array of permeable bodies, the substrate region composed of a conductive material;
   a set of conductors in communication with the substrate region, the set of conductors configured to couple to an electronics subsystem for transmission of current through the set of conductors and the array of permeable bodies for electrically stimulating the user during use of the system; and a housing portion defining an array of openings at a broad surface, wherein distal portions of the array of permeable bodies are exposed through the array of openings of the housing portion.

2. The system of claim 1, further comprising a second housing portion coupled to the housing portion, the housing portion and the second housing portion defining a volume within which the substrate region and the set of conductors are sealed, and wherein at least one of the housing portion and the second housing portion includes a ferromagnetic material region that interfaces the system with a magnet of an external headset that couples the system to the user.

3. The system of claim 1, wherein a base region of each opening of the array of openings of the housing portion is recessed at the broad surface, such that the base region of each opening defines a bowl about its corresponding opening.

4. The system of claim 1, wherein each of the array of permeable bodies is impregnated with an electrolyte component and configured to be saturated with fluid, thereby generating the electrolyte solution from fluid combined with the electrolyte component, prior to use by the user.

5. The system of claim 1, further comprising an electromechanical coupler configured to couple the set of conductors to an electronics subsystem for transmission of current through the set of conductors and to the array of permeable bodies.

6. The system of claim 5, wherein the electromechanical coupler includes an electronics substrate having a detection connector coupled through a resistor, having a characteristic value, to a stimulation connector, wherein the electronics substrate is configured to reversibly interface with a detection circuit, of the electronics subsystem, that provides a probe voltage to the stimulation connector, thereby producing a characteristic voltage at the detection connector that is determined by the detection circuit.

7. The system of claim 6, wherein the characteristic voltage is indicative of a specific electrode unit of the system, and wherein electronics subsystem is configured generate an alert output upon detection that the characteristic voltage corresponds to an electrode unit system configuration unsuitable for use by the user.

8. The system of claim 1, wherein the set of conductors includes a first conductor configured to provide a first subset of the array of permeable bodies with a first polarity and a second conductor configured to provide a second subset of the array of permeable bodies with a second polarity.

9. The system of claim 8, wherein the substrate region comprises a first subregion coupled to the first subset of the array of permeable bodies and a second subregion coupled to the second subset of the array of permeable bodies, wherein the first subregion of the substrate region is separated from the second subregion of the substrate region by an insulator.

10. The system of claim 1, wherein the second conductor of the set of conductors is configured to provide both the second subset and a third subset of the array of permeable bodies with the second polarity, wherein the first subset of the array of permeable bodies forms a first rectangular subarray, the second subset forms a second rectangular subarray adjacent a first side of the first rectangular subarray, and the third subset forms a third rectangular subarray adjacent a second side of the first rectangular subarray.

11. A system for electrically stimulating a user, the system comprising:
an array of permeable bodies that facilitates electrical coupling between the system and a body region of the user during use,
wherein each of the array of permeable bodies has a cavity, is composed of a polymer that elastically deforms upon interfacing with the body region of the user, and is configured to transmit an electrolyte solution to the body region of the user during use;
a substrate region defining an array of protrusions corresponding to and configured to reside within cavities of the array of permeable bodies, the substrate region composed of a conductive material; and
a set of conductors in communication with the substrate region, the set of conductors configured to couple to an electronics subsystem for transmission of current through the set of conductors and the array of permeable bodies to the body region of the user; and
a housing portion defining an array of openings at a broad surface, wherein each of the array of permeable bodies has a tapered distal portion exposed through the array of openings of the housing portion.

12. The system of claim 11, wherein a base region of each opening of the array of openings of the housing portion is recessed at the broad surface, such that the base region of each opening defines a bowl about its corresponding opening.

13. The system of claim 11, wherein each of the array of permeable bodies is composed of an olefin polymer foam.

14. The system of claim 11, wherein the substrate region comprises a first subregion coupled to a first subset of the array of permeable bodies and a second subregion coupled to a second subset of the array of permeable bodies, wherein the first subregion of the substrate region is separated from the second subregion of the substrate region by an insulator.

15. The system of claim 11, wherein each of the array of permeable bodies is impregnated with a dried electrolyte component, and configured to be saturated with fluid prior to use by the user in forming an electrically conductive interface with the user.

16. The system of claim 11, wherein the set of conductors comprises a first conductor configured to provide a first subset of the array of permeable bodies with a first polarity and a second conductor configured to provide both a second subset and a third subset of the array of permeable bodies with a second polarity.

17. The system of claim 16, wherein the first subset forms a first rectangular subarray, the second subset forms a second rectangular subarray adjacent a first side of the first rectangular subarray, and the third subset forms a third rectangular subarray adjacent a second side of the first rectangular subarray.

18. The system of claim 11, further comprising a second housing portion, wherein the housing portion and the second housing portion define a volume within which the substrate region and the set of conductors are sealed, and wherein at least one of the housing portion and the second housing portion includes a ferromagnetic material region that interfaces the system with a magnet of an external headset that couples the system to the user.

* * * * *

UNITED STATES PATENT AND TRADEMARK OFFICE
CERTIFICATE OF CORRECTION

PATENT NO. : 10,238,869 B2
APPLICATION NO. : 15/289653
DATED : March 26, 2019
INVENTOR(S) : Brett Wingeier et al.

It is certified that error appears in the above-identified patent and that said Letters Patent is hereby corrected as shown below:

In the Claims

Column 42, Line 14, Claim 11 after "material;", delete "and"

Signed and Sealed this
Eighteenth Day of February, 2020

Andrei Iancu
*Director of the United States Patent and Trademark Office*